US012409206B2

(12) United States Patent
Ure et al.

(10) Patent No.: US 12,409,206 B2
(45) Date of Patent: Sep. 9, 2025

(54) USE OF CYCLOSPORINE ANALOGUES FOR TREATING FIBROSIS

(71) Applicant: Hepion Pharmaceuticals, Inc., Edison, NJ (US)

(72) Inventors: Daren R. Ure, Edmonton (CA); Daniel J. Trepanier, Edmonton (CA); Patrick R. Mayo, Edmonton (CA); Robert T. Foster, Edmonton (CA)

(73) Assignee: Hepion Pharmaceuticals, Inc., Edison, NJ (US)

( * ) Notice: Subject to any disclaimer, the term of this patent is extended or adjusted under 35 U.S.C. 154(b) by 0 days.

(21) Appl. No.: 17/179,406

(22) Filed: Feb. 19, 2021

(65) Prior Publication Data

US 2021/0260153 A1    Aug. 26, 2021

Related U.S. Application Data

(60) Provisional application No. 62/981,383, filed on Feb. 25, 2020, provisional application No. 62/978,526, filed on Feb. 19, 2020.

(51) Int. Cl.
| | | |
|---|---|---|
| *A61K 38/13* | (2006.01) | |
| *A61K 45/06* | (2006.01) | |
| *A61P 1/16* | (2006.01) | |
| *A61P 19/04* | (2006.01) | |

(52) U.S. Cl.
CPC .............. *A61K 38/13* (2013.01); *A61K 45/06* (2013.01); *A61P 1/16* (2018.01); *A61P 19/04* (2018.01)

(58) Field of Classification Search
CPC ........... A61K 38/13; A61K 45/06; A61P 1/16; A61P 19/04
See application file for complete search history.

(56) References Cited

U.S. PATENT DOCUMENTS

| 5,720,950 | A | 2/1998 | Poiani et al. |
|---|---|---|---|
| 10,100,311 | B2 | 10/2018 | Chai et al. |
| 2012/0189672 | A1 | 7/2012 | Iacono et al. |
| 2017/0337322 | A1* | 11/2017 | Cales ............... G16B 5/00 |
| 2018/0296588 | A1 | 10/2018 | Foster et al. |
| 2021/0269479 | A1* | 9/2021 | Ure ................... A61K 31/704 |

FOREIGN PATENT DOCUMENTS

| JP | 2010535205 A | 11/2010 |
|---|---|---|
| JP | 2010536844 | 12/2010 |
| WO | WO2000/045834 | 8/2000 |
| WO | 2011081214 A1 | 7/2011 |
| WO | WO2012/079172 | 6/2012 |
| WO | WO2018/106928 | 6/2018 |
| WO | WO2020/112562 | 6/2020 |

OTHER PUBLICATIONS

CRV431 from IUPHAR/BPS Guide to Pharmacology, pp. 1-2. Accessed Nov. 30, 2022. (Year: 2022).*
Banker & Rhodes, "Modern Pharmaceutics," 4th Edition, Drugs and the Pharmaceutical Sciences 2002, 285 pages.
Heydemann et al., "Genetic background influences muscular dystrophy," Neuromuscular Disorders 2005, 15(9-10), 601-609.
Inase et al., "Cyclosporin A Followed by the Treatment of Acute Exacerbation of Idiopathic Pulmonary Fibrosis with Corticosteroid," Internal Medicine 2003, 42(7), 565-570.
International Search Report and Written Opinion dated Aug. 9, 2021 in Patent Application No. PCT/US2021/019480.
International Search Report and Written Opinion dated Jun. 14, 2021 in Patent Application No. PCT/US2021/018639.
Invitation to Pay Additional Fees and, Where Applicable, Protest Fee dated Jun. 14, 2021 in PCT Patent Application No. PCT/US2021/019480.
Kuo et al., "A Pan-Cyclophilin Inhibitor, CRV431, Decreases Fibrosis and Tumor Development in Chronic Liver Disease Models," The Journal of Pharmacology 2019, 371, 231-241.
Nema & Brendel, "Excipients and Their Role in Approved Injectable Products: Current Usage and Future Directions," PDA Journal of Pharmaceutical Science and Technology 2011, 65(3), 287-332.
Powell et al., "Compendium of Excipients for Parenteral Formulations," PDA Journal of Pharmaceutical Science & Technology 1998, in 1 page.
Remington, "The Science and Practice of Pharmacy," 21st Edition, Lippincott Williams & Wilkins 2005, in 14 pages. Preface/Abstract Submitted.
Slater et al., "Cyclosporin A Reverses Vincristine and Daunorubicin Resistance in Acute Lymphatic Leukemia In Vitro," Journal Clinical Investigation 1986, 77, 1405-1408.
Swaggart, "Distinct genetic regions modify specific muscle groups in muscular dystrophy," Physiol Genomics 2011, 43, 24-31.
Yamazaki et al., "Antifibrotic effects of cyclosporine A on TGF-b1-treated lung fibroblasts and lungs from bleomycin-treated mice: role of hypoxia-inducible factor-1a," The FASEB Journal 2017, 31, 3359-3371.

* cited by examiner

*Primary Examiner* — Julie Ha
(74) *Attorney, Agent, or Firm* — Fenwick & West LLP; Heidi A. Erlacher; Eric A. Owens

(57) ABSTRACT

Disclosed herein include methods, compositions, and kits suitable for use in preventing, treating or reverse fibrosis. The methods comprise administering to a subject in need thereof a composition comprising a cyclosporine analogue (for example, CRV431), or a pharmaceutically acceptable salt, solvate, stereoisomer thereof. The compositions and kits comprise a cyclosporine analogue (for example, CRV431), or a pharmaceutically acceptable salt, solvate, stereoisomer thereof.

19 Claims, 21 Drawing Sheets

USE OF CYCLOSPORINE ANALOGUES FOR TREATING FIBROSIS

CROSS-REFERENCE TO RELATED APPLICATIONS

This application claims the benefit of priority to U.S. Provisional Patent Application No. 62/978,526, filed Feb. 19, 2020, and U.S. Provisional Patent Application No. 62/981,383, filed Feb. 25, 2020. The content of each of these related applications is incorporated herein by reference in its entirety.

BACKGROUND

Field

The present disclosure relates generally to the fields of molecular biology and medicine. One aspect relates to prevent, treating and reversing fibrosis with cyclophilin inhibitors.

Description of the Related Art

Fibrosis is a pathological condition characterized by uncontrolled deposition and diminished clearance of fibrous connective tissue proteins, and ultimately leads to fatal, end-stage organ scarring. Tissue fibrosis can occur across all organs. Fibrotic disorders remain very challenging to treat clinically, for example therapeutic options are extremely limited for idiopathic pulmonary fibrosis (IPF) and scleroderma.

There is a need to find antifibrotic agents that are effective in preventing, treating, and reversing fibrosis affecting various organs, including non-liver fibrosis.

SUMMARY

Disclosed herein include a method for treating non-liver fibrosis. The method can, for example, comprise administering to a subject in need thereof a composition comprising cyclosporine analogue of Formula L, or a pharmaceutically acceptable salt, solvate, stereoisomer thereof,

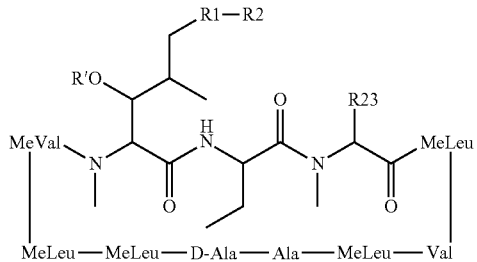

Formula L wherein:
a. R' is H or acetyl;
b. R1 is a saturated or unsaturated straight or branched aliphatic carbon chain from 2 to 15 carbon atoms in length;
c. R2 is selected from the group consisting of:
   i. H;
   ii. an unsubstituted, N-substituted, or N,N-disubstituted amide;
   iii. a N-substituted or unsubstituted acyl protected amine;
   iv. a N-substituted or unsubstituted amine;
   v. a carboxylic acid;
   vi. a nitrile;
   vii. an ester;
   viii. a ketone;
   ix. a hydroxy, dihydroxy, trihydroxy, or polyhydroxy alkyl; and
   x. a substituted or unsubstituted aryl;
   xi. a saturated or unsaturated. straight or branched aliphatic chain optionally containing a substituent selected from the group consisting of a hydrogen, a ketone, a hydroxyl, a nitrile, a carboxylic acid, an ester, a 1,3-dioxolane, a halogen, and an oxo;
   xii. an aromatic group containing a substituent selected from the group consisting of a halogen, an ester, and a nitro; and
   xiii. a combination of the saturated or unsaturated, straight or branched aliphatic chain of (xi) and the aromatic group of (xii); and
d. R23 is a saturated or unsaturated straight chain or branched optionally substituted aliphatic carbon chain.

The subject in need thereof can be a subject suffering from non-liver fibrosis. The method can comprise reducing the amount of non-liver fibrosis in the subject. In some embodiments, the amount of non-liver fibrosis in the subject is reduced by 5%, 10%, 20%, or more. The method can comprise reducing formation of non-liver fibrosis in the subject. In some embodiments, the formation of non-liver fibrosis in the subject is reduced by 5%, 10%, 20%, or more.

Non-limiting examples of non-liver fibrosis include fibrosis in lung, liver, kidney, heart, skin, eye, gastrointestinal tract, peritoneum, bone marrow, muscle, blood vessel, vasculature, or any combination thereof. In some embodiments, subject in need thereof is a subject suffering from a fibrotic disorder selected from the group consisting of idiopathic pulmonary fibrosis (IPF), cardiac fibrosis, dermal fibrosis, renal fibrosis, or a combination thereof.

Also included herein is a method for preventing or delaying the onset of fibrosis. The method can, for example, comprise administering to a subject in need thereof a composition comprising cyclosporine analogue of Formula L, or a pharmaceutically acceptable salt, solvate, stereoisomer thereof,

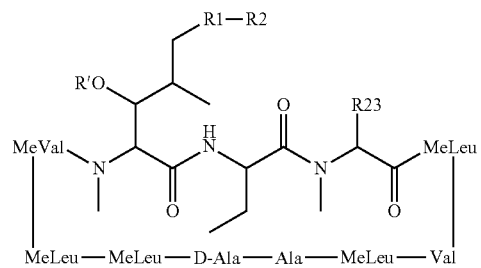

Formula L wherein:
a. R' is H or acetyl;
b. R1 is a saturated or unsaturated straight or branched aliphatic carbon chain from 2 to 15 carbon atoms in length;

c. R2 is selected from the group consisting of:
  i. H;
  ii. an unsubstituted, N-substituted, or N,N-disubstituted amide;
  iii. a N-substituted or unsubstituted acyl protected amine;
  iv. a N-substituted or unsubstituted amine;
  v. a carboxylic acid;
  vi. a nitrile;
  vii. an ester;
  viii. a ketone;
  ix. a hydroxy, dihydroxy, trihydroxy, or polyhydroxy alkyl; and
  x. a substituted or unsubstituted aryl;
  xi. a saturated or unsaturated. straight or branched aliphatic chain optionally containing a substituent selected from the group consisting of a hydrogen, a ketone, a hydroxyl, a nitrile, a carboxylic acid, an ester, a 1,3-dioxolane, a halogen, and an oxo;
  xii. an aromatic group containing a substituent selected from the group consisting of a halogen, an ester, and a nitro; and
  xiii. a combination of the saturated or unsaturated, straight or branched aliphatic chain of (xi) and the aromatic group of (xii); and
d. R23 is a saturated or unsaturated straight chain or branched optionally substituted aliphatic carbon chain.

The subject in need thereof can be, for example, a subject at a risk of developing fibrosis. In some embodiments, the risk of developing fibrosis in the subject is reduced by at least 5%, 10%, 20% or more as compared to untreated subjects. In some embodiments, the onset of fibrosis is delayed in the subject by at least a month, a year, or more.

In some embodiments, the method comprises reducing fibrosis formation, wherein the fibrosis formation is reduced in the subject by at least a month, a year, or more as compared to untreated subjects.

Also included herein is a method for reducing fibrosis or reversing fibrosis. The method can, for example, comprise administering to a subject in need thereof a composition comprising cyclosporine analogue of Formula L, or a pharmaceutically acceptable salt, solvate, stereoisomer thereof, In some embodiments, the subject in need thereof is a subject suffering from fibrosis. In some embodiments, the method comprises inhibiting fibrosis formation in the subject. In some embodiments, the fibrosis is non-liver fibrosis. In some embodiments, the non-liver fibrosis comprises fibrosis in lung, kidney, heart, skin, eye, gastrointestinal tract, peritoneum, bone marrow, muscle, blood vessel, vasculature, or any combination thereof. In some embodiments, the subject in need thereof is a subject suffering from a fibrotic disorder selected from the group consisting of pulmonary fibrosis, cardiac fibrosis, dermal fibrosis, renal fibrosis, hepatic fibrosis, or a combination thereof.

In some embodiments, the subject in need thereof is a subject suffering from idiopathic pulmonary fibrosis (IPF). In some embodiments, the fibrosis is liver fibrosis, for example cirrhosis. In some embodiments, the cirrhosis is associated with viral hepatitis, schistosomiasis and chronic alcoholism.

In some embodiments, the cyclosporine analogue of Formula L is CRV431:

Formula L

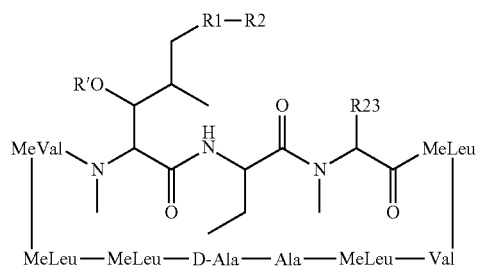

wherein:
a. R' is H or acetyl;
b. R1 is a saturated or unsaturated straight or branched aliphatic carbon chain from 2 to 15 carbon atoms in length;
c. R2 is selected from the group consisting of:
  i. H;
  ii. an unsubstituted, N-substituted, or N,N-disubstituted amide;

(CRV431)

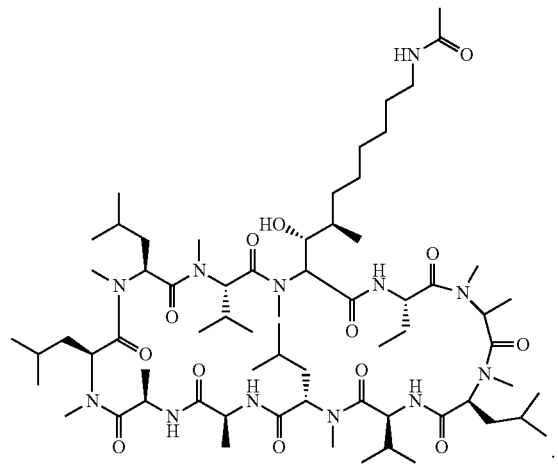

In some embodiments, the composition comprises a therapeutically or prophylactically effective amount of cyclosporine analogue of Formula L, or a pharmaceutically acceptable salt, solvate, stereoisomer thereof.

In some embodiments, the non-liver fibrosis or fibrosis is induced by a therapeutic agent, an injury, or a combination thereof. In some embodiments, the non-liver fibrosis or fibrosis is associated with the accumulation of extracellular matrix constituents that occurs following trauma, inflammation, tissue repair, immunological reactions, cellular hyperplasia, neoplasia, a combination thereof. In some embodiments, the non-liver fibrosis or fibrosis is associated with major organ diseases, fibroproliferative disorders, scarring associated with trauma, or a combination thereof. In some embodiments, the fibrosis is associated with interstitial lung disease, liver cirrhosis, non-alcoholic fatty liver disease, non-alcoholic steatohepatitis, kidney disease, heart or vascular disease, diseases of the eye, systemic and local scleroderma, keloids, hypertrophic scars, atherosclerosis, restenosis, Dupuytren's contracture, surgical complications, chemotherapeutics drug-induced fibrosis, radiation-induced fibrosis, accidental injury and burns, retroperitoneal fibrosis, peritoneal fibrosis/peritoneal scarring, or a combination thereof. In some embodiments, the fibrosis associated with interstitial lung disease is sarcoidosis, silicosis, drug reactions, infections, collagen vascular diseases, rheumatoid arthritis, systemic sclerosis, scleroderma, pulmonary fibrosis, idiopathic pulmonary fibrosis, usual interstitial pneumonitis, interstitial lung disease, cryptogenic fibrosing alveolitis, bronchiolitis obliterans, bronchiectasis, or a combination thereof.

The method can, for example, reduce fibrosis formation in the subject by at least 5%, 10%, 20%, 50%, 70%, 90%, or more as compared to untreated subjects.

In some embodiments, the method comprises delaying fibrosis formation in the subject as compared to untreated subjects. The subject can be, for example, a mammal (e.g., a human). In some embodiments, the composition comprises one or more pharmaceutically acceptable excipients. In some embodiments, the composition comprises one or more additional therapeutic agents.

In some embodiments, the method further comprises administering to the subject in need thereof one or more additional therapeutic agents. In some embodiments, the one or more additional therapeutic agents comprise an additional antifibrotic agent. In some embodiments, the one or more additional therapeutic agents comprises Type II interferon receptor agonists, pirfenidone and pirfenidone analogs, nintedanib and nintedanib analogs, anti-angiogenic agents, anti-inflammatory agents, IL-1 antagonists, angiotensin-converting-enzyme (ACE) inhibitors, angiotensin receptor blockers and aldosterone antagonists, mitomycin C (MMC), 5-fluorouracil (5-FU), adenylyl cyclase activators, β-adenoreceptor agonists, flavonoids, mast cell stabilizers, phosphodiesterase inhibitors, procyanidins, or a combination thereof.

In some embodiments, at least one of the one or more additional therapeutic agents is co-administered to the subject with the composition. In some embodiments, at least one of the one or more additional therapeutic agents is administered to the subject before the administration of the composition, after the administration of the composition, or both. The composition can be administered to the subject by, for example, intravenous administration, oral administration, parenteral administration. The composition can be, for example, in the form of powder, pill, tablet, microtablet, pellet, micropellet, capsule, capsule containing microtablets, liquid, aerosols, or nanoparticles. In some embodiments, the composition is administered to the subject at an effective daily dose of the cyclosporine analogue or a pharmaceutically acceptable salt, solvate, stereoisomer thereof at from 10 mg to 250 mg.

Also provided herein include a pharmaceutical composition, comprising a cyclosporine analogue of Formula L, or a pharmaceutically acceptable salt, solvate, stereoisomer thereof, for use in preventing or treating fibrosis, or for use in preventing or reducing fibrosis formation, or for use in reversing fibrosis, or for reducing the amount of fibrosis, or for delaying the onset of fibrosis

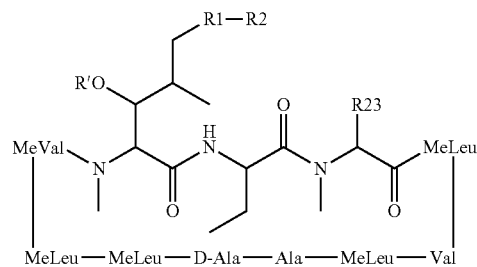

Formula L wherein:
a. R' is H or acetyl;
b. R1 is a saturated or unsaturated straight or branched aliphatic carbon chain from 2 to 15 carbon atoms in length;
c. R2 is selected from the group consisting of:
   i. H;
   ii. an unsubstituted, N-substituted, or N,N-disubstituted amide;
   iii. a N-substituted or unsubstituted acyl protected amine;
   iv. a N-substituted or unsubstituted amine;
   v. a carboxylic acid;
   vi. a nitrile;
   vii. an ester;
   viii. a ketone;
   ix. a hydroxy, dihydroxy, trihydroxy, or polyhydroxy alkyl; and
   x. a substituted or unsubstituted aryl;
   xi. a saturated or unsaturated. straight or branched aliphatic chain optionally containing a substituent selected from the group consisting of a hydrogen, a ketone, a hydroxyl, a nitrile, a carboxylic acid, an ester, a 1,3-dioxolane, a halogen, and an oxo;
   xii. an aromatic group containing a substituent selected from the group consisting of a halogen, an ester, and a nitro; and
   xiii. a combination of the saturated or unsaturated, straight or branched aliphatic chain of (xi) and the aromatic group of (xii); and
d. R23 is a saturated or unsaturated straight chain or branched optionally substituted aliphatic carbon chain.

In some embodiments, the cyclosporine analogue is CRV431:

(CRV431)

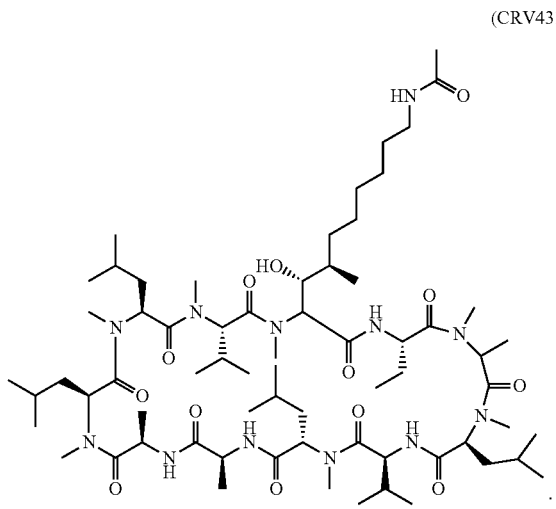

In some embodiments, the pharmaceutical composition is for intravenous administration, oral administration, or parenteral administration. In some embodiments, the pharmaceutical composition is in the form of powder, pill, tablet, microtablet, pellet, micropellet, capsule, capsule containing microtablets, liquid, aerosols, or nanoparticles.

Disclosed herein include a kit, comprising
a pharmaceutical composition disclosed herein; and
a label, wherein the label indicating one or more of:
(a) the kit is for preventing or treating fibrosis,
(b) the kit is for reducing or inhibiting fibrosis formation,
(c) the kit is for reversing fibrosis,
(d) the kit is for reducing the amount of fibrosis, and
(e) the kit is for delaying the onset of fibrosis.

In some embodiments, the kit further comprises instructions for identifying a subject at risk of development fibrosis, instructions for identifying a subject suffering from fibrosis, or both

DETAILED DESCRIPTION

Figure 1A:
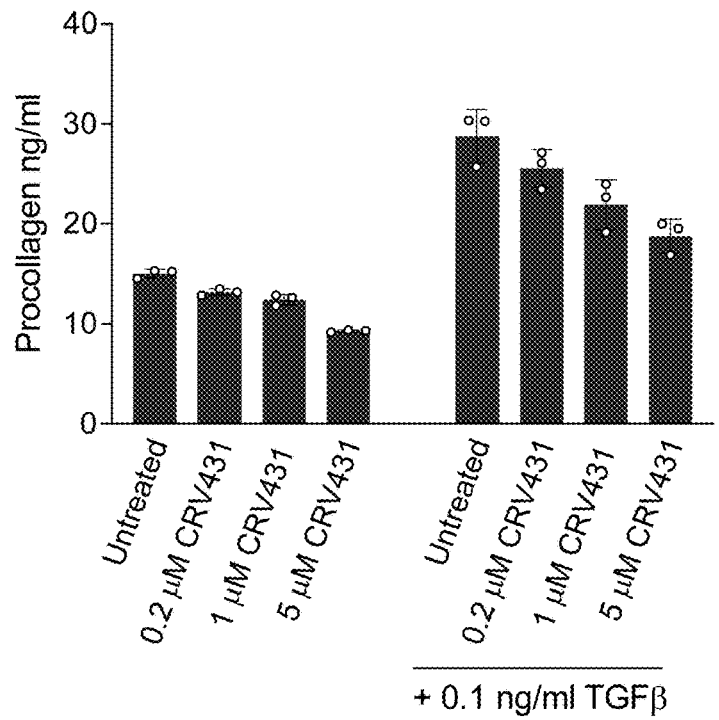
FIGS. 1A-B are histograms showing dose-dependent decreases in the abundance of procollagen and fibronectin caused by CRV431 treatment in human LX-2 hepatic stellate cell culture.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, NY 1994); Sambrook et al., Molecular Cloning, A Laboratory Manual, Cold Spring Harbor Press (Cold Spring Harbor, NY 1989). For purposes of the present disclosure, the following terms are defined below.

As used herein, a "subject" refers to an animal that is the object of treatment, observation or experiment. "Animals" include cold- and warm-blooded vertebrates and invertebrates such as fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, and apes, and, in particular, humans.

As used herein, a "patient" refers to a subject that is being treated by a medical professional, such as a Medical Doctor (i.e., Doctor of Allopathic medicine or Doctor of Osteopathic medicine) or a Doctor of Veterinary Medicine, to attempt to cure, or at least ameliorate the effects of, a particular disease or disorder or to prevent the disease or disorder from occurring in the first place.

As used herein, "administration" or "administering" refers to a method of giving a dosage of a pharmaceutically active ingredient to a vertebrate.

As used herein, a "dosage" refers to the combined amount of the active ingredients (e.g., cyclosporine analogues, including CRV431).

As used herein, a "unit dosage" refers to an amount of therapeutic agent administered to a patient in a single dose.

As used herein, a "daily dosage" refers to the total amount of therapeutic agent administered to a patient in a day, As used herein, "therapeutically effective amount" or "pharmaceutically effective amount" is meant an amount of therapeutic agent, which has a therapeutic effect. The dosages of a pharmaceutically active ingredient which are useful in treatment when administered alone or in combination with one or more additional therapeutic agents are therapeutically effective amounts. Thus, as used herein, a therapeutically effective amount means an amount of therapeutic agent which produces the desired therapeutic effect as judged by clinical trial results and/or model animal studies.

As used herein, the term "treat," "treatment," or "treating," refers to administering a therapeutic agent or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition. As used herein, a "therapeutic effect" relieves, to some extent, one or more of the symptoms of a disease or disorder. For example, a therapeutic effect may be observed by a reduction of the subjective discomfort that is communicated by a subject (e.g., reduced discomfort noted in self-administered patient questionnaire).

As used herein, the term "prophylaxis" or "prevention" refers the preventive treatment of a subclinical disease-state in a subject, e.g., a mammal (including a human), for reducing the probability of the occurrence of a clinical disease-state. The subject is selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

Fibrosis

Fibrosis is a pathological condition in which excess accumulation of fibrous connective tissue occurs. In some instances, fibrosis is considered to be the result of acute or chronic stress on the tissue or organ, characterized by extracellular matrix deposition, reduction of vascular/tubule/duct/airway patency and impairment of function ultimately resulting in organ failure. The formation of excess fibrous connective tissue in an organ or tissue can occur in a reactive or reparative process. Reactive fibrosis is a reversible process that appears in the absence of functional cell necrosis (i.e., the affected cells remain alive), whereas reparative fibrosis is accompanied by scar formation after cell death. Fibrosis can affect all tissues and organ systems, including but not limited to, the heart, liver, lung, skeletal muscle, kidney, eyes, blood vessel, skin, brain, bone marrow, gastrointestinal tract, peritoneum, and vasculature. Fibrosis represents the end-stage in a number of chronic tissue diseases representing nearly half of all deaths worldwide: skeletal muscle tissue (e.g., dystrophic muscle disease), cardiac and vascular tissue (e.g., myocardial infarction), liver tissue (e.g., non-alcoholic fatty liver disease/liver cirrhosis), lung tissue (e.g., idiopathic pulmonary fibrosis) and kidney tissue (e.g., chronic kidney disease/renal fibrosis). Fibrosis and fibrotic disorders can be associated with the major organs, including but not limited to, lung, liver, kidney, heart, skin, eye, gastrointestinal tract, peritoneum, bone marrow, or a combination thereof. As described herein, fibrosis can be non-liver fibrosis which is fibrosis present in and/or affecting non-hepatic tissues and an organ other than liver. Non-limiting examples of non-liver fibrosis include fibrosis affecting the heart, lung, skeletal muscle, kidney, eyes, blood vessel, skin, brain, bone marrow, gastrointestinal tract, peritoneum, and vasculature. Examples of non-liver fibrotic disorder include, but are not limited to, a fibrotic condition associated with lung, kidney, heart, skin, eye, gastrointestinal tract, peritoneum, bone marrow, muscle (e.g., skeletal muscle), blood vessel, vasculature, or any combination thereof.

As used herein, an fibrotic disease or condition is any disease or condition characterized by the formation of excess fibrous connective tissue. A common feature of these diseases is hyperproliferation of fibrotic cells, and the tissue or organ fibrosis often includes pulmonary fibrosis, hepatic fibrosis, chronic pancreatitis, scleroderma, glomerular fibrosis and multiple organ fibrosis caused by radiochemotherapy and tissue transplantation. The formation of excess fibrous connective tissue may be in response to a reparative or reactive process. Fibrosis includes, but is not limited to, pulmonary fibrosis, liver fibrosis, myelofibrosis, skin fibrosis (e.g., nephrogenic systemic fibrosis and keloid fibrosis), mediastinal fibrosis, cardiac fibrosis, kidney fibrosis, stromal fibrosis, epidural fibrosis, epithelial fibrosis, idiopathic fibrosis, cirrhosis, and any combination thereof.

In some embodiments, fibrosis is a fibrotic condition with accumulation of extracellular matrix constituents that occurs following trauma, inflammation, tissue repair, immunological reactions, cellular hyperplasia, and neoplasia. Non-limiting examples of fibrosis and fibrotic disorders include, but are not limited to, cystic fibrosis; fibrosis and fibrotic disorders associated with major organ diseases, including but not limited to, interstitial lung disease (ILD), liver cirrhosis, non-alcoholic fatty liver disease (NAFLD) and non-alcoholic steatohepatitis (NASH) (hepatic fibrosis), kidney disease (renal fibrosis), heart or vascular disease (cardiac fibrosis) and diseases of the eye; fibroproliferative disorders, including but not limited to, systemic and local scleroderma, keloids and hypertrophic scars, atherosclerosis, restenosis, and Dupuytren's contracture; scarring associated with trauma, including but not limited to, surgical complications, chemotherapeutics drug-induced fibrosis (e.g. bleomycin-induced fibrosis, radiation-induced fibrosis, accidental injury and burns); retroperitoneal fibrosis (Ormond's disease); and peritoneal fibrosis/peritoneal scarring in patients receiving peritoneal dialysis, usually following renal transplantation.

The fibrosis can be ocular fibrosis which includes, but is not limited to, the ocular fibrosis results from an ocular disease or disorder such as diabetic retinopathy, bacterial infection, viral infection, fungal infection, amoeba infection, ocular trauma, chemical corneal burn, thermal corneal burn, pterygium, glaucoma, surgical trauma, Fuch's Endothelial Corneal Dystrophy (FECD), proliferative vitreoretinopathy (PVR, for example anterior proliferative vitreoretinopathy (anterior PVR)), or a combination thereof. The ocular fibrosis can be, for example, retinal fibrosis, corneal fibrosis, conjunctival fibrosis, fibrosis of the trabecular meshwork, or a combination thereof. The ocular fibrosis can comprise, for example, corneal hazing, corneal scarring, trabecular bleb, or a combination thereof. The ocular fibrosis can be resulted from, for example, a corneal burn, pteygium, FECD, glaucoma, or a combination thereof. In some embodiments, the ocular fibrosis comprises retinal fibrosis associated with anti-VEGF treatment.

Renal fibrosis is a fibrotic condition in which fibrosis occurs in scars accumulated due to inflammation in kidney tissue, in which a part of the kidney hardens and loses its function. The hardening of the kidney can lead to chronic renal failure, which can be accompanied by anemia, clotting disorders, hypertension, various complications and infections of cardiopulmonary organs and gastrointestinal tracts. If kidney function drops, for example, below 15 percent of normal, kidneys produce less erythropoietin, resulting in decreased production of red blood cells. In addition, uremia, which is caused by inactive urinary secretion, reduces red blood cell lifespan and causes strong anemia. In addition, the onset of uremia increases the likelihood of systemic infection, which is a major factor in the development of sepsis. In some instances, Kidney disease (may be associated with diabetes) can damage and scar the kidneys leading to a progressive loss of function, and also hypertensive diseases. Kidney fibrosis can occur at any stage of kidney disease, from chronic kidney disease (CKD) through to end-stage renal disease (ESRD). Kidney fibrosis can develop as a result of cardiovascular disease such as hypertension or diabetes, both of which place immense strain on kidney function which promotes a fibrotic response. In some instances, kidney fibrosis can also be idiopathic (without a known cause), and certain genetic mitochondrial diseases also present kidney fibrosis manifestations and associated symptoms.

Fibrotic disorder of the lung includes, for example, pulmonary fibrosis, idiopathic pulmonary fibrosis (IPF), usual interstitial pneumonitis (UIP), interstitial lung disease (ILD), cryptogenic fibrosing alveolitis (CFA), bronchiolitis obliterans, and bronchiectasis. Interstitial lung disease (ILD) includes disorders in which pulmonary inflammation and fibrosis are the final common pathways of pathology, for example, sarcoidosis, silicosis, drug reactions, infections and collagen vascular diseases, such as rheumatoid arthritis and systemic sclerosis (scleroderma). IPF is the most common type of ILD. IPF is known to be caused by an abnormality in the healing process of the damaged area caused by continuously stimulating epithelial cells or goblet cells, but its stimulating factor has not been known. Inflammation of the lung may not directly cause pulmonary fibrosis, but it is known that pulmonary fibrosis occurs due to a difference between a patient with idiopathic pulmonary fibrosis and a normal person in the process of healing to normal tissue following inflammation of the lungs. Another mechanism of fibrosis is deposition and fibrosis of extracellular matrix through activation and proliferation of fibroblasts by T helper type 2 cytokines.

Fibrosis in liver (hepatic fibrosis) can be defined as excessive deposition of the extracellular matrix due to chronic inflammation in the liver. If chronic liver disease persists due to such excessive deposition of extracellular matrix, it eventually processes to cirrhosis due to distortion of the liver's internal structure a decrease in the number of liver cells. Representative cells involved in hepatic fibrosis include hepatic stellate cells, Kupffer cells, and endothelial cells. The activated hepatic stellate cells are the main source of extracellular matrix production and the hepatic stellate cells are involved in increasing the production of various extracellular matrix including collagen. Kupffer cells are located in the sinusoidal space in the liver, and substances produced by activated Kupffer cells affect surrounding hepatic cells, endothelial cells, and hepatic stellate cells, thereby promoting hepatic fibrosis. Endothelial cells not only play an essential role in the regulation of blood flow in the liver, but also are involved in the production of growth factors and extracellular matrix involved in the proliferation of hepatic stellate cells by inflammation or liver fibrosis. Cytokines affecting hepatic fibrosis include transforming growth factor β (TGF-β) and platelet derived growth factor (PDGF). TGF-β is the most potent cytokine that promotes fibrosis of hepatic stellate cells, and hepatic stellate cells themselves are the main source of TGF-β. PDGF is the most potent cytokine that promotes division and proliferation of hepatic stellate cells. In the past, the hepatic fibrosis process has been recognized as an irreversible phenomenon, but recently, it has been reported to be reversibly changed. Thus, it can be a dynamic process. Therefore, it becomes clinically important to measure such change accurately. In some embodiments, the hepatic fibrosis is liver cirrhosis, including, for example, cirrhosis associated with viral hepatitis, schistosomiasis and chronic alcoholism.

In some embodiments, the fibrosis is associated with a heart disease, an eye disease, or a combination thereof. It is known that heart disease can result in scar tissue which impairs the ability of the heart to pump. Non-limiting examples of heart fibrotic condition include atrial fibrosis, endomyocardial fibrosis, and any combination thereof. The eye disease include, but is not limited to, macular degeneration and retinal and vitreal retinopathy, which can impair vision. Fibrosis can be muscle fibrosis, for example reactive muscle fibrosis. The muscle fibrosis can be cardiac fibrosis which includes, but is not limited to, interstitial cardiac fibrosis, perivascular cardiac fibrosis, skeletal muscle fibrosis, and a combination thereof.

Cardiac fibrosis can play an important role in the pathogenesis of heart disease in patients through various distinct mechanisms. Fibrotic myocardial remodeling can impair ventricular diastolic function contributing the development of heart failure with preserved ejection fraction. Development of atrial fibrosis can predispose subjects to atrial tachyarrhythmias. Further, collagen deposition in the ventricular myocardium can contribute to the increased incidence of ventricular arrhythmias and sudden death observed in dysmetabolic individuals. Moreover, in some patients, development of fibrotic changes in the right ventricle can perturb right ventricular function. Additionally, dysmetabolic-related modulation of the reparative fibrotic response following infarction can predispose these subjects to development of post-infarction heart failure. It can be advantageous to attenuate fibrosis for reducing cardiac morbidity and mortality in subjects with altered metabolism.

As described herein, the fibrotic disorder can be, for example, fibrotic vascular disease, cystic fibrosis, pulmonary fibrosis, idiopathic pulmonary fibrosis, musculoskeletal fibrosis, renal fibrotic disease, lymph node fibrosis associated with HIV, inflammatory pulmonary fibrosis, pancreatic fibrosis, hepatic fibrosis, myocardiac fibrosis, or a combination thereof.

The fibrosis can be age-induced (e.g., as a result of a tissue injury or cardiovascular disease), injury-induced, or stress-induced. The age-induced fibrosis can be an age-induced fibrosis of the heart (cardiac), kidney (renal), blood vessels (vascular), liver (hepatic), brain, intestine, skin (dermal), pancreas and lung (pulmonary), or any combination thereof. The fibrosis can be, for example, cardiac fibrosis, liver fibrosis, brain fibrosis, kidney fibrosis, vascular fibrosis, lung fibrosis, dermal fibrosis, or any combination thereof. Non-limiting examples of dermal fibrotic disorders include aberrant wound-healing, wrinkle, cellulite and dermal neoplastic fibrosis, vasculopathy, vasculitis, exuberant burn wound-healing, diabetic foot syndrome, arthrofibrosis, Peyronie's disease, and any combination thereof. Non-limiting examples of brain fibrotic condition include glial scar. In some embodiments, the fibrotic condition is arterial stiffness, arthrofibrosis, Crohn's disease, Dupuytren's contracture, keloid, mediastinal fibrosis, myelofibrosis, Peyronie's disease (PD), nephrogenic systemic fibrosis, progressive massive fibrosis, retroperitoneal fibrosis, burn scar, post-operative fibrosis of any organ, urethral fibrosis, diabetic nephropathy, scleroderma/systemic sclerosis, or any combination thereof. Fibrotic conditions can involve an organ of the gastrointestinal system, e.g., the liver, small intestine, large intestine, or pancreas; an organ of the respiratory system, e.g., the lung; an organ of the cardiovascular system, e.g. the heart or blood vessel; the skin; an organ of the nervous system, e.g. the brain; an organ of the urinary system, e.g., the kidney; and/or an organ of the musculoskeletal system, e.g., muscle tissue. In some embodiments, the fibrosis or fibrotic condition has a known cause and/or trigger, for example, skin burns, post-surgical fibrosis, or a combination thereof. In some embodiments, the fibrosis or fibrotic condition does not have a known cause and/or trigger.

Methods of Prevention and Treatment

Disclosed herein include methods, compositions, and kits for treating fibrosis (for example, one or more fibrotic diseases/disorders). The methods, compositions and kits can, for example, alleviate or ameliorate one or more symptoms of fibrosis in a subject in need thereof. Also disclosed herein are methods, compositions, and kits for preventing (including primary prophylaxis and secondary prophylaxis) of fibrosis (for example, one or more fibrotic diseases/disorders). In addition, methods, compositions, and kits for preventing or delaying onset of fibrosis are provided. Methods, compositions, and kits disclosed herein can, in some embodiments, reverse fibrosis, reduce or inhibit fibrosis formation, and/or reduce the amount of fibrosis in a subject. The fibrosis is, in some embodiments, non-liver fibrosis.

In some embodiments, the method comprises identifying a subject having fibrosis. In some embodiments, the method comprises identifying a subject at a risk of developing fibrosis. The kit can comprise instructions for identifying a subject having fibrosis, instructions for identifying a subject at a risk of developing fibrosis, or both.

The method can, for example, comprise: administering to a subject in need thereof a composition comprising a cyclosporine analogue (e.g., CRV431), or a pharmaceutically acceptable salt, solvate, stereoisomer thereof. In some embodiments, the subject in need thereof is a subject at a risk of developing fibrosis. In some embodiments, the subject has not developed fibrosis. For example, the subject is an individual that is likely to, or will, develop, fibrosis in the absence of preventive measures (e.g., being treated with the fibrosis-preventing methods or fibrosis-preventing compositions disclosed herein). In some embodiments, the subject in need thereof is a subject suffering from fibrosis. In some embodiments, the subject in need thereof is a subject having one or more symptoms of fibrosis. In some embodiments, the subject in need thereof is a subject that has recently suffered from fibrosis.

For example, methods, compositions and kits disclosed herein can be used to prevent the onset of fibrosis in subjects at a risk of developing fibrosis (for example, subjects that have not developed fibrosis but are likely to, or will, develop fibrosis, in the absence of fibrosis prevention treatment). In addition, methods, compositions and kits disclosed herein can be used to delay the onset of fibrosis in subjects at a risk of developing fibrosis (for example, subjects that would have developed fibrosis at an earlier time, in the absence of fibrosis prevention treatment). As described herein, a subject at a risk of developing fibrosis is a subject who is not yet suffering from fibrosis, and thus there has been no fibrosis progression in the subject. In some embodiments, the onset of fibrosis is delayed. The delay can be, for example, one or more seconds, minutes, hours, days, weeks, months, or years. In some embodiments, the delay in the treated subject is relative to the same subject had he/she received no treatment. In some embodiments, the delay in the treated subject is relative to untreated subjects. In some embodiments, the onset of fibrosis is delayed by, or by about, 5, 10, 15, 20, 25, 30, 35, 40, 50, 75, 100, 150, 200, 250, 300, 350, or a range between any of these values, days. In some embodiments, the onset of fibrosis is delayed by, or by about, one, two, three, four, five, six, seven, eight, nine, ten, eleven, twelve, or a range between any of these values, months or years. In some embodiments, the onset of fibrosis is delayed by at least, or at least about, one, two, three, four, five, six, seven, eight, nine, ten, months or years. In some embodiments, the onset of fibrosis is delayed by at least, or at least about, one, two, three, four, five, six, seven, eight, nine, ten, or more hours.

In some embodiments, fibrosis (e.g., tissue fibrosis) is reversed in the subject. The reverse can be, or be about, 1%, 2%, 5%, 8%, 10%, 15%, 20%, 25%, 30%, 35%, 40%, 50%, 60%, 70%, 80%, 90%, 95%, or a range between any two of these values, of the existing fibrosis in the subject. In some embodiments, the reverse can be at least, or be at least about, 1%, 2%, 5%, 8%, 10%, 15%, 20%, 25%, 30%, 35%, 40%, 50%, 60%, 70%, 80%, 90%, 95%, or more of the existing fibrosis in the subject. The fibrosis is, in some embodiments, non-liver fibrosis.

In some embodiments, the amount of fibrosis (e.g., tissue fibrosis) is reduced in the subject. The reduction in the amount of fibrosis can be, or be about, 1%, 2%, 5%, 8%, 10%, 15%, 20%, 25%, 30%, 35%, 40%, 50%, 60%, 70%, 80%, 90%, 95%, or a range between any two of these values, in the subject. In some embodiments, the reduction in the amount of fibrosis can be at least, or be at least about, 1%, 2%, 5%, 8%, 10%, 15%, 20%, 25%, 30%, 35%, 40%, 50%, 60%, 70%, 80%, 90%, 95%, or more in the subject. The fibrosis is, in some embodiments, non-liver fibrosis.

In some embodiments, formation of fibrosis (e.g., tissue fibrosis) is reduced in the subject. The reduction in fibrosis formation can be, or be about, 1%, 2%, 5%, 8%, 10%, 15%, 20%, 25%, 30%, 35%, 40%, 50%, 60%, 70%, 80%, 90%, 95%, or a range between any two of these values, in the subject. In some embodiments, the reduction in fibrosis formation can be at least, or be at least about, 1%, 2%, 5%, 8%, 10%, 15%, 20%, 25%, 30%, 35%, 40%, 50%, 60%, 70%, 80%, 90%, 95%, or more in the subject. The fibrosis is, in some embodiments, non-liver fibrosis. The reduction in fibrosis formation the treated subject can be relative to the same subject had he/she received no treatment. In some embodiments, the reduction in fibrosis formation in the treated subject is relative to untreated subjects.

Therapeutic effectiveness of one or more of the cyclosporine analog (e.g., CRV431) or a pharmaceutically acceptable salt, solvate, stereoisomer thereof, disclosed herein, can be determined using methods known for measuring the amount of fibrosis (e.g., fibrosis in affected organ(s), tissue(s) or area(s)) in a subject. The subject can be, for example, a patient suffering from fibrosis or a patient recently suffered from fibrosis. The amount of fibrosis in the subject can be determined by methods known by one of skill in the art for determining the amount of fibrosis. For example, and without limitation, the amount of fibrosis can be determined by taking a muscle biopsy from the subject, sectioning the muscle onto slides and assessing the amount of fibrosis as revealed by staining techniques known in the art (e.g., Hematoxylin and Eosin (H&E) staining and/or Masson's trichrome staining). As another example, the amount of fibrosis can be determined in vivo by using magnetic resonance imaging (MRI).

An exemplary therapeutic endpoint that can be achieved by the compositions, methods or kits disclosed herein can be a reduction in the amount of fibrosis in a subject being administered with one or more the cyclosporine analogs (e.g., CRV431) disclosed herein or a pharmaceutically acceptable salt, solvate, stereoisomer thereof, and, optionally one or more additional therapeutic agents (e.g., antifibrotic agents). Relative amounts of fibrosis in the subject can be quantitated, for example, by tissue biopsy and subsequent histology, including but not limited by, by quantifying Evans blue dye uptake as a measure of myofiber or cellular damage (described for example in Heydemann et al., Neuromuscular Disorders 15 (9-10): 601-9 (2005), quantitation of hydroxyproline content as described in Swaggart et al., Physiol Genomics 43:24-31 (2011), or both. In some embodiments, the amount of fibrosis in the subject being administered with one or more the cyclosporine analogs (e.g., CRV431) disclosed herein, or a pharmaceutically acceptable salt, solvate, stereoisomer thereof and, optionally one or more additional therapeutic agents (e.g., antifibrotic agents), is reduced by, or reduced by about, 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 100%, or any value within 1% to 100%, or a range between any two of these values, as compared to a patient not so treated. In some embodiments, the amount of fibrosis in the subject being administered with one or more the cyclosporine analogs (e.g., CRV431) disclosed herein, or a pharmaceutically acceptable salt, solvate, stereoisomer thereof and, optionally one or more additional therapeutic agents (e.g., antifibrotic agents), is reduced by at least, or reduced by at least about, 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%, as compared to a patient not so treated.

Functional assays can be used to determine the effectiveness of the compounds disclosed herein in, for example, treating fibrosis, preventing fibrosis, reversing fibrosis, reducing the amount of fibrosis, delay the onset of fibrosis, reducing or inhibiting fibrosis formation, or any combination thereof. For example, the compounds can be tested in inhibiting collagen gel contraction as a measure of myofibroblast contractility; a characteristic function of myofibroblasts, which separates them from fibroblasts. Collagen gels were loaded with fibroblasts and contraction was measured after stimulation with TGF-β1. Effective compounds are expected to inhibit TGF-β1-induced contraction of collagen. The efficacy of the compounds can also be tested in inhibiting ECM protein production, which is one of the important characteristic functions of myofibroblasts.

Methods disclosed herein can be applicable to treat a subject having, for example, organ dysfunction, scarring, alteration of normal extracellular matrix balance, increase in collagen deposition, increased collagen volume fraction, differentiation of fibroblasts to myofibroblasts, reduction in the level of matrix metalloproteinases and increase in the level of tissue Inhibitors of matrix metalloproteinases, increased levels of either N-terminal or C-terminal propeptide of type I procollagen (PINP or PICP), decreased levels of C-terminal telepeptide of Type I collagen (CTP or CITP), increased collagen deposition and impaired cardiac function measured by various non-invasive imagining techniques, and impaired renal function as measured by increased proteinurea and albuminurea, decreased glomerular filtration rate or doubling of creatinine levels.

Therapeutic Agents

As used herein, the term "antifibrotic agent" refers to an agent (e.g., a chemical compound or a biologic) that has antifibrotic activity (for example, prevents, reduces or reverses fibrosis) in mammals. The antifibrotic agents can have different mechanisms of action, for example, some reducing the formation of collagen or another protein, and some enhancing the catabolismor removal of collagen in the affected area of the body. The antifibrotic agents having activity in the reduction of the presence of fibrotic tissue are included herein, without regard to the particular mechanism of action by which each such agent functions. Some non-limiting examples of antifibrotic are described in U.S. Pat. No. 5,720,950, which is incorporated herein by reference. Additional antifibrotic agents include, but are not limited to, Type II interferon receptor agonists (e.g., interferon-γ); pirfenidone and pirfenidone analogs; anti-angiogenic agents, such as VEGF antagonists, VEGF receptor antagonists, bFGF antagonists, bFGF receptor antagonists, TGF-β antagonists, TGF-β receptor antagonists; anti-inflammatory agents, IL-1 antagonists, such as IL-1Ra, angiotensin-converting-enzyme (ACE) inhibitors, angiotensin receptor blockers and aldosterone antagonists.

Antifibrotic agents, including cyclosporine analogues (e.g., CRV431) disclosed herein, or a pharmaceutically acceptable salt, solvate, stereoisomer thereof, can be used to treat fibrosis (e.g., an fibrotic disorder), or for primary prophylaxis or secondary prophylaxis of fibrosis (e.g., an fibrotic disorder) in a subject. The cyclosporine analogues, or a pharmaceutically acceptable salt, solvate, stereoisomer thereof, can, for example, delay the onset of fibrosis, in a subject (e.g., a subject at a risk of developing fibrosis). The cyclosporine analogues, or a pharmaceutically acceptable salt, solvate, stereoisomer thereof, can, for example, reverse fibrosis, in a subject. The cyclosporine analogues, or a pharmaceutically acceptable salt, solvate, stereoisomer thereof, can be used for reducing or inhibiting fibrosis formation in a subject. The cyclosporine analogues, or a pharmaceutically acceptable salt, solvate, stereoisomer thereof, can be used for reducing the amount of fibrosis in a subject. The fibrosis is, in some embodiments, non-liver fibrosis.

Cyclosporine analogues disclosed herein (e.g., CRV431), or a pharmaceutically acceptable salt, solvate, stereoisomer thereof, can prevent fibrosis (e.g., tissue fibrosis) from occurring. For example, these antifibrotic agents can prohibit fibrosis formation in the subject, delay the onset of fibrosis in the subject, or both. The delay can be, for example, one or more seconds, minutes, hours, days, weeks, months, or years. The delay in the treated subject can be relative to the same subject had he/she received no treatment, or relative to untreated subjects. In some embodiments, the onset of fibrosis is delayed by, or by about, 5, 10, 15, 20, 25, 30, 35, 40, 50, 75, 100, 150, 200, 250, 300, 350, or a range between any of these values, days. In some embodiments, the onset of fibrosis is delayed by, or by about, one, two, three, four, five, six, seven, eight, nine, ten, eleven, twelve, or a range between any of these values, months or years. In some embodiments, the onset of fibrosis is delayed by at least, or at least about, one, two, three, four, five, six, seven, eight, nine, ten, months or years. In some embodiments, the onset of fibrosis is delayed by at least, or at least about, one, two, three, four, five, six, seven, eight, nine, ten, or more hours.

Cyclosporine analogues disclosed herein (e.g., CRV431), or a pharmaceutically acceptable salt, solvate, stereoisomer thereof, can reverse fibrosis (e.g., tissue fibrosis) in the subject. The reverse can be, or be about, 1%, 2%, 5%, 8%, 10%, 15%, 20%, 25%, 30%, 35%, 40%, 50%, 60%, 70%, 80%, 90%, 95%, or a range between any two of these values, of the existing fibrosis in the subject. In some embodiments, the reverse can be at least, or be at least about, 1%, 2%, 5%, 8%, 10%, 15%, 20%, 25%, 30%, 35%, 40%, 50%, 60%, 70%, 80%, 90%, 95%, or more of the existing fibrosis in the subject.

Cyclosporine analogues disclosed herein (e.g., CRV431), or a pharmaceutically acceptable salt, solvate, stereoisomer thereof, can reduce the amount of fibrosis (e.g., tissue fibrosis) in the subject. The reduction in the amount fibrosis can be, or be about, 1%, 2%, 5%, 8%, 10%, 15%, 20%, 25%, 30%, 35%, 40%, 50%, 60%, 70%, 80%, 90%, 95%, or a range between any two of these values, in the subject. In some embodiments, the reduction in the amount of fibrosis can be at least, or be at least about, 1%, 2%, 5%, 8%, 10%, 15%, 20%, 25%, 30%, 35%, 40%, 50%, 60%, 70%, 80%, 90%, 95%, or more in the subject. The fibrosis is, in some embodiments, non-liver fibrosis.

Cyclosporine analogues disclosed herein (e.g., CRV431), or a pharmaceutically acceptable salt, solvate, stereoisomer thereof, can reduce formation of fibrosis (e.g., tissue fibrosis) in the subject. The reduction in fibrosis formation can be, or be about, 1%, 2%, 5%, 8%, 10%, 15%, 20%, 25%, 30%, 35%, 40%, 50%, 60%, 70%, 80%, 90%, 95%, or a range between any two of these values, in the subject. In some embodiments, the reduction in fibrosis formation can be at least, or be at least about, 1%, 2%, 5%, 8%, 10%, 15%, 20%, 25%, 30%, 35%, 40%, 50%, 60%, 70%, 80%, 90%, 95%, or more in the subject. The fibrosis is, in some embodiments, non-liver fibrosis. The reduction in fibrosis formation the treated subject can be relative to the same subject had he/she received no treatment, or relative to untreated subjects.

In some embodiments, a cyclosporine analogue is a compound of Formula L:

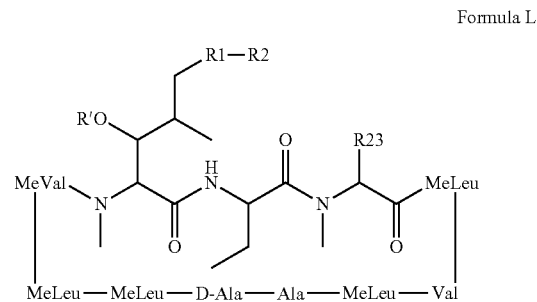

Formula L wherein:
a. R' is H or acetyl;
b R1 is a saturated or unsaturated straight or branched aliphatic carbon chain from 2 to 15 carbon atoms in length;
c. R2 is selected from the group consisting of:
i. H;
ii. an unsubstituted, N-substituted, or N,N-disubstituted amide;
iii. a N-substituted or unsubstituted acyl protected amine;
iv. a N-substituted or unsubstituted amine;
v. a carboxylic acid;
vi. a nitrile;
vii. an ester;
viii. a ketone;
ix. a hydroxy, dihydroxy, trihydroxy, or polyhydroxy alkyl; and
x. a substituted or unsubstituted aryl;
xi. a saturated or unsaturated. straight or branched aliphatic chain optionally containing a substituent selected from the group consisting of a hydrogen, a ketone, a hydroxyl, a nitrile, a carboxylic acid, an ester, a 1,3-dioxolane, a halogen, and an oxo;
xii. an aromatic group containing a substituent selected from the group consisting of a halogen, an ester, and a nitro; and
xiii. a combination of the saturated or unsaturated, straight or branched aliphatic chain of (xi) and the aromatic group of (xii); and
d. R23 is a saturated or unsaturated straight chain or branched optionally substituted aliphatic carbon chain.

In some embodiments, R1-R2 is selected from the group consisting of:

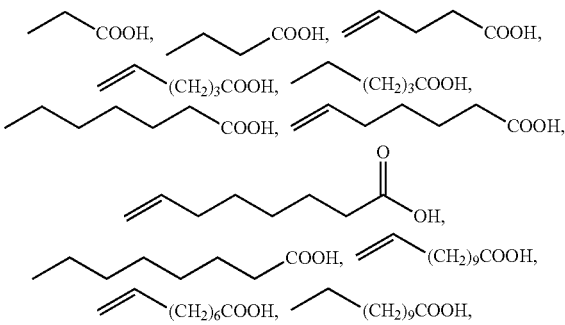

-continued
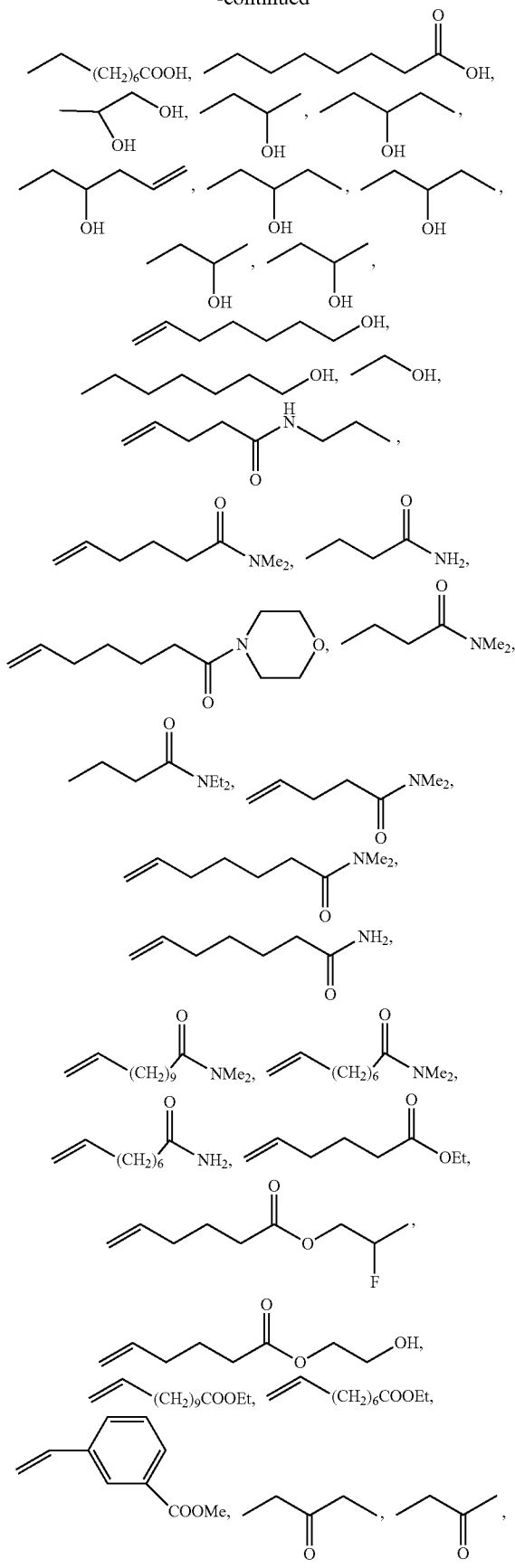
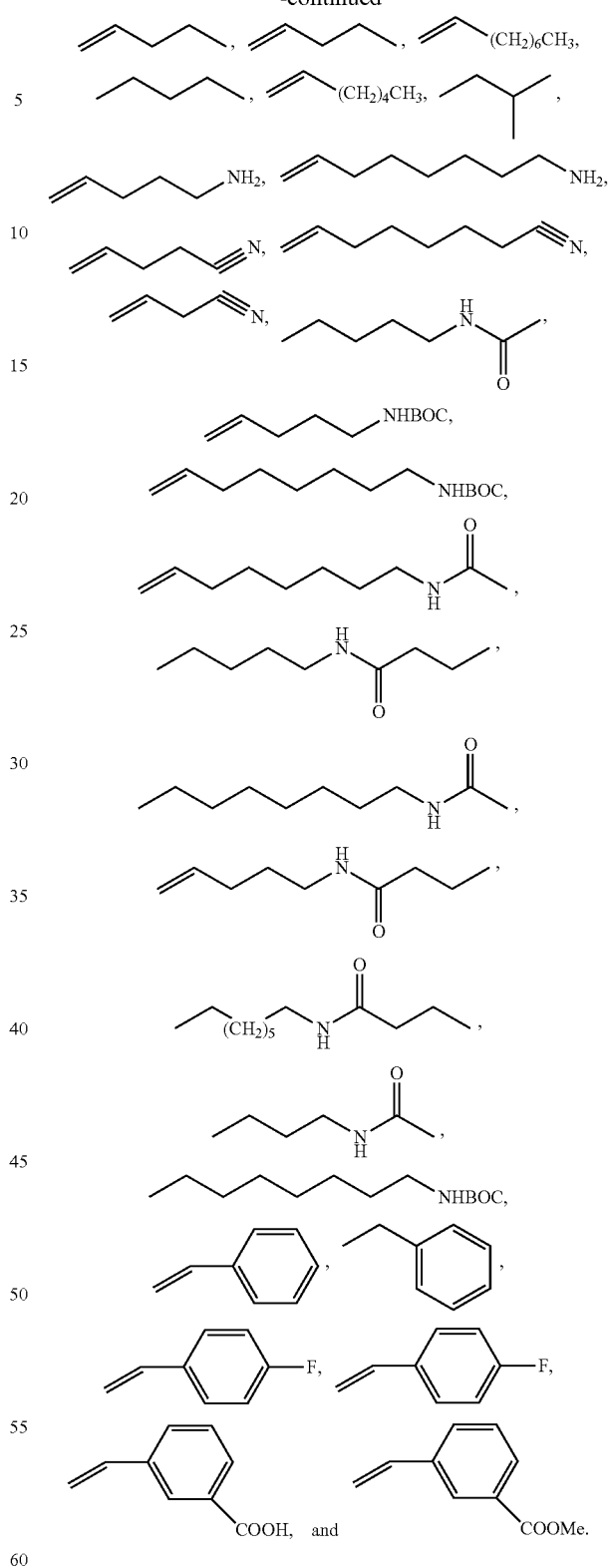
In some embodiments, R1-R2 comprises a saturated or unsaturated. straight or branched aliphatic chain of between 2 and 5 carbons optionally substituted with a substituent selected from the group consisting of a hydrogen, a ketone, a hydroxyl, a nitrile, a halogen, an oxo, a carboxylic acid, an ester, and an 1,3-dioxolane.

In some embodiments, R2 is selected from the group consisting of

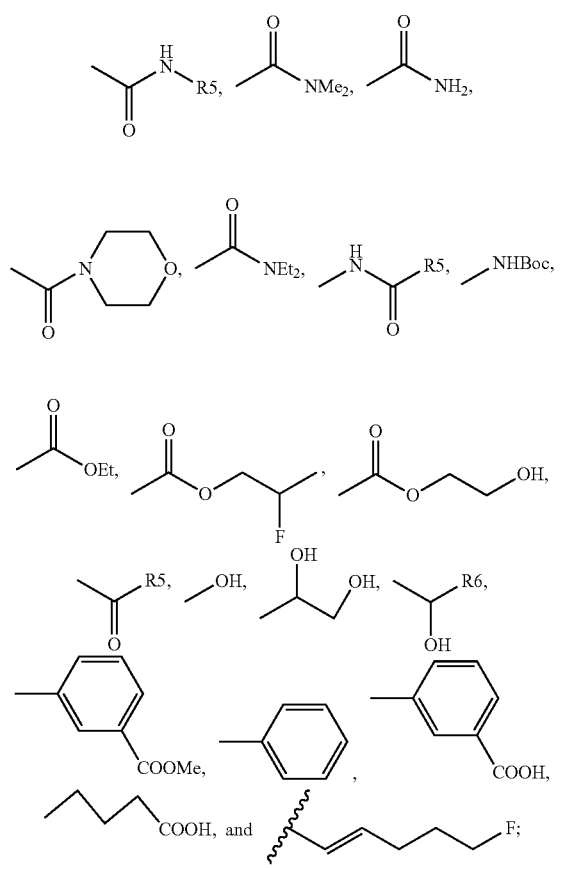

R5 is a saturated or unsaturated straight or branched aliphatic carbon chain between 1 and 10 carbons in length; and R6 is a monohydroxylated, dihydroxylated, trihydroxylated or polyhydroxylated saturated or unsaturated straight chain or branched aliphatic carbon chain between 1 and 10 carbons in length.

In some embodiments, R23 is selected from the group consisting of: —$CH_3$, —$CH_2CH_3$, —$CH_2CHCH_2$, —$CH_2CH_2CH_2I$, —$(CH_2)_3CH_2I$, —$(CH_2)_3N^+(CH_3)_3$, —$CH_2CCH$, —$CH_2CO_2(t\text{-}Bu)$, —$CH_2Ph$, —$CH_2OH$, —$CH(OH)CH_3$, —$CH(OH)(t\text{-}Bu)$, —$CH(OH)Ph$, —COOH, —$SCH_3$, and —S(p-Tol) In some embodiments, R23 comprises an optionally substituted alkyl, including optionally substituted C1-C3 alkyl. The alkyl can be substituted with amino and may comprise a C1-C3-Ala, wherein the compound comprises the D-epimer of amino acid 3 which is the amino acid to which R23 is attached. In some embodiments, R23 can be MeAla. In some embodiments, R23 is a straight or branched aliphatic carbon chain of 1 to 6, 1 to 5, 1 to 4, 1 to 3 or 2 carbons in length.

In some embodiments,

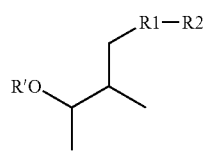

in Formula L is selected from the group consisting of:

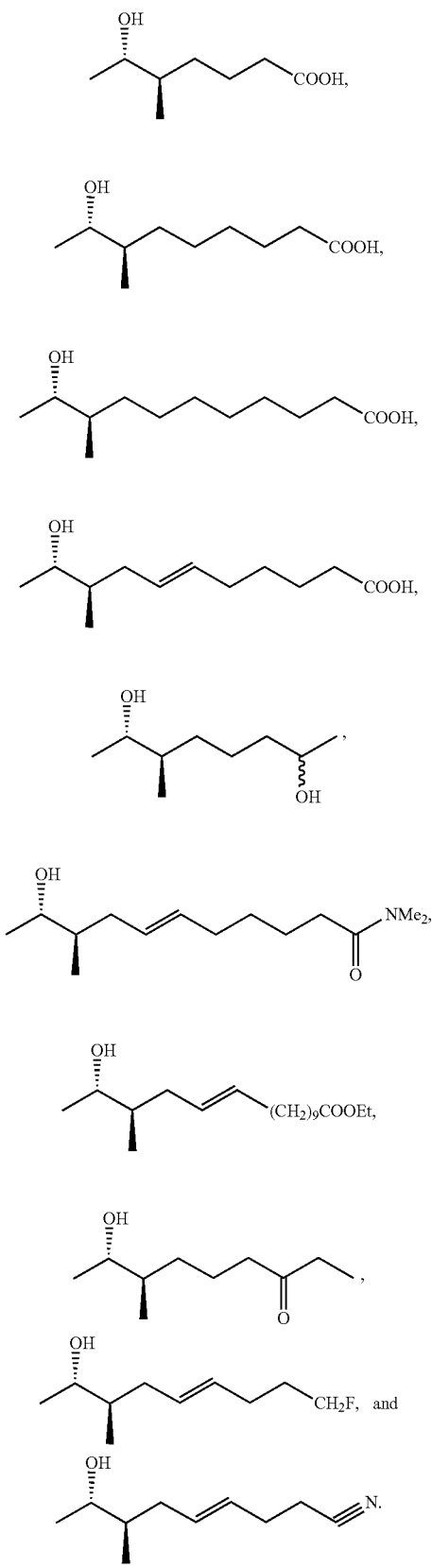

In some embodiments, a cyclosporine analogue is a compound of Formula L:

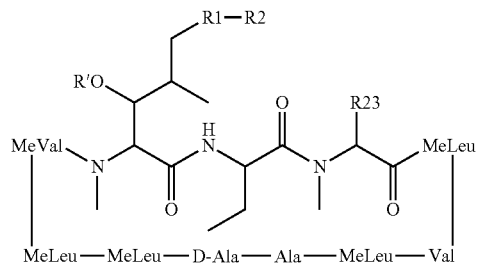

Formula L wherein:
a. R' is H or acetyl;
b. R1 is a saturated or unsaturated straight or branched aliphatic carbon chain from 2 to 15 carbon atoms in length;
c. R2 is selected from the group consisting of:
  i. an unsubstituted, N-substituted, or N,N-disubstituted amide;
  ii. a carboxylic acid;
  iii. a nitrile;
  iv. an ester;
  v. a ketone;
  vi. a hydroxy, dihydroxy, trihydroxy, or polyhydroxy alkyl;
  vii. a substituted or unsubstituted aryl;
  viii. a saturated or unsaturated straight or branched aliphatic carbon chain substituted with a substituent selected from the group consisting of a ketone, a hydroxy, a nitrile, a carboxylic acid, an ester, a 1,3-dioxolane, and an oxo;
  ix. an aromatic group substituted with a substituent selected from the group consisting of a halogen, an ester, and a nitro; and
  x. a combination of the saturated or unsaturated straight or branched aliphatic carbon chain of viii) and the aromatic group of ix); and
d. R23 is unsubstituted $C_1$-$C_3$ alkyl.

In some embodiments, R' is H.

In some embodiments, R1 is a saturated or unsaturated straight or branched aliphatic carbon chain from 5 to 8 carbon atoms in length.

In some embodiments, R2 is selected from the group consisting of:

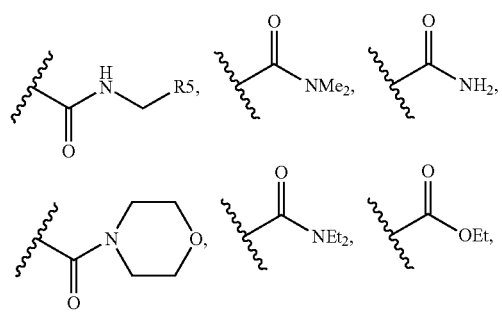

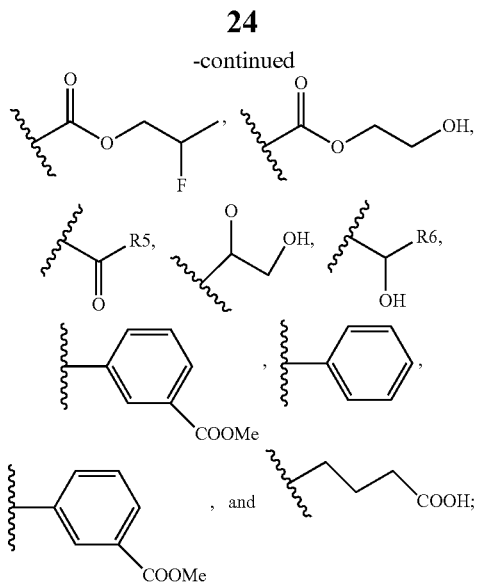

R5 is a saturated or unsaturated straight or branched aliphatic carbon chain between 1 and 10 carbons in length; and R6 is a monohydroxylated, dihydroxylated, trihydroxylated, or polyhydroxylated saturated or unsaturated straight or branched aliphatic carbon chain between 1 and 10 carbons in length.

In some embodiments, R1-R2 is selected from the group consisting of:

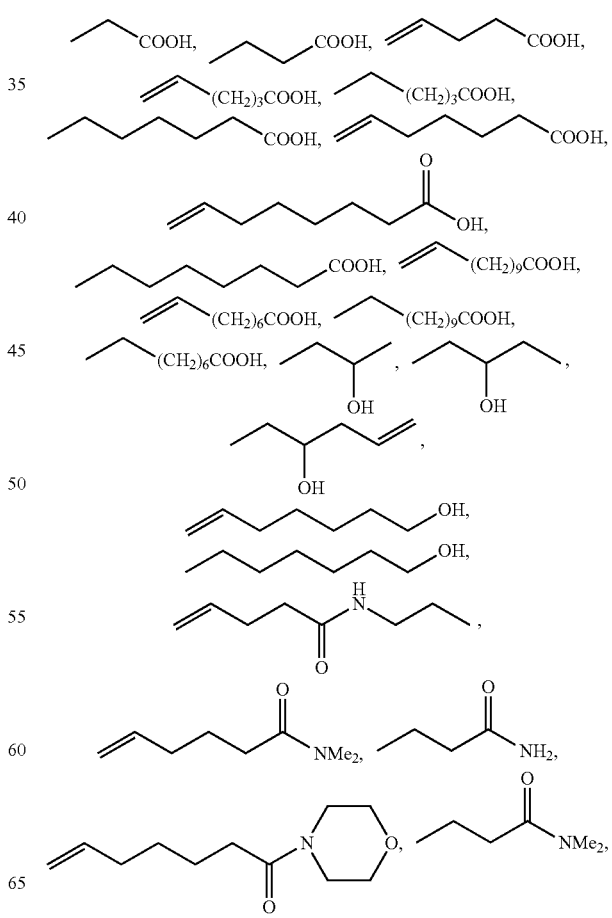

-continued

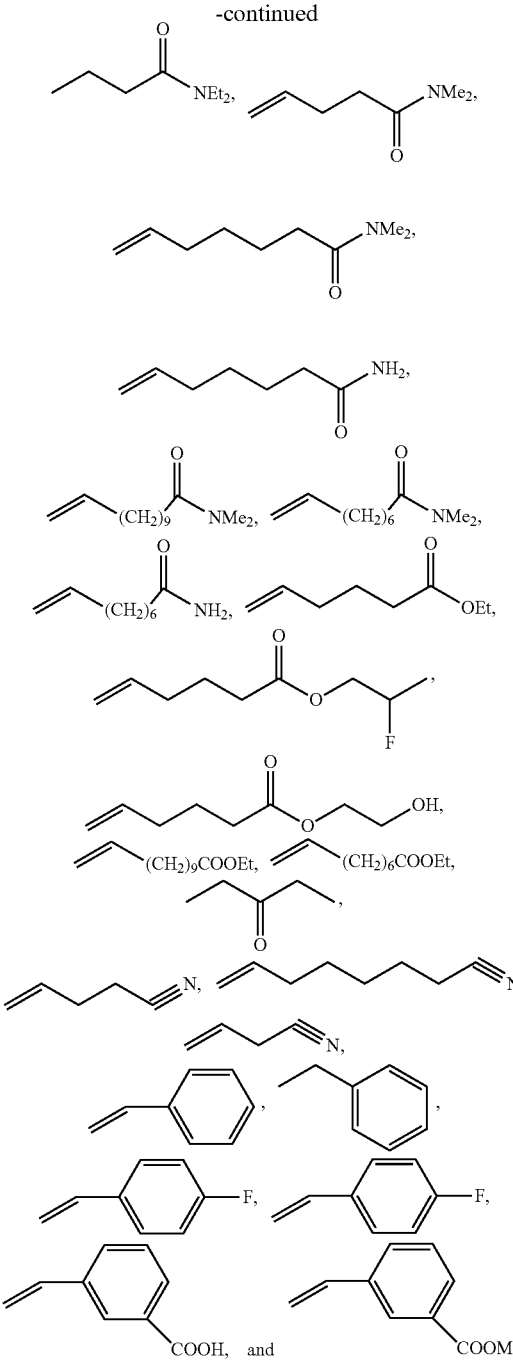

In some embodiments, R1-R2 is substituted with a substituent selected from the group consisting of a ketone, a hydroxy, a nitrile, an oxo, a carboxylic acid, an ester, and a 1,3-dioxolane. In some embodiments, R1-R2 is at least 6 carbon atoms in length.

In some embodiments,

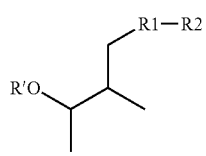

in Formula L is selected from the group consisting of:

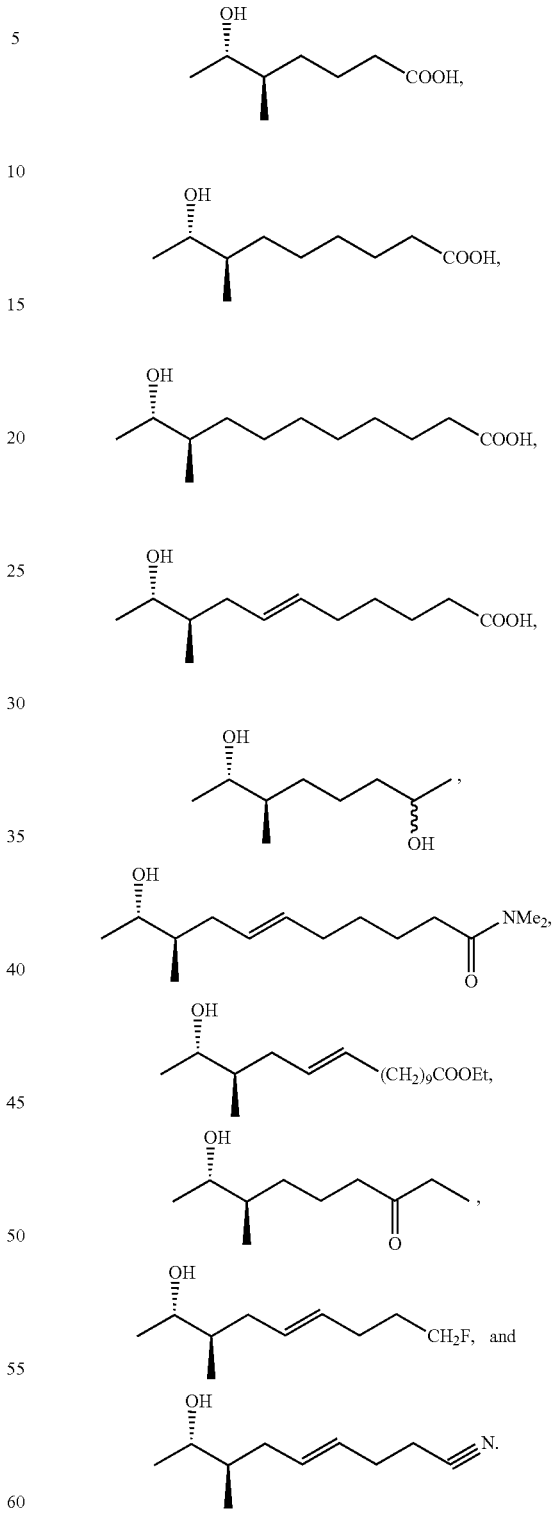

In some embodiments, R23 is selected from the group consisting of: —CH$_3$ and —CH$_2$CH$_3$. In some embodiments, R23 is methyl. In some embodiments, the compound comprises the D-epimer of amino acid 3 which is the amino acid to which R23 is attached.

In some embodiments, a cyclosporine analogue is a compound selected from the group consisting of:

| | | R23 | Isomer |
|---|---|---|---|
| a) | R∼∼COOH | —CH₃ | L |
| b) | R∼∼COOH | —CH₃ | D |
| c) | R∼∼∼COOH | —CH₃ | L |
| d) | R∼∼∼COOH | —CH₂CH₃ | D |
| e) | R∼∼∼COOH | —CH₃ | D |
| f) | R∼∼∼∼COOH | —CH₃ | L |
| g) | R∼∼∼∼COOH | —CH₂CH₃ | D |
| h) | R∼∼CN | —CH₃ | D |
| i) | R∼∼CN | —CH₂CH₃ | L |
| j) | R∼∼CN | —CH₂CH₃ | D |
| k) | R∼∼C(O)∼ | —CH₃ | L |
| l) | R∼∼C(O)∼ | —CH₃ | D |
| m) | R∼COOH | —CH₃ | D |
| n) | R∼COOH | —CH₂CH₃ | D |
| o) | R∼(CH₂)₉COOH | —CH₃ | D |
| r) | R∼∼∼COOH | —CH₃ | D |
| s) | R∼∼∼COOH | —CH₃ | L |
| t) | R∼phenyl | —CH₃ | D |
| u) | R∼∼CH(OH)CH₃ | —CH₃ | D |
| v) | R∼∼CH(OH)CH₃ | —CH₃ | L |
| w) | R∼=∼(CH₂)₉COOH | —CH₂CH₃ | L |
| x) | R∼=∼COOH | —SCH₃ | D/L |

-continued

| | | R23 | Isomer |
|---|---|---|---|
| z) | R∼∼COOH | —(CH$_2$)$_3$N$^+$(CH$_3$)$_3$ | D/L |
| aa) | R∼∼C(O)NEt$_2$ | —CH$_2$—C$_6$H$_5$ | D |
| bb) | R∼∼ (diene) | —CH$_3$ | D |
| cc) | R∼∼C(O)NMe$_2$ | —CH$_3$ | L |
| dd) | R∼∼C(O)-morpholine | —CH$_3$ | L |
| ee) | R∼∼∼∼∼C(O)NMe$_2$ | —CH$_3$ | D |
| ff) | R∼∼∼∼∼C(O)NMe$_2$ | —CH$_2$CH$_3$ | D |
| gg) | R∼(CH$_2$)$_9$C(O)NMe$_2$ | —CH$_3$ | D |
| hh) | R∼∼COOMe | —CH$_3$ | D |
| ii) | R∼∼COOMe | —CH$_2$CH$_3$ | D |
| jj) | R∼(CH$_2$)$_9$COOEt | —CH$_3$ | D | wherein:
R is

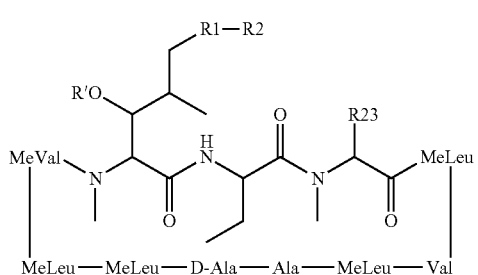

R' is H or acetyl; and
the isomer is the isomeric form of amino acid 3 which is the amino acid to which R23 is attached.

In some embodiments, a cyclosporine analogue is a compound of Formula L:

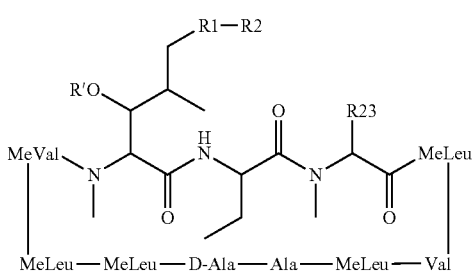

wherein:
a. R' is H or acetyl;
b. R1 is a saturated or unsaturated straight or branched aliphatic carbon chain from 2 to 15 carbon atoms in length;

c. R2 is selected from the group consisting of:
   i. an unsubstituted, N-substituted, or N,N-disubstituted amide;
   ii. a carboxylic acid;
   iii. a nitrile;
   iv. an ester;
   v. a ketone;
   vi. a hydroxy, dihydroxy, trihydroxy, or polyhydroxy alkyl;
   vii. a substituted or unsubstituted aryl;
   viii. a saturated or unsaturated straight or branched aliphatic carbon chain substituted with a substituent selected from the group consisting of a ketone, a hydroxy, a nitrile, a carboxylic acid, an ester, a 1,3-dioxolane, and an oxo;
   ix. an aromatic group substituted with a substituent selected from the group consisting of a halogen, an ester, and a nitro; and
   x. a combination of the saturated or unsaturated straight or branched aliphatic carbon chain of (viii) and the aromatic group of (ix); and
d. R23 is a saturated or unsaturated straight or branched optionally substituted aliphatic carbon chain,
wherein R1-R2 is at least 6 carbon atoms in length.

In some embodiments, R' is H.

In some embodiments, R1 is a saturated or unsaturated straight or branched aliphatic carbon chain from 5 to 8 carbon atoms in length.

In some embodiments, R1-R2 is selected from the group consisting of:

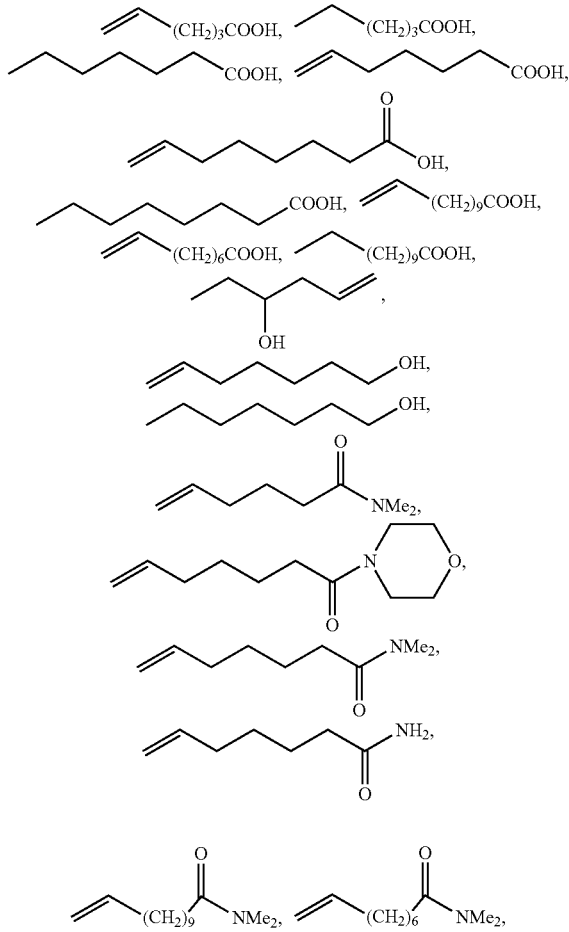

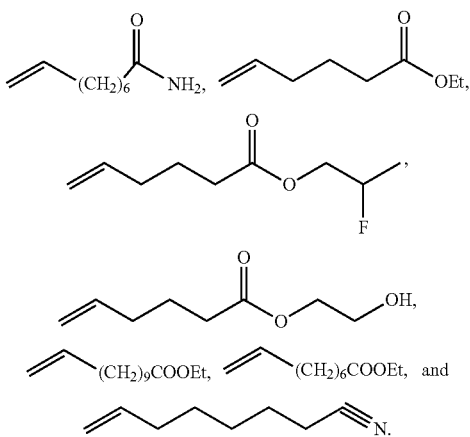

In some embodiments, R1-R2 is substituted with a substituent selected from the group consisting of a ketone, a hydroxy, a nitrile, an oxo, a carboxylic acid, an ester, and a 1,3-dioxolane.

In some embodiments, R23 is selected from the group consisting of: CH$_3$, —CH$_2$CH$_3$, —CH$_2$CHCH$_2$, —CH$_2$CH$_2$CH$_2$I, —(CH$_2$)$_3$CH$_2$I, —(CH)$_3$N$^+$(CH$_3$)$_3$— CH$_2$CCH, —CH$_2$CO$_2$(t-Bu), —CH$_2$Ph-CH$_2$OH, —CH(OH)CH$_3$, —CH(OH)(t-Bu), —CH(OH)Ph, —COOH, —SCH$_3$ and S (p-Tol). In some embodiments, R23 comprises an optionally substituted C$_1$-C$_3$ alkyl. In some embodiments, R23 is substituted with amino. In some embodiments, R23 is C$_1$-C$_3$ alkyl and the compound comprises the D-epimer of amino acid 3 which is the amino acid to which R23 is attached. In some embodiments, R23 is methyl. In some embodiments, R23 is a straight or branched aliphatic carbon chain of 1 to 6 carbons in length.

In some embodiments,

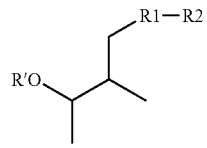

in Formula L is selected from the group consisting of:

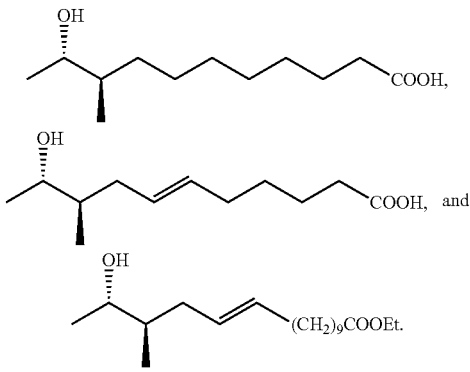

In some embodiments, R1-R2 is

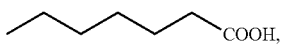

R23 is methyl, and the compound is a D-epimer of amino acid 3 which is the amino acid to which R23 is attached.

In some embodiments, a cyclosporine analogue is a compound of Formula L:

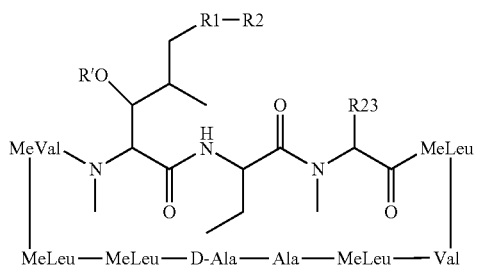

Formula L wherein:
R' is H or acetyl;
R1 is a saturated or unsaturated straight chain or branched aliphatic carbon chain from 2 to 15 carbon atoms in length;
R2 is a N-substituted or unsubstituted acyl protected amine; and
R23 is methyl or ethyl.

In some embodiments, R' is H.

In some embodiments, R1 is a saturated or unsaturated straight or branched aliphatic carbon chain from 5 to 8 carbon atoms in length.

In some embodiments, R2 is

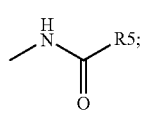

wherein R5 is a saturated or unsaturated straight or branched aliphatic carbon chain between 1 and 10 carbons in length.

In some embodiments, R1-R2 is selected from the group consisting of:

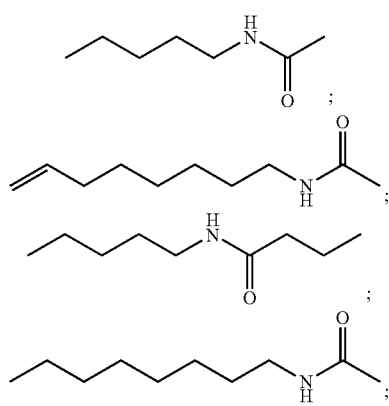

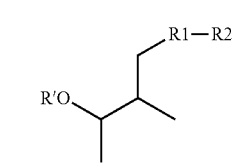

In some embodiments, R23 is methyl.

In some embodiments,

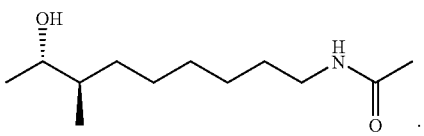

in formula L is

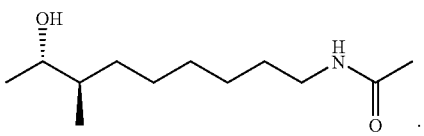

In some embodiments, R', R1-R2, and R23 and the isomer of said compound are selected from the following:

| R' | R1-R2 | R23 | Isomer |
|---|---|---|---|
| H | ![structure] | —CH₃ | D |
| H | ![structure] | —CH₂CH₃ | L |
| H | ![structure] | —CH₂CH₃ | D | wherein the isomer is the isomeric form of amino acid 3 which is the amino acid to which R23 is attached.

In some embodiments, a cyclosporine analogue is a compound of Formula L:

Formula L

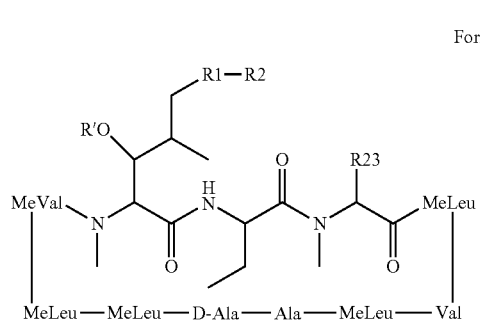

wherein:
R' is H or acetyl;
R1-R2 is selected from the group consisting of:

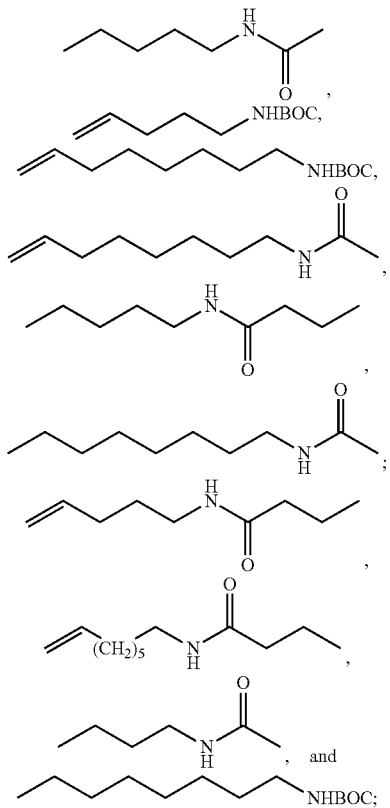

and
R23 is a saturated or unsaturated straight chain or branched optionally substituted aliphatic carbon chain.

In some embodiments, R' is H.
In some embodiments, R1-R2 is

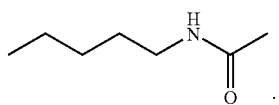

In some embodiments,

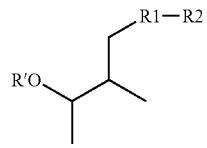

in Formula L is

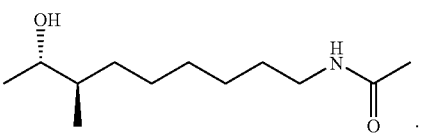

In some embodiments, R23 is selected from the group consisting of: —CH$_3$, —CH$_2$CH$_3$, —CH$_2$CHCH$_2$, —CH$_2$CH$_2$CH$_2$I, —(CH$_2$)$_3$CH$_2$I, —(CH$_2$)$_3$N$^+$(CH$_3$)$_3$, —CH$_2$CCH, —CH$_2$CO$_2$(t-Bu), —CH$_2$Ph-CH$_2$OH, —CH(OH)CH$_3$, —CH(OH)(t-Bu), —CH(OH)Ph, —COOH, —SCH$_3$, and —S(p-Tol). In some embodiments, R23 is —CH$_3$ or —CH$_2$CH$_3$. In some embodiments, R23 is CH$_3$. In some embodiments, R23 (a) comprises an optionally substituted C$_1$-C$_3$ alkyl; (b) is substituted with an amino; (c) is a C$_1$-C$_3$-Ala and said compound comprises the D-epimer; (d) is MeAla; and/or (e) is a straight or branched aliphatic carbon chain of 1 to 6, 1 to 5, 1 to 4, 1 to 3 or 2 carbons in length.

In some embodiments, R', R1-R2 and R23 and the isomer of said compound are selected from the following:

| R' | R1-R2 | R23 | Isomer |
|---|---|---|---|
| H |  | —CH$_3$ | D |
| H |  | —CH$_2$CH$_3$ | L |
| H |  | —CH$_2$CH$_3$ | D |

In some embodiments, the cyclosporine analogue is a small molecule cyclophilin inhibitor CRV431 (shown below) which is a derivative of cyclosporine A (CsA), a neutral cyclic peptide consisting of eleven amino acids, wherein amino acids 1 and 3 have been chemically modified.

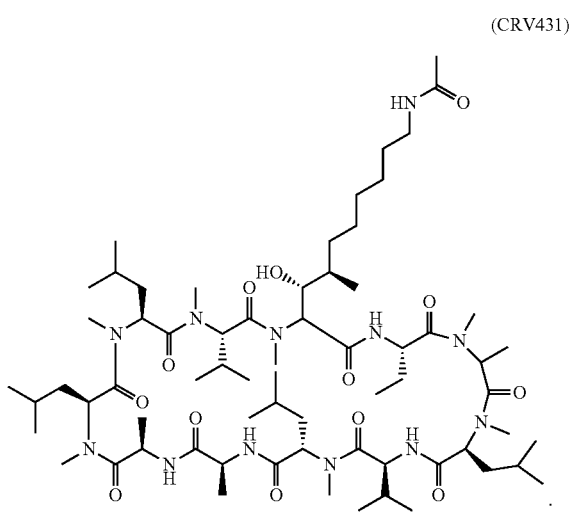 [SMILES: CC[C@@H]1NC(=O)C([C@H](O)[C@H](C)CCCCCCNC(C)=O)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@H](C(C)C)NC(=O)[C@H](CC(C)C)N(C)C(=O)C(C)N(C)C1=O]

(CRV431)

CRV431 is a small molecule cyclophilin inhibitor under clinical development for the treatment of liver diseases including liver fibrosis and hepatocellular carcinoma. In preclinical studies, CRV431 shows anti-viral activity against a number of viruses including hepatitis B, hepatitis C, and HIV and anti-fibrotic activity in the liver in a number of in vivo models. CRV431 can reduce liver fibrosis arising from non-alcoholic steatohepatitis ("NASH") and hepatocellular carcinoma tumor burden in experimental models of NASH.

As disclosed herein, including in vitro studies, CRV431 can decrease production of the extracellular matrix (ECM) molecules, collagen and fibronectin, from fibroblastic cells derived from various different organs. Collagen and fibronectin over-production from these types of cells cause fibrotic scarring of injured organs, and CRV431 can decrease collagen and fibronectin production from multiple cell types. These results demonstrate that derivatives of CsA, such as CRV431, can exert anti-fibrotic activity across a range of diseases and a range of cells, tissues and organs.

For example, as described herein, CRV431 can decrease production of the extracellular matrix (ECM) molecules, collagen and fibronectin, from fibroblastic cells derived from five cell types, including lung fibroblasts from a patient with idiopathic pulmonary fibrosis ("IPF"), cardiac fibroblasts, dermal (skin) fibroblasts, renal mesangial cells, and the LX2 hepatic stellate cell line. It is known that IPF is an aggressive fibrotic disease in tremendous need of new treatments. As described herein, CRV431 dose-dependently decreased procollagen and fibronectin secretion from all cell types with similar magnitude, as measured by enzyme-linked immunosorbent assay (ELISA). The extent of inhibition was similar whether or not the cells were stimulated with the profibrotic agent, transforming growth factor-beta (TGFβ), consistent with direct effects on ECM synthesis. CRV431 dose-dependently decreased ECM production by up to 55% at clinically relevant concentrations, without causing any reduction in cell viability. As disclosed herein, CRV431 can be used to reduce ECM production by inhibiting cyclophilin B, and consistent with this observation, downregulation of cyclophilin B with small interfering RNA (siRNA) similarly decreased procollagen and fibronectin secretion.

Fibrotic scarring is a major pathological feature and driver of organ dysfunction in many diseases, including liver cirrhosis, IPF, chronic kidney disease, and several heart conditions. Yet, there are very few treatments available that attenuate the scarring. Most treatments attempt to reduce fibrosis by targeting the stimulation of fibroblastic cells, but these signaling events may vary by patient, type of fibrotic disease, or disease stage. Without being limited to any particular theory, it is advantageous to use CRV431 for the treatment of fibrotic diseases (in liver as well as in organs other than liver) since in some embodiments, the effects of CRV431 is independent of the type of stimulatory signal.

In some embodiments, the method can comprise administering to the subject in need thereof one or more additional therapeutic agents. For example, the composition can comprise one or more additional antifibrotic agents. Non-limiting examples of antifibrotic agents include Type II interferon receptor agonists (e.g., interferon-γ); pirfenidone and pirfenidone analogs; nintedanib and nintedanib analogs, anti-angiogenic agents, such as VEGF antagonists, VEGF receptor antagonists, bFGF antagonists, bFGF receptor antagonists, TGF-β antagonists, TGF-β receptor antagonists; anti-inflammatory agents, IL-1 antagonists, such as IL-1Ra, angiotensin-converting-enzyme (ACE) inhibitors, angiotensin receptor blockers and aldosterone antagonists, mitomycin C (MMC), 5-fluorouracil (5-FU), adenylyl cyclase activators, β-adenoreceptor agonists, flavonoids, mast cell stabilizers, phosphodiesterase inhibitors and procyanidins, and any combination thereof.

In some embodiments, the additional therapeutic agent(s) (e.g., additional antifibrotic agent(s)) is co-administered to the subject with the composition comprising one or more of the cyclosporine analogues (e.g., CRV431) disclosed herein, or a pharmaceutically acceptable salt, solvate, stereoisomer thereof. In some embodiments, the additional therapeutic agents is administered to the subject before the administration of the composition comprising one or more of the cyclosporine analogues (e.g., CRV431) disclosed herein, or a pharmaceutically acceptable salt, solvate, stereoisomer thereof, and/or after the administration of the composition comprising one or more of the cyclosporine analogues (e.g., CRV431) disclosed herein, or a pharmaceutically acceptable salt, solvate, stereoisomer thereof.

Kits, Compositions and Methods of Administration

Provided in some embodiments include kits comprising: a cyclosporine analogue (e.g., CRV431) or a pharmaceutically acceptable salt, solvate, stereoisomer thereof, and a label indicating the use of the kit. In some embodiments, the label indicates that the kit is for preventing fibrosis, for example a fibrotic disorder, in a subject. In some embodiments, the label indicates that the kit is for treating fibrosis, for example a fibrotic disorder, in a subject. In some embodiments, the label indicates that the kit is for reducing the amount of fibrosis in a subject. In some embodiments, the label indicates that the kit is for delaying the onset of fibrosis in a subject. In some embodiments, the label indicates that the kit is for reducing or inhibiting fibrosis formation, in a subject. In some embodiments, the label indicates that the kit is for reversing fibrosis in a subject.

Also provided herein, in some embodiments, are compositions comprising: one or more of the cyclosporine analogues disclosed herein (e.g., CRV431), or a pharmaceutically acceptable salt, solvate, stereoisomer thereof, for use in preventing fibrosis (e.g., a fibrotic disorder), treating fibrosis (e.g., a fibrotic disorder), reducing the amount of fibrosis, delaying the onset of fibrosis, reducing or inhibiting fibrosis formation, reversing fibrosis, or any combination thereof.

Fibrosis can be fibrosis affecting the heart, liver, lung, skeletal muscle, kidney, eyes, blood vessel, skin, brain, bone marrow, gastrointestinal tract, peritoneum, vasculature, or any combination thereof. In some embodiments, the fibrosis is non-liver fibrosis. The fibrotic disorder can be any of the fibrotic disorders disclosed herein, including but not limited to retinal fibrosis, corneal fibrosis, conjunctival fibrosis, fibrosis of the trabecular meshwork, renal fibrosis, pulmonary fibrosis, idiopathic pulmonary fibrosis (IPF), usual interstitial pneumonitis (UIP), interstitial lung disease (ILD), cryptogenic fibrosing alveolitis (CFA), bronchiolitis obliterans, bronchiectasis, cirrhosis, hepatic fibrosis, fibrotic vascular disease, cystic fibrosis, pulmonary fibrosis, idiopathic pulmonary fibrosis, musculoskeletal fibrosis, renal fibrotic disease, lymph node fibrosis associated with HIV, inflammatory pulmonary fibrosis, pancreatic fibrosis, cardiac fibrosis, vascular fibrosis, myocardiac fibrosis, or a combination thereof.

In some embodiments, the composition is a stable self-microemulsifying drug delivery systems ("SMEDDS") formulation comprising a derivative or an analog, of cyclosporine A (e.g., CRV431), or a pharmaceutically acceptable salt, solvate, stereoisomer thereof. The composition can, for example, enables good solubility of a derivative of cyclosporine A (e.g., CRV431), or a pharmaceutically acceptable salt, solvate, stereoisomer thereof, and enables significant blood exposure in humans. In some embodiments, the composition further comprises polyoxyl castor oil (also known as polyoxyl 40 hydrogenated castor oil, macrogolglycerol hydroxystearate, and PEG-40 hydrogenated castor oil, such as Cremophor® RH40 and Kolliphor® RH40). In some embodiments, the composition comprises ethanol. In some embodiments, the composition comprises diethylene glycol monoethyl ether (also known as 2-(2-Ethoxyethoxy) ethanol, such as Transcutol®). In some embodiments, the composition comprises propylene glycol (PG). In some embodiments, the composition comprises glyceryl monolinoleate, such as Maisine® CC. In some embodiments, the composition comprises Vitamin E. Various pharmaceutical compositions/drug delivery system (e.g., SMEDDS formulations) comprising cyclosporine analogues (e.g., CRV431) or pharmaceutically acceptable salts thereof, have been described in PCT patent application published as WO 2020/112562, the content of which is incorporated herein by reference in its entirety.

In some embodiments, the system comprises Vitamin E, Maisine® CC, propylene glycol, Transcutol®, ethanol, and Cremophor® RH40 at a weight ratio of 1/1/5/5/2.4/4 or 1/1.5/2.5/5/2.4/5. The system can, for example, comprise the cyclosporine analogue (e.g., CRV431) at a concentration of from about 10 mg/mL to about 90 mg/mL, including 10 mg/mL, 20 mg/mL, 30 mg/mL, 40 mg/mL, 50 mg/mL, 60 mg/mL, 70 mg/mL, 80 mg/mL, 90 mg/mL, a range between any two of these values, or any value within 10 mg/mL to 90 mg/mL. In some embodiments, the system comprises the cyclosporine analogue (e.g., CRV431) at a concentration of about 90 mg/mL. In some embodiments, the system comprises the cyclosporine analogue (e.g., CRV431) at a concentration of, or of about, 70 mg/mL.

The composition can be, for example, a pharmaceutical composition comprising a cyclosporine analogue (e.g., CRV431), or a pharmaceutically acceptable salt, solvate, stereoisomer thereof, and one or more pharmaceutically acceptable excipients. In some embodiments, the composition is administered to the subject by intravenous administration, nasal administration, pulmonary administration, oral administration, or parenteral administration. In some embodiments, the composition is in the form of powder, pill, tablet, microtablet, pellet, micropellet, capsule, capsule containing microtablets, liquid, aerosols, suspension, or nanoparticles. In some embodiments, the composition is administered to the subject once, twice, or three times a day. In some embodiments, the composition is administered to the subject once or twice in an emergency situation (e.g., in an ongoing surgery). In some embodiments, the composition is administered to the subject over the course of at least a day, at least two days, at least three days, at least a week, or more. In some embodiments, the composition is administered to the subject at an effective daily dose of the cyclosporine analogue (e.g., CRV431) or a pharmaceutically acceptable salt, solvate, stereoisomer thereof at from 10 mg to 250 mg.

The therapeutically effective amount and the frequency of administration of, and the length of treatment with, the cyclosporine analogue (e.g., CRV431) may depend on various factors, including the nature and the severity of the proliferative disease such as cancer, the potency of the cyclosporine analogue (e.g., CRV431), the mode of administration, the age, the body weight, the general health, the gender and the diet of the subject, and the response of the subject to the treatment, and can be determined by the treating physician. In some embodiments, a therapeutically effective amount of the cyclosporine analogue (e.g., CRV431) for treating or preventing a proliferative disease such as cancer, or for reducing or inhibiting one or more symptoms of the proliferative disease as described herein, is about 0.1-200 mg, 0.1-150 mg, 0.1-100 mg, 0.1-50 mg, 0.1-30 mg, 0.5-20 mg, 0.5-10 mg or 1-10 mg (e.g., per day or per dose), or as deemed appropriate by the treating physician, which can be administered in a single dose or in divided doses. In some embodiments, the therapeutically effective dose (e.g., per day or per dose) of the cyclosporine analogue (e.g., CRV431) for treating or preventing a proliferative disease such as cancer, or for reducing or inhibiting one or more symptoms of the proliferative disease as described herein, is about 0.1-1 mg (e.g., about 0.1 mg, 0.5 mg or 1 mg), about 1-5 mg (e.g., about 1 mg, 2 mg, 3 mg, 4 mg or 5 mg), about 5-10 mg (e.g., about 5 mg, 6 mg, 7 mg, 8 mg, 9 mg or 10 mg), about 10-20 mg (e.g., about 10 mg, 15 mg or 20 mg), about 20-30 mg (e.g., about 20 mg, 25 mg or 30 mg), about 30-40 mg (e.g., about 30 mg, 35 mg or 40 mg), about 40-50 mg (e.g., about 40 mg, 45 mg or 50 mg), about 50-100 mg (e.g., about 50 mg, 60 mg, 70 mg, 80 mg, 90 mg or 100 mg), about 100-150 mg (e.g., about 100 mg, 125 mg or 150 mg), or about 150-200 mg (e.g., about 150 mg, 175 mg or 200 mg). In some embodiments, the therapeutically effective dose of the cyclosporine analogue (e.g., CRV431) is administered one or more (e.g., two, three or more) times a day, or once every two or three days, or once, twice or thrice a week, or as deemed appropriate by the treating physician. In some embodiments, the composition comprises a therapeutically or prophylactically effective amount of the cyclosporine analogue (e.g., CRV431) or a pharmaceutically acceptable salt, solvate, stereoisomer thereof.

The cyclosporine analogue (e.g., CRV431) can also be dosed in an irregular manner. For example, the cyclosporine analogue (e.g., CRV431) can be administered once, twice or thrice in a period of 30 minutes, one hour, two hours or more, in an irregular manner. Furthermore, the cyclosporine analogue (e.g., CRV431) can be taken pro re rata (as needed). For instance, the cyclosporine analogue (e.g., CRV431) can be administered 1, 2, 3, 4, 5 or more times, whether in a regular or irregular manner, until the proliferative disease/condition (e.g., cancer) improves. Once relief from the proliferative disease/condition (e.g., cancer) is achieved, dosing of the cyclosporine analogue (e.g., CRV431) can optionally be discontinued. If the disease disorder/condition returns, administration of the cyclosporine analogue (e.g., CRV431), whether in a regular or irregular manner, can be resumed. The appropriate dosage of, frequency of dosing of and length of treatment with the cyclosporine analogue (e.g., CRV431) can be determined by the treating physician.

The cyclosporine analogue (e.g., CRV431) can also be used prophylactically to treat or prevent a proliferative disease such as cancer, or to prevent or reduce one or more symptoms of the proliferative disease (e.g., fibrosis), or to reduce or inhibit the onset of one or more symptoms of proliferative disease (e.g., fibrosis). The prophylactically effective amount of a cyclosporine analogue (e.g., CRV431) can be any therapeutically effective amount of the cyclosporine analogue (e.g., CRV431) described herein.

The cyclosporine analogue (e.g., CRV431) can be administered via any suitable route. Potential routes of administration of the cyclosporine analogue (e.g., CRV431) include without limitation oral, parenteral (including intramuscular, subcutaneous, intradermal, intravascular, intravenous, intraarterial, intramedullary and intrathecal), intracavitary, intraperitoneal, and topical (including dermal/epicutaneous, transdermal, mucosal, transmucosal, intranasal [e.g., by nasal spray or drop], intraocular [e.g., by eye drop], pulmonary [e.g., by oral or nasal inhalation], buccal, sublingual, rectal and vaginal). In some embodiments, the cyclosporine analogue (e.g., CRV431) is administered orally (e.g., as a capsule or tablet, optionally with an enteric coating). In other embodiments, the cyclosporine analogue (e.g., CRV431) is administered parenterally (e.g., intravenously, subcutaneously or intradermally). In further embodiments, the cyclosporine analogue (e.g., CRV431) is administered topically (e.g., dermally, epicutaneously, transdermally, mucosally, transmucosally, buccally or sublingually).

In some embodiments, the cyclosporine analogue (e.g., CRV431) is administered without food. In some embodiments, the cyclosporine analogue (e.g., CRV431) is administered at least about 1 or 2 hours before or after a meal. In some embodiments, the cyclosporine analogue (e.g., CRV431) is administered at least about 2 hours after an evening meal. The cyclosporine analogue (e.g., CRV431) can also be taken substantially concurrently with food (e.g., within about 0.5, 1 or 2 hours before or after a meal, or with a meal).

In some embodiments where a more rapid establishment of a therapeutic level of the cyclosporine analogue (e.g., CRV431) is desired, the cyclosporine analogue (e.g., CRV431) is administered under a dosing schedule in which a loading dose is administered, followed by (i) one or more additional loading doses and then one or more therapeutically effective maintenance doses, or (ii) one or more therapeutically effective maintenance doses without an additional loading dose, as deemed appropriate by the treating physician. A loading dose of a drug is typically larger (e.g., about 1.5, 2, 3, 4 or 5 times larger) than a subsequent maintenance dose and is designed to establish a therapeutic level of the drug more quickly. The one or more therapeutically effective maintenance doses can be any therapeutically effective dose described herein. In some embodiments, the loading dose is about three times greater than the maintenance dose. In some embodiments, a loading dose of the cyclosporine analogue (e.g., CRV431) is administered, followed by administration of a maintenance dose of the cyclosporine analogue (e.g., CRV431) after an appropriate time (e.g., after about 12 or 24 hours) and thereafter for the duration of therapy—e.g., a loading dose of the cyclosporine analogue (e.g., CRV431) is administered on day 1 and a maintenance dose is administered on day 2 and thereafter for the duration of therapy. In some embodiments, the cyclosporine analogue (e.g., CRV431) is administered in a loading, dose of about 1.5, 3, 15 or 30 mg (e.g., 3×about 0.5, 1, 5 or 10 mg) orally (e.g., as a tablet) on day 1, followed by a maintenance dose of about 0.5, 1, 5 or 10 mg orally (e.g., as a tablet) once daily, optionally at bedtime, for at least about 2 weeks, 1 month (4 weeks), 6 weeks, 2 months, 10 weeks, 3 months, 4 months, 5 months, 6 months, 1 year, 1.5 years, 2 years, 3 years or longer (e.g., at least about 6 weeks, 2 months, 3 months or 6 months). In some embodiments, the cyclosporine analogue (e.g., CRV431) is administered in a loading dose of about 15 mg (e.g., 3×about 5 mg) orally (e.g., as a tablet) on day 1, followed by a maintenance dose of about 5 mg orally (e.g., as a tablet) once daily, optionally at bedtime, for at least about 2 weeks, 1 month, 6 weeks, 2 months, 3 months, 6 months, 1 year, 1.5 years, 2 years, 3 years or longer (e.g., at least about 6 weeks, 2 months, 3 months or 6 months).

In some embodiments, a first loading dose of the cyclosporine analogue (e.g., CRV431) is administered on day 1, a second loading dose is administered on day 2, and a maintenance dose is administered on day 3 and thereafter for the duration of therapy. In some embodiments, the first loading dose is about three times greater than the maintenance dose, and the second loading dose is about two times greater than the maintenance dose.

As disclosed herein, the therapeutic agent (e.g., the cyclosporine analogue (e.g., CRV431)) can be formulated for administration in a pharmaceutical composition comprising a physiologically acceptable surface active agents, carriers, diluents, excipients, smoothing agents, suspension agents, film forming substances, coating assistants, or a combination thereof. In some embodiments, the therapeutic agent (e.g., the cyclosporine analogue (e.g., CRV431)) are formulated for administration with a pharmaceutically acceptable carrier or diluent. The therapeutic agent (e.g., the cyclosporine analogue (e.g., CRV431)) can be formulated as a medicament with a standard pharmaceutically acceptable carrier(s) and/or excipient(s) as is routine in the pharmaceutical art. The exact nature of the formulation will depend upon several factors including the desired route of administration. In some embodiments, the cyclosporine analogue (e.g., CRV431) is formulated for oral, intravenous, intragastric, intravascular or intraperitoneal administration. Standard pharmaceutical formulation techniques may be used, such as those disclosed in Remington's The Science and Practice of Pharmacy, 21st Ed., Lippincott Williams & Wilkins (2005), incorporated herein by reference in its entirety.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose: starches, such as corn starch and potato starch; cellulose and its derivatives, such as sodium carboxymethyl cellulose, powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and theobroma oil; polyols such as propylene glycol, glycerin, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject therapeutic agent is basically determined by the way the composition is to be administered.

The compositions described herein are preferably provided in unit dosage form. As used herein, a "unit dosage form" is a composition containing an amount of a therapeutic agent (e.g., a cyclosporine analogue (e.g., CRV431)) that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and can be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions include compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the therapeutic agent (e.g., the cyclosporine analogue (e.g., CRV431)). The amount of carrier employed in conjunction with the therapeutic agent (e.g., the cyclosporine analogue (e.g., CRV431)) is sufficient to provide a practical quantity of material for administration per unit dose of the therapeutic agent (e.g., the cyclosporine analogue (e.g., CRV431)). Techniques and compositions for making dosage forms useful in the methods described herein are described in the following references, ail incorporated by reference herein: Modern Pharmaceutics, 4th Ed., Chapters 9 and 10 (Banker & Rhodes, editors, 2002); Lieberman et αi, Pharmaceutical Dosage Forms: Tablets (1989), and Ansel, Introduction to Pharmaceutical Dosage Forms 8th Edition (2004).

Various oral dosage forms can be used, including such solid forms as tablets, capsules, and granules. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carriers suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Other compositions useful for attaining systemic delivery of the subject therapeutic agents include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

For topical use, creams, ointments, gels, solutions or suspensions, etc., containing the therapeutic agent (e.g., the cyclosporine analogue (e.g., CRV431)) disclosed herein are employed. Topical formulations may generally be comprised of a pharmaceutical carrier, co-solvent, emulsifier, penetration enhancer, preservative system, and emollient.

For intravenous administration, the therapeutic agent (e.g., the cyclosporine analogue (e.g., CRV431)) and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HC1, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, PDA J Pharm Sci and Tech 1998, 52 238-31 1 and Nema et al., Excipients and Their Role in Approved Injectable Products: Current Usage and Future Directions, PDA J Pharm Sci and Tech 2011, 65 287-332, both of which are incorporated herein by reference in their entirety. Antimicrobial agents may also be included to achieve a bacteriostatic or fungistatic solution, including but not limited to phenyl mercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a therapeutic agent (e.g., the cyclosporine analogue (e.g., CRV431)) described herein and another agent, the combination may be provided to caregivers as a mixture, or the caregivers may mix the two agents prior to administration, or the two agents may be administered separately.

In non-human animal studies, applications of potential products are commenced at higher dosage levels, with dosage being decreased until the desired effect is no longer achieved or adverse side effects disappear. The dosage may range broadly, depending upon the desired effects and the therapeutic indication. Typically, dosages may be between about 0.1 mg/kg and 4000 mg/kg body weight, preferably between about 80 mg/kg and 1600 mg/kg body weight. Alternatively dosages may be based and calculated upon the surface area of the patient, as understood by those of skill in the art.

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on many factors including the subject being treated, the severity of the affliction, the manner of administration, the judgment of the prescribing physician. The therapeutic agent (e.g., cyclosporine analogue (e.g., CRV431)) or combination of therapeutic agents disclosed herein may be administered orally or via injection at a dose from 0, 1 mg/kg to 4000 mg/kg of the patient's body weight per day. The dose range for adult humans is generally from 1 g to 100 g/day. Tablets or other forms of presentation provided in discrete units may conveniently contain an amount of the therapeutic agent (e.g., cyclosporine analogue (e.g., CRV431)) or combination of therapeutic agents disclosed herein which is effective at such dosage or as a multiple of the same, for instance, units containing 1 g to 60 g (for example, from about 5 g to 20 g, from about 10 g to 50 g, from about 20 g to 40 g, or from about 25 g to 35 g). The precise amount of therapeutic agent administered to a patient will be the responsibility of the attendant physician. However, the dose employed will depend on a number of factors, including the age and sex of the patient, the precise disorder being treated, and its severity. Additionally, the route of administration may vary depending on the condition and its severity. A typical dose of the therapeutic agent (e.g., cyclosporine analogue (e.g., CRV431)) can be from 0.02 g to 1.25 g per kg of body weight, for example from 0.1 g to 0.5 g per kg of body weight, depending on such parameters. In some embodiments, a dosage of the therapeutic agent (e.g., cyclosporine analogue (e.g., CRV431)) can be from 1 g to 100 g, for example, from 10 g to 80 g, from 15 g to 60 g, from 20 g to 40 g, or from 25 g to 35 g. In A physician will be able to determine the required dosage of the therapeutic agent (e.g., cyclosporine analogue (e.g., CRV431)) for any particular subject.

The exact formulation, route of administration and dosage for the pharmaceutical compositions of the therapeutic agent (e.g., cyclosporine analogue (e.g., CRV431)) or combination of therapeutic agents disclosed herein can be chosen by the individual physician in view of the patient's condition. Typically, the dose range of the composition administered to the patient can be from about 0.1 to about 4000 mg/kg of the patient's body weight. The dosage may be a single one or a series of two or more given in the course of one or more days, as is needed by the patient. In instances where human dosages for therapeutic agents have been established for at least some condition, the present disclosure will use those same dosages, or dosages that are between about 0.1% and about 5000%, more preferably between about 25% and about 1000% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. In cases of administration of a pharmaceutically acceptable salt, dosages may be calculated as the free base. In some embodiments, the composition is administered 1 to 4 times per day. Alternatively the compositions disclosed herein may be administered by continuous intravenous infusion, e.g., at a dose of each active ingredient up to 100 g per day. As will be understood by those of skill in the art, in certain situations it may be necessary to administer the compositions disclosed herein in amounts that exceed, or even far exceed, the above-stated, preferred dosage range in order to effectively and aggressively treat particularly aggressive diseases or infections. In some embodiments, the therapeutic agent (e.g., cyclosporine analogue (e.g., CRV431)) or combination of therapeutic agents disclosed herein will be administered for a period of continuous therapy, for example for a week or more, or for months or years.

In some embodiments, the dosing regimen of the therapeutic agent (e.g., cyclosporine analogue (e.g., CRV431)) or combination of therapeutic agents disclosed herein is administered for a period of time, which time period can be, for example, from at least about 1 week to at least about 4 weeks, from at least about 4 weeks to at least about 8 weeks, from at least about 4 weeks to at least about 12 weeks, from at least about 4 weeks to at least about 16 weeks, or longer. The dosing regimen of the therapeutic agent (e.g., cyclosporine analogue (e.g., CRV431)) or combination of therapeutic agents disclosed herein can be administered three times a day, twice a day, daily, every other day, three times a week, every other week, three times per month, once monthly, substantially continuously or continuously.

The cyclosporine analogue (e.g., CRV431) can be administered alone or in the form of a composition (e.g., a pharmaceutical composition). In some embodiments, a pharmaceutical composition comprises a cyclosporine analogue (e.g., CRV431) or a pharmaceutically acceptable salt, solvate, hydrate, clathrate, polymorph, prodrug or metabolite thereof, and one or more pharmaceutically acceptable carriers or excipients. The composition can optionally contain one or more additional therapeutic agents as described herein. A pharmaceutical composition contains a therapeutically effective amount of a therapeutic agent (e.g., a cyclosporine analogue (e.g., CRV431)) and one or more pharmaceutically acceptable carriers or excipients, and is formulated for administration to a subject for therapeutic use. For purposes of the content of a pharmaceutical composition, the terms "therapeutic agent", "active ingredient", "active agent" and "drug" encompass prodrugs.

A pharmaceutical composition contains a therapeutic agent (e.g., a cyclosporine analogue (e.g., CRV431)) in substantially pure form. In some embodiments, the purity of the therapeutic agent is at least about 95%, 96%, 97%, 98% or 99%. In some embodiments, the purity of the therapeutic agent is at least about 98% or 99%. In addition, a pharmaceutical composition is substantially free of contaminants or impurities. In some embodiments, the level of contaminants or impurities other than residual solvent in a pharmaceutical composition is no more than about 5%, 4%, 3%, 2% or 1% relative to the combined weight of the intended active and inactive ingredients. In some embodiments, the level of contaminants or impurities other than residual solvent in a pharmaceutical composition is no more than about 2% or 1% relative to the combined weight of the intended active and inactive ingredients. Pharmaceutical compositions generally are prepared according to current good manufacturing practice (GMP), as recommended or required by, e.g., the Federal Food, Drug, and Cosmetic Act § 501 (a)(2)(B) and the International Conference on Harmonisation Q7 Guideline.

Pharmaceutically acceptable carriers and excipients include pharmaceutically acceptable materials, vehicles and substances. Non-limiting examples of excipients include liquid and solid fillers, diluents, binders, lubricants, glidants, solubilizers, surfactants, dispersing agents, disintegration agents, emulsifying agents, wetting agents, suspending agents, thickeners, solvents, isotonic agents, buffers, pH adjusters, stabilizers, preservatives, antioxidants, antimicrobial agents, antibacterial agents, antifungal agents, absorption-delaying agents, sweetening agents, flavoring agents, coloring agents, adjuvants, encapsulating materials and coating materials. The use of such excipients in pharmaceutical formulations is known in the art. For example, conventional vehicles and carriers include without limitation oils (e.g., vegetable oils, such as sesame oil), aqueous solvents (e.g., saline, phosphate-buffered saline [PBS] and isotonic solutions [e.g., Ringer's solution]), and solvents (e.g., dimethyl sulfoxide [DMSO] and alcohols [e.g., ethanol, glycerol and propylene glycol]). Except insofar as any conventional carrier or excipient is incompatible with the active ingredient, the disclosure encompasses the use of conventional carriers and excipients in formulations containing a therapeutic agent (e.g., a cyclosporine analogue (e.g., CRV431)). See, e.g., Remington: The Science and Practice of Pharmacy, 21st Ed., Lippincott Williams & Wilkins (Philadelphia, Pennsylvania [2005]); Handbook of Pharmaceutical Excipients, 5th Ed., Rowe et al., Eds., The Pharmaceutical Press and the American Pharmaceutical Association (2005); Handbook of Pharmaceutical Additives, 3rd Ed., Ash and Ash, Eds., Gower Publishing Co. (2007); and Pharmaceutical Preformulation and Formulation, Gibson, Ed., CRC Press (Boca Raton, Florida, 2004).

Proper formulation can depend on various factors, such as the mode of administration chosen. Potential modes of administration of pharmaceutical compositions comprising a cyclosporine analogue (e.g., CRV431) include without limitation oral, parenteral (including intramuscular, subcutaneous, intradermal, intravascular, intravenous, intraarterial, intraperitoneal, intramedullary, intrathecal and topical), intracavitary, and topical (including dermal/epicutaneous, transdermal, mucosal, transmucosal, intranasal [e.g., by nasal spray or drop], pulmonary [e.g., by oral or nasal inhalation], buccal, sublingual, rectal [e.g., by suppository], and vaginal [e.g., by suppository]).

As an example, formulations of a cyclosporine analogue (e.g., CRV431) suitable for oral administration can be presented as, e.g., boluses; tablets, capsules, pills, cachets or lozenges; as powders or granules; as semisolids, electuaries, pastes or gels; as solutions or suspensions in an aqueous liquid or/and a non-aqueous liquid; or as oil-in-water liquid emulsions or water-in-oil liquid emulsions.

Tablets can contain a cyclosporine analogue (e.g., CRV431) in admixture with, e.g., a filler or inert diluent (e.g., calcium carbonate, calcium phosphate, lactose, mannitol or microcrystalline cellulose), a binding agent (e.g., a starch, gelatin, acacia, alginic acid or a salt thereof, or microcrystalline cellulose), a lubricating agent (e.g., stearic acid, magnesium stearate, talc or silicon dioxide), and a disintegrating agent (e.g., crospovidone, croscarmellose sodium or colloidal silica), and optionally a surfactant (e.g., sodium lauryl sulfate). The tablets can be uncoated or can be coated with, e.g., an enteric coating that protects the active ingredient from the acidic environment of the stomach, or with a material that delays disintegration and absorption of the active ingredient in the gastrointestinal tract and thereby provides a sustained action over a longer time period. In some embodiments, a tablet comprises a cyclosporine analogue (e.g., CRV431), mannitol, microcrystalline cellulose, magnesium stearate, silicon dioxide, croscarmellose sodium and sodium lauryl sulfate, and optionally lactose monohydrate, and the tablet is optionally film-coated (e.g., with Opadry®

Push-fit capsules or two-piece hard gelatin capsules can contain a cyclosporine analogue (e.g., CRV431) in admixture with, e.g., a filler or inert solid diluent (e.g., calcium carbonate, calcium phosphate, kaolin or lactose), a binder (e.g., a starch), a glidant or lubricant (e.g., talc or magnesium stearate), and a disintegrant (e.g., crospovidone), and optionally a stabilizer or/and a preservative. For soft capsules or single-piece gelatin capsules, a cyclosporine analogue (e.g., CRV431) can be dissolved or suspended in a suitable liquid (e.g., liquid polyethylene glycol or an oil medium, such as a fatty oil, peanut oil, olive oil or liquid paraffin), and the liquid-filled capsules can contain one or more other liquid excipients or/and semi-solid excipients, such as a stabilizer or/and an amphiphilic agent (e.g., a fatty acid ester of glycerol, propylene glycol or sorbitol).

Compositions for oral administration can also be formulated as solutions or suspensions in an aqueous liquid or/and a non-aqueous liquid, or as oil-in-water liquid emulsions or water-in-oil liquid emulsions. Dispersible powder or granules of a cyclosporine analogue (e.g., CRV431) can be mixed with any suitable combination of an aqueous liquid, an organic solvent or/and an oil and any suitable excipients (e.g., any combination of a dispersing agent, a wetting agent, a suspending agent, an emulsifying agent or/and a preservative) to form a solution, suspension or emulsion.

A cyclosporine analogue (e.g., CRV431) can also be formulated for parenteral administration by injection or infusion to circumvent gastrointestinal absorption and first-pass metabolism. A representative parenteral route is intravenous.

Additional advantages of intravenous administration include direct administration of a therapeutic agent into systemic circulation to achieve a rapid systemic effect, and the ability to administer the agent continuously or/and in a large volume if desired. Formulations for injection or infusion can be in the form of, e.g., solutions, suspensions or emulsions in oily or aqueous vehicles, and can contain excipients such as suspending agents, dispersing agents or/and stabilizing agents. For example, aqueous or non-aqueous (e.g., oily) sterile injection solutions can contain a cyclosporine analogue (e.g., CRV431) along with excipients such as an antioxidant, a buffer, a bacteriostat and solutes that render the formulation isotonic with the blood of the subject. Aqueous or non-aqueous sterile suspensions can contain a cyclosporine analogue (e.g., CRV431) along with excipients such as a suspending agent and a thickening agent, and optionally a stabilizer and an agent that increases the solubility of the cyclosporine analogue (e.g., CRV431) to allow for the preparation of a more concentrated solution or suspension. As another example, a sterile aqueous solution for injection or infusion (e.g., subcutaneously or intravenously) can contain a cyclosporine analogue (e.g., CRV431), NaCl, a buffering agent (e.g., sodium citrate), a preservative (e.g., meta-cresol), and optionally a base (e.g., NaOH) or/and an acid (e.g., HCl) to adjust pH.

For topical administration, a cyclosporine analogue (e.g., CRV431) can be formulated as, e.g., a buccal or sublingual tablet or pill. Buccal or sublingual tablets or pills may avoid first-pass metabolism and circumvention of gastrointestinal absorption. A buccal or sublingual tablet or pill can be designed to provide faster release of the cyclosporine analogue (e.g., CRV431) for more rapid uptake of it into systemic circulation. In addition to a therapeutically effective amount of the cyclosporine analogue (e.g., CRV431), the buccal or sublingual tablet or pill can contain suitable excipients, including without limitation any combination of fillers and diluents (e.g., mannitol and sorbitol), binding agents (e.g., sodium carbonate), wetting agents (e.g., sodium carbonate), disintegrants (e.g., crospovidone and croscarmellose sodium), lubricants (e.g., silicon dioxide [including colloidal silicon dioxide] and sodium stearyl fumarate), stabilizers (e.g., sodium bicarbonate), flavoring agents (e.g., spearmint flavor), sweetening agents (e.g., sucralose), and coloring agents (e.g., yellow iron oxide).

For topical administration, a cyclosporine analogue (e.g., CRV431) can also be formulated for intranasal administration. The nasal mucosa provides a big surface area, a porous endothelium, a highly vascular subepithelial layer and a high absorption rate, and hence allows for high bioavailability. Moreover, intranasal administration avoids first-pass metabolism and can introduce a significant concentration of the cyclosporine analogue (e.g., CRV431) to the central nervous system, allowing the cyclosporine analogue (e.g., CRV431) to block the central cough reflex via the nucleus tractus solitarius in the cough center in the medulla oblongata, where vagal afferent nerves terminate. An intranasal solution or suspension formulation can comprise a cyclosporine analogue (e.g., CRV431) along with excipients such as a solubility enhancer (e.g., propylene glycol), a humectant (e.g., mannitol or sorbitol), a buffer and water, and optionally a preservative (e.g., benzalkonium chloride), a mucoadhesive agent (e.g., hydroxyethyl cellulose) or/and a penetration enhancer. In some embodiments, a nasal spray formulation comprises a cyclosporine analogue (e.g., CRV431), microcrystalline cellulose, sodium carboxymethylcellulose, dextrose and water, and optionally an acid (e.g., HCl) to adjust pH. An intranasal solution or suspension formulation can be administered to the nasal cavity by any suitable means, including but not limited to a dropper, a pipette, or spray using, e.g., a metering atomizing spray pump. An additional mode of topical administration is pulmonary, including by oral inhalation and nasal inhalation.

In some embodiments, a cyclosporine analogue (e.g., CRV431) is delivered from a sustained-release composition. As used herein, the term "sustained-release composition" encompasses sustained-release, prolonged-release, extended-release, slow-release and controlled-release compositions, systems and devices. Use of a sustained-release composition can have benefits, such as an improved profile of the amount of the drug or an active metabolite thereof delivered to the target site(s) over a time period, including delivery of a therapeutically effective amount of the drug or an active metabolite thereof over a prolonged time period. In some embodiments, the sustained-release composition delivers the cyclosporine analogue (e.g., CRV431) over a period of at least about 1 day, 2 days, 3 days, 1 week, 2 weeks, 3 weeks, 1 month, 2 months, 3 months or longer. In some embodiments, the sustained-release composition is a drug-encapsulation system, such as nanoparticles, microparticles or a capsule made of, e.g., a biodegradable polymer or/and a hydrogel. In some embodiments, the sustained-release composition comprises a hydrogel. Non-limiting examples of polymers of which a hydrogel can be composed include polyvinyl alcohol, acrylate polymers (e.g., sodium poly acrylate), and other homopolymers and copolymers having a relatively large number of hydrophilic groups (e.g., hydroxyl or/and carboxylate groups). In some embodiments, the sustained-release drug-encapsulation system comprises a membrane-enclosed reservoir, wherein the reservoir contains a drug and the membrane is permeable to the drug. Such a drug-delivery system can be in the form of, e.g., a transdermal patch.

In some embodiments, the sustained-release composition is an oral dosage form, such as a tablet or capsule. For example, a drug can be embedded in an insoluble porous matrix such that the dissolving drag must make its way out of the matrix before it can be absorbed through the gastrointestinal tract. Alternatively, a drug can be embedded in a matrix that swells to form a gel through which the drug exits. Sustained release can also be achieved by way of a single-layer or multi-layer osmotic controlled-release oral delivery system (OROS). An OROS is a tablet with a semi-permeable outer membrane and one or more small laser-drilled holes in it. As the tablet passes through the body, water is absorbed through the semipermeable membrane via osmosis, and the resulting osmotic pressure pushes the drug out through the hole(s) in the tablet and into the gastrointestinal tract where it can be absorbed.

The sustained-release composition can be formulated as polymeric nanoparticles or microparticles, wherein the polymeric particles can be delivered, e.g., by inhalation or injection or from an implant. In some embodiments, the polymeric implant or polymeric nanoparticles or microparticles are composed of a biodegradable polymer. In some embodiments, the biodegradable polymer comprises lactic acid or/and glycolic acid [e.g., an L-lactic acid-based copolymer, such as poly(L-lactide-co-glycolide) or poly(L-lactic acid-co-D,L-2-hydroxyoctanoic acid)]. For example, biodegradable polymeric microspheres composed of polylactic acid or/and polyglycolic acid can serve as sustained-release pulmonary drug-delivery systems. The biodegradable polymer of the polymeric implant or polymeric nanoparticles or microparticles can be selected so that the polymer substantially completely degrades around the time the period of treatment is expected to end, and so that the byproducts of the polymer's degradation, like the polymer, are biocompatible.

For a delayed or sustained release of a cyclosporine analogue (e.g., CRV431), a composition can also be formulated as a depot that can be implanted in or injected into a subject, e.g., intramuscularly or subcutaneously. A depot formulation can be designed to deliver the cyclosporine analogue (e.g., CRV431) over a longer period of time, e.g., over a period of at least about 1 week, 2 weeks, 3 weeks, 1 month, 6 weeks, 2 months, 3 months or longer. For example, the cyclosporine analogue (e.g., CRV431) can be formulated with a polymeric material (e.g., polyethylene glycol (PEG), polylactic acid (PLA) or polyglycolic acid (PGA), or a copolymer thereof (e.g., PLGA)), a hydrophobic material (e.g., as an emulsion in an oil) or/and an ion-exchange resin, or as a sparingly soluble derivative (e.g., a sparingly soluble salt). As an illustrative example, a cyclosporine analogue (e.g., CRV431) can be incorporated or embedded in sustained-release microparticles composed of PLGA and formulated as a monthly depot.

A cyclosporine analogue (e.g., CRV431) can also be contained or dispersed in a matrix material. The matrix material can comprise a polymer (e.g., ethylene-vinyl acetate) and controls the release of the compound by controlling dissolution or/and diffusion of the compound from, e.g., a reservoir, and can enhance the stability of the compound while contained in the reservoir. Such a release system can be designed as a sustained-release system, can be configured as, e.g., a transdermal or transmucosal patch, and can contain an excipient that can accelerate the compound's release, such as a water-swellable material (e.g., a hydrogel) that aids in expelling the compound out of the reservoir.

The release system can provide a temporally modulated release profile (e.g., pulsatile release) when time variation in plasma levels is desired, or a more continuous or consistent release profile when a constant plasma level is desired. Pulsatile release can be achieved from an individual reservoir or from a plurality of reservoirs. For example, where each reservoir provides a single pulse, multiple pulses ("pulsatile" release) are achieved by temporally staggering the single pulse release from each of multiple reservoirs.

In addition, pharmaceutical compositions comprising a cyclosporine analogue (e.g., CRV431) can be formulated as, e.g., liposomes, micelles (e.g., those composed of biodegradable natural or/and synthetic polymers, such as lactosomes), microspheres, microparticles or nanoparticles, whether or not designed for sustained release.

The pharmaceutical compositions can be manufactured in any suitable manner known in the art, e.g., by means of conventional mixing, dissolving, suspending, granulating, dragee-making, levigating, emulsifying, encapsulating, entrapping or compressing processes.

A pharmaceutical composition can be presented in unit dosage form as a single dose wherein all active and inactive ingredients are combined in a suitable system, and components do not need to be mixed to form the composition to be administered. The unit dosage form can contain an effective dose, or an appropriate fraction thereof, of a therapeutic agent (e.g., a cyclosporine analogue (e.g., CRV431). Representative examples of a unit dosage form include a tablet, capsule or pill for oral administration, and powder in a vial or ampoule for oral or nasal inhalation.

A pharmaceutical composition disclosed herein can be presented as a kit, wherein the active ingredient, excipients and carriers (e.g., solvents) are provided in two or more separate containers (e.g., ampoules, vials, tubes, bottles or syringes) and need to be combined to form the composition to be administered. The kit can contain instructions for storing, preparing and administering the composition (e.g., a solution to be injected intravenously).

A kit can contain all active and inactive ingredients in unit dosage form or the active ingredient and inactive ingredients in two or more separate containers, and can contain instructions for using the pharmaceutical composition. In some embodiments, a kit comprises a cyclosporine analogue (e.g., CRV431) or a pharmaceutically acceptable salt, solvate, hydrate, clathrate, polymorph, prodrug or metabolite thereof, and instructions for administering the compound.

EXAMPLES

Some aspects of the embodiments discussed above are disclosed in further detail in the following examples, which are not in any way intended to limit the scope of the present disclosure.

Example 1

Determine Antifibrotic Activity of CRV431 in Fibroblasts from Multiple Different Organs In the present example, five different types of fibroblasts, including (1) lung fibroblasts from a patient with idiopathic pulmonary fibrosis ("IPF"), (2) cardiac fibroblasts, (3) dermal (skin) fibroblasts, (4) renal mesangial cells, and (5) the LX2 hepatic stellate cell line, were used to determine the ability of CRV431 in decreasing production of the ECM molecules, collagen and fibronectin.

As shown in this example, CRV431 dose dependently decreased procollagen and fibronectin secretion from all five types of fibroblasts with similar magnitude, as measured by enzyme-linked immunosorbent assay (ELISA). The extent of inhibition was similar whether or not the cells were stimulated with the profibrotic agent, transforming growth factor-beta (TGFβ), consistent with direct effects on ECM synthesis. In addition, CRV431 dose-dependently decreased ECM production by up to 55% at clinically relevant concentrations, without causing any reduction in cell viability. As disclosed herein, CRV431 can be used to reduce ECM production by inhibiting cyclophilin B, and consistent with this hypothesis, downregulation of cyclophilin B with small interfering RNA (siRNA) similarly decreased procollagen and fibronectin secretion.

Figure 1B:
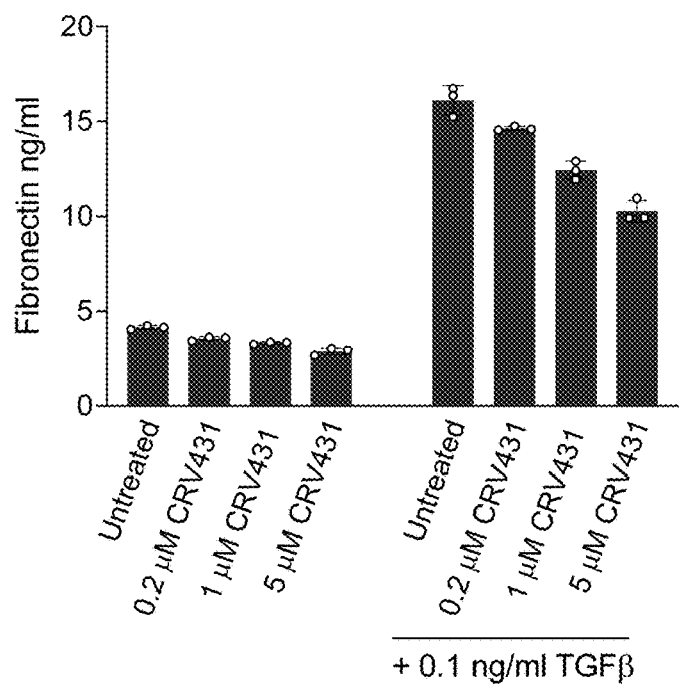

Human LX-2 Hepatic Stellate Cells (Millipore-Sigma, Cat. #SCC064) were cultured in 96-well plates. Treatments were applied in triplicate wells (applied 100 ul treatments per well) for 24 hours. Cells were near confluence at the start of treatments. Cell viability analysis at the end of treatment showed that none of the CRV431 treatments affected cell viability. Spent culture medium collected at the end of the treatments was assayed for procollagen and fibronectin by enzyme-linked immunosorbent assays (ELISA) (Procollagen ELISA antibody pair (ab216064) and fibronectin ELISA antibody pair (ab222262) from Abcam). Procollagen and fibronectin were not detected in medium not applied to cells. Procollagen and fibronectin levels in the medium are represented by means±SD (bars) from 3 replicate wells (open circles). As shown in FIGS. 1A and 1B, CRV431 dose-dependently decreased the abundance of procollagen and fibronectin in the medium both in the absence or presence of 0.1 ng/ml TGFβ.

Figure 2A:
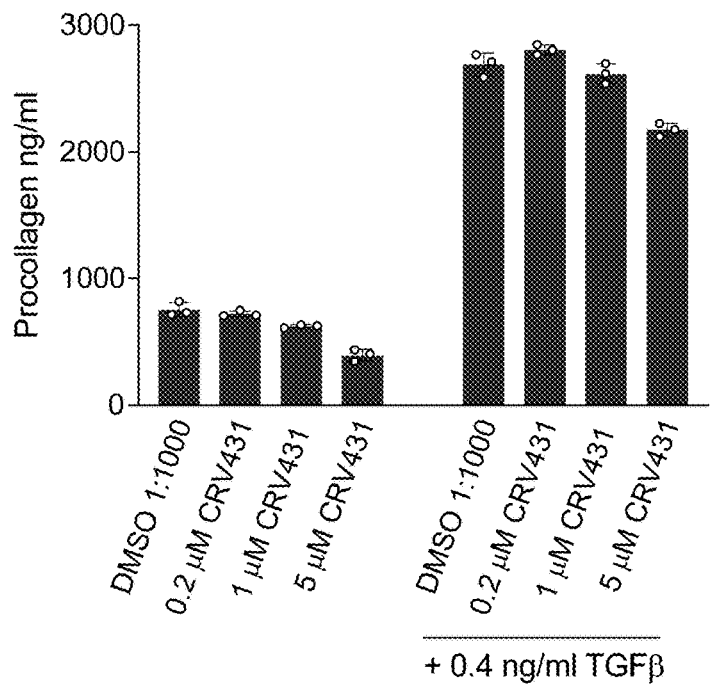
FIGS. 2A-B are histograms showing dose-dependent decreases in the abundance of procollagen and fibronectin caused by CRV431 treatment in human IPF lung fibroblast culture.
Figure 2B:
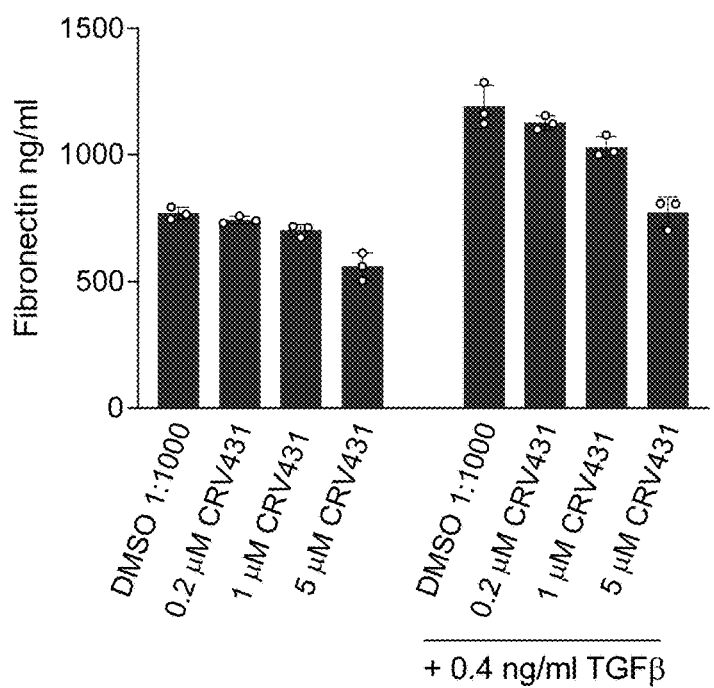

Human Lung Fibroblasts from a Patient with Idiopathic Pulmonary Fibrosis (IPF) (Lonza Bioscience, Cat. #CC-7231) were cultured in 96-well plates. Treatments were applied in triplicate wells (applied 100 ul treatments per well) for 6 days. Cells were near confluence at the start of treatments. Cell viability analysis at the end of treatment showed that none of the CRV431 treatments affected cell viability. Spent culture medium collected at the end of the treatments was assayed for procollagen and fibronectin by enzyme-linked immunosorbent assays (ELISA) (Procollagen ELISA antibody pair (ab216064) and fibronectin ELISA antibody pair (ab222262) from Abcam). Procollagen and fibronectin were not detected in medium not applied to cells. Procollagen and fibronectin levels in the medium are represented by means±SD (bars) from 3 replicate wells (open circles). As shown in FIGS. 2A and 2B, CRV431 dose-dependently decreased the abundance of procollagen and fibronectin in the medium both in the absence or presence of 0.4 ng/ml TGFβ.

Figure 3A:
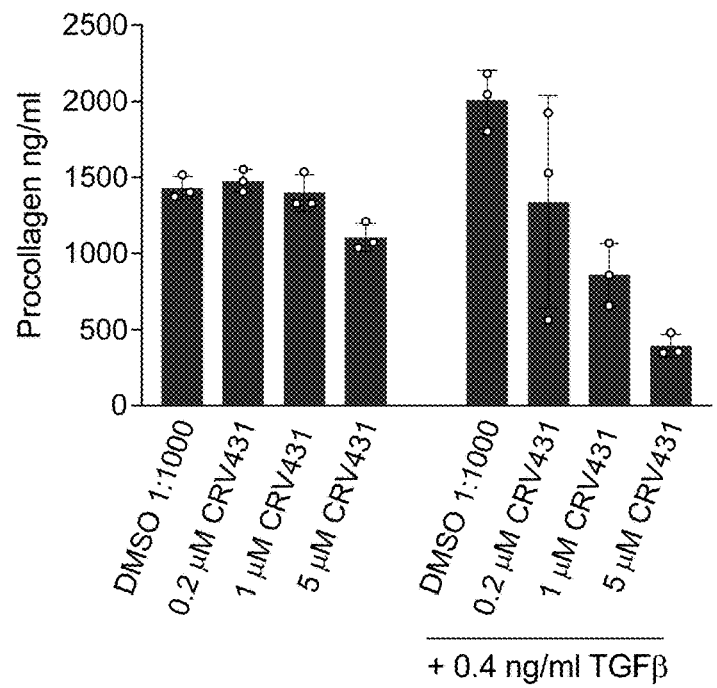
FIGS. 3A-B are histograms showing dose-dependent decreases in the abundance of procollagen and fibronectin caused by CRV431 treatment in human cardiac fibroblast culture.
Figure 3B:
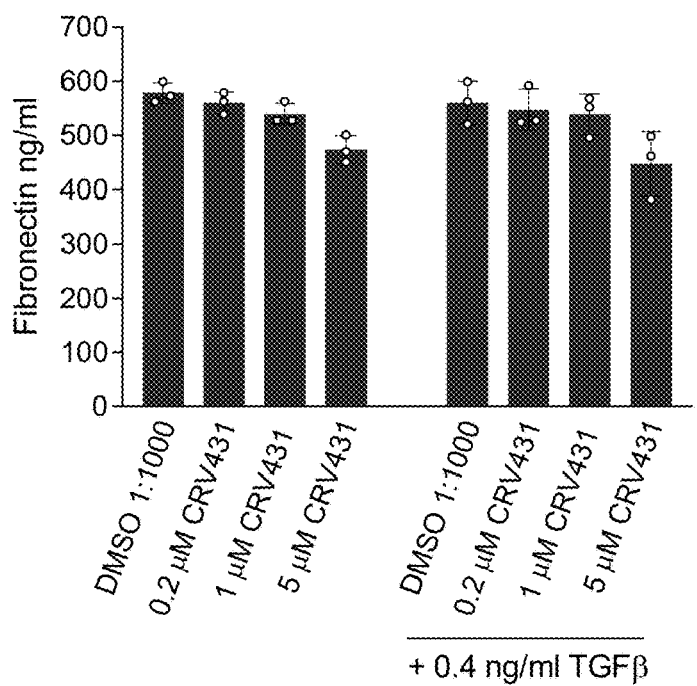

Human cardiac fibroblasts (Lonza Bioscience, Cat. #CC-2903) were cultured in 96-well plates. Treatments were applied in triplicate wells (applied 100 ul treatments per well) for 6 days. Cells were near confluence at the start of treatments. Cell viability analysis at the end of treatment showed that none of the CRV431 treatments affected cell viability. Spent culture medium collected at the end of treatments was assayed for procollagen and fibronectin by enzyme-linked immunosorbent assays (ELISA) (Procollagen ELISA antibody pair (ab216064) and fibronectin ELISA antibody pair (ab222262) from Abcam). Procollagen and fibronectin were not detected in medium not applied to cells. Procollagen and fibronectin levels in the medium are represented by means±SD (bars) from 3 replicate wells (open circles). As shown in FIGS. 3A and 3B, CRV431 dose-dependently decreased the abundance of procollagen and fibronectin in the medium both in the absence or presence of 0.4 ng/ml TGFβ.

Figure 4A:
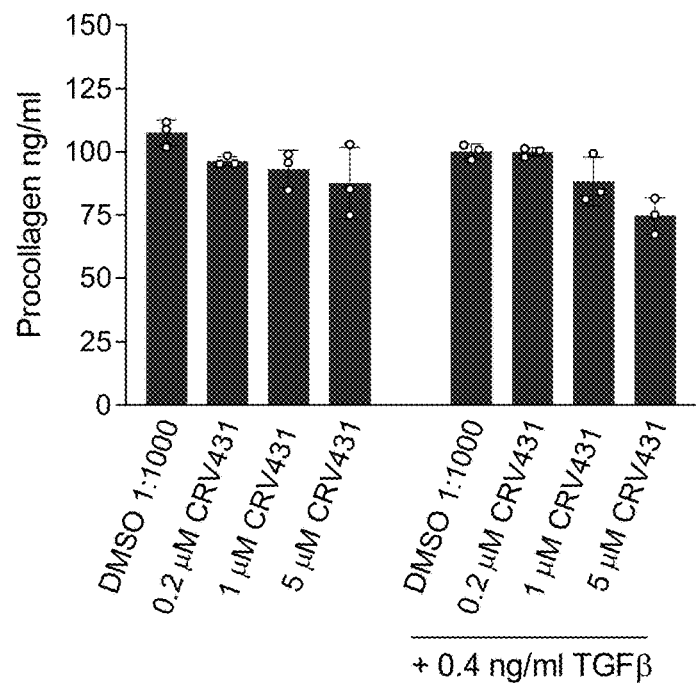
FIGS. 4A-B are histograms showing dose-dependent decreases in the abundance of procollagen and fibronectin caused by CRV431 treatment in human renal mesangial cell culture.
Figure 4B:
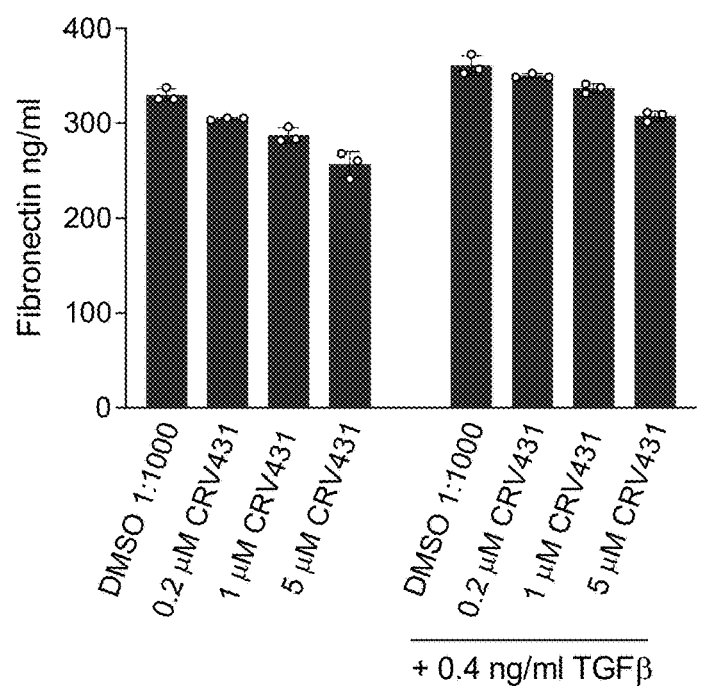

Human renal mesangial cells (ScienCell, Cat. #4200 (SC)) were cultured in 96-well plates. Treatments were applied in triplicate wells (applied 100 ul treatments per well) for 2 days, then re-applied for an additional 2 days. Cells were near confluence at the start of treatments. Cell viability analysis at the end of 4 days of treatment showed that none of the CRV431 treatments affected cell viability. Spent culture medium collected from Day 2-4 of treatment was assayed for procollagen and fibronectin by enzyme-linked immunosorbent assays (ELISA) (Procollagen ELISA antibody pair (ab216064) and fibronectin ELISA antibody pair (ab222262) from Abcam). Procollagen and fibronectin were not detected in medium not applied to cells. Procollagen and fibronectin levels in the medium are represented by means±SD (bars) from 3 replicate wells (open circles). As shown in FIGS. 4A and 4B, CRV431 dose-dependently decreased the abundance of procollagen and fibronectin in the medium both in the absence or presence of 0.4 ng/ml TGFβ.

Figure 5A:
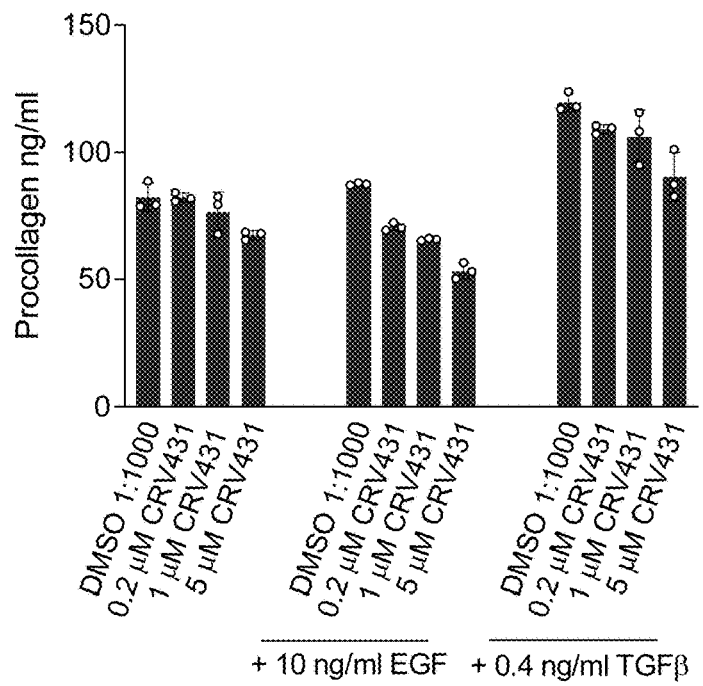
FIGS. 5A-B are histograms showing dose-dependent decreases in the abundance of procollagen and fibronectin caused by CRV431 treatment in human dermal fibroblast culture.
Figure 5B:
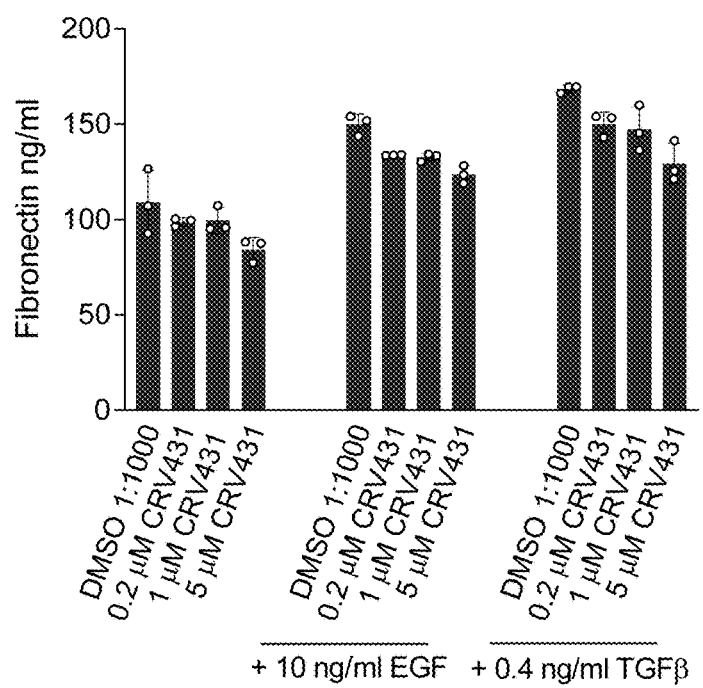

Human adult dermal fibroblasts (Lonza Bioscience, Cat. #CC-2511) were cultured in 96-well plates. Treatments were applied in triplicate wells (applied 100 ul treatments per well) for 1 day, then re-applied for one additional day. Cells were near confluence at the start of treatments. Cell viability analysis at the end of 4 days of treatment showed that none of the CRV431 treatments affected cell viability. Spent culture medium collected from Day 1-2 of treatment was assayed for procollagen and fibronectin by enzyme-linked immunosorbent assays (ELISA) (Procollagen ELISA antibody pair (ab216064) and fibronectin ELISA antibody pair (ab222262) from Abcam). Procollagen and fibronectin were not detected in medium not applied to cells. Procollagen and fibronectin levels in the medium are represented by means±SD (bars) from 3 replicate wells (open circles). from 3 replicate wells (open circles). As shown in FIGS. 5A and 5B, CRV431 dose-dependently decreased the abundance of procollagen and fibronectin in the medium both in the absence or presence of 10 ng/ml epidermal growth factor (EGF) or 0.4 ng/ml TGFβ.

Example 2

Treatment of Human Precision Cut IPF Lung Slices in Culture Using CRV431

This example describes a study conducted with precision cut lung slices. Precision cut slices from explanted lung tissue from a patient with biopsy-confirmed, idiopathic pulmonary fibrosis (IPF) were cultured for 6 days. Treatments were applied to 6 replicate slices per treatment on Day 2 of culture and replaced daily on Days 3, 4, and 5 of culture.

Figure 6A:
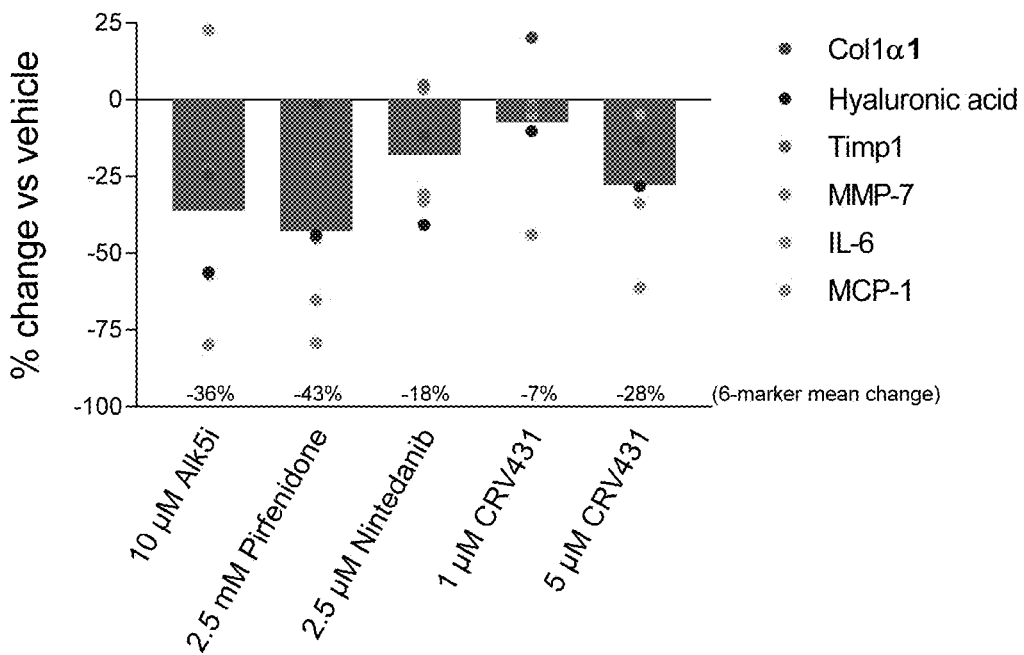
FIG. 6A is a plot showing % daily average change for secreted markers in human precision cut IPF lung slice in culture.

For generating the results of secreted marker (% daily average change) shown in FIG. 6A, spent medium (24-hr intervals) was collected on Days 3, 4, 5, and 6 to measure secretion by ELISA of six markers of inflammation and fibrosis: monocyte chemoattractant protein (MCP-1), interleukin-6 (IL-6), matrix metalloproteinase-7 (MMP-7), tissue inhibitor of metalloproteinase-1 (TIMP1), hyaluronic acid, and collagen 1α1. The mean level of secretion from 6 replicate slices for each drug treatment was expressed as a percentage change relative to DMSO vehicle treatment for each day of treatment, and then the mean percentage change from 4 daily treatment intervals was calculated.

Figure 6B:
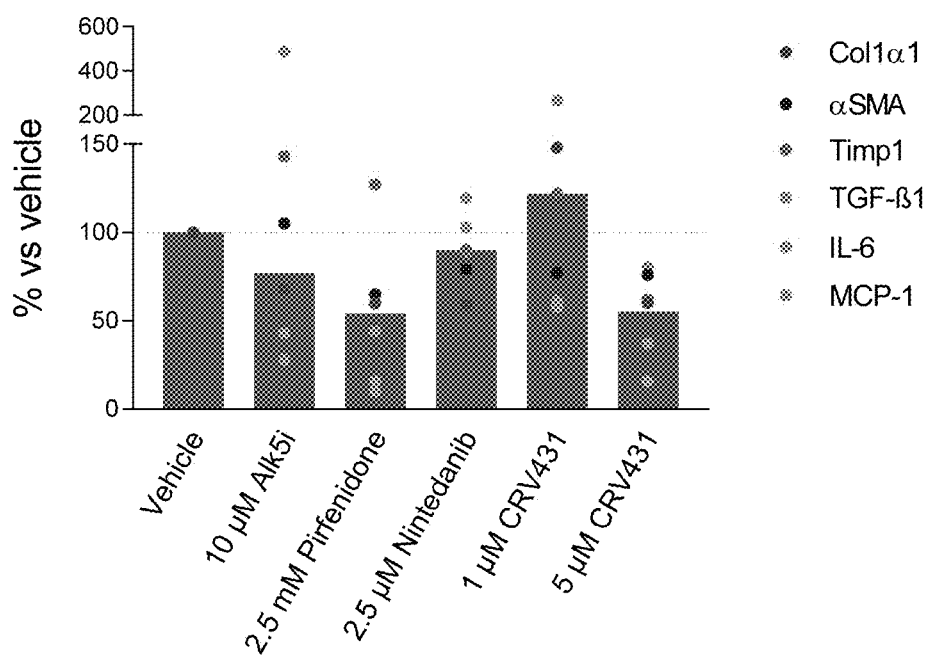
FIG. 6B is a plot showing gene expression in the same human precision cut IPF lung slice culture.

For generating the results of gene expression shown in FIG. 6B, RNA was isolated from 6 pooled lung slices per treatment on Day 6 of culture following 4 days of drug or vehicle treatment and evaluated by reverse transcription-polymerase chain reaction (RT-PCR) for 6 markers of inflammation and fibrosis: MCP-1, IL-6, TGFβ TIMP1, collagen 1α1, and α-smooth muscle actin (αSMA). β actin was used as a reference gene to calculate relative levels of each target gene RNA. CRV431 applied at 5 μM concentration decreased the mean daily secretion and gene expression of all markers in similarity to Alk5i (inhibitor of TGFβ receptor kinase), pirfenidone (approved treatment for IPF), and nintedanib (approved treatment for IPF).

Example 3

Treating Kidney Fibrosis in Mouse Unilateral Ureteral Obstruction (UUQ) Model Using CRV431

Figure 7A:
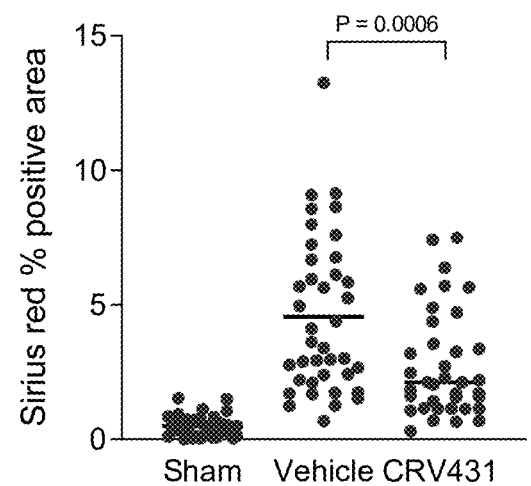
FIGS. 7A-B are plots showing antifibrotic activity of CRV431 in the mouse unilateral ureteral obstruction (UUO) model of kidney fibrosis.
Figure 7B:
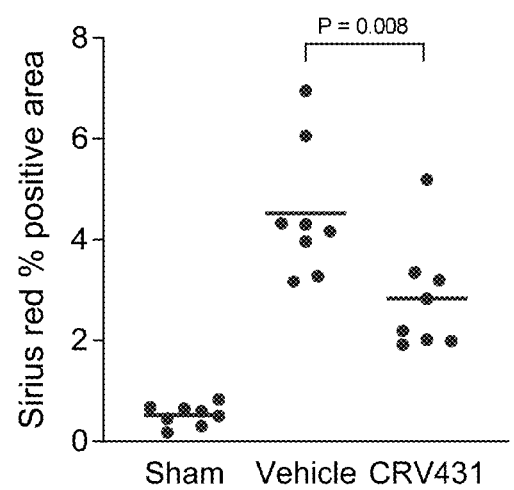

This example describes a study conducted in the mouse unilateral ureteral obstruction (UUO) model of kidney fibrosis. Seven-week-old female C57BL/6 mice were used in this study (n=8 mice per group). Sham group mice received no UUO. The remaining mice underwent complete surgical ligation of the left ureter. Vehicle and CRV431 at 50 mg/kg/day were administered by daily oral gavage for 13 days starting on the day of surgery. Mice were sacrificed on Day 14, and left kidneys were processed histologically and stained for fibrotic collagen with Sirius red. The percentage of each histological section with Sirius red staining was measured morphometrically in 5 sections from each kidney. Results are shown in FIG. 7A (showing Sirius red in individual tissue sections) and 7B (showing Sirius red in individual mice (5 tissue sections per mouse)). One-way ANOVA with Tukey's multiple comparisons demonstrated that CRV431 treatment produced a statistically significant decrease in Sirius red staining when data were presented both per-section and per-animal.

Example 4

Antifibrotic Activity of CRV431 in Human Precision Cut Liver Slices (PCLS)

This example describes a study conducted with human PCLS to determine antifibrotic activity of CRV431, in which it was observed that PCLS from all 5 human donors had some pre-existing fibrosis which was increased by TGFβ+PDGF-BB stimulation to 7-11% by fractional area. CRV431 was most effective of five NASH drug candidates in preventing TGFβ+PDGF-BB-induced tissue fibrosis. Most CRV431-treated slices also showed less fibrosis than vehicle-treated slices after 6 days of culture in the absence of exogenous TGFβ+PDGF-BB. Decreased tissue fibrosis was accompanied by reduced secretion of collagen1α1, fibronectin, hyaluronic acid, IL-6, and MCP-1, and by reductions in RNA levels of collagen1α1, αSMA, TIMP1, IL-6, and MCP-1 as demonstrated by qRT-PCR. RNA-Seq analysis similarly showed that CRV431 decreased expression of many fibrosis-related genes, including more than 10 collagen genes, collagen hydroxylases and oxidases, ACTA2, VEGF, and TIMPs. Gene expression varied considerably among donors, such that the expression of fewer than 200 genes were universally changed by CRV431 in all donors. Many of these pan-donor transcriptional changes were consistent with anti-NASH, anti-fibrotic, and anti-oncogenic activities described for the genes in the literature. Notable genes universally influenced by CRV431 in the absence of TGFβ+PDGF-BB were ESM1 (2.2-fold decrease in RNA; −2.2), NCOA3 (−2.7), IFI44L (−4.8), miR-194-2 (−7.9), and DKK1 (3.8-fold increase in RNA; +3.8). In the presence of exogenous TGFβ+PDGF-BB, notable genes universally influenced by CRV431 were LOXL2 (−1.9) UBD/FAT10 (−2.0), ESMI (−2.6), STRA6 (−3.1), RCCD1 (−3.6), and DUOX2 (−4.5). Without being bound by any particular theory, it is believed that the results described herein indicate CRV431 is capable of preventing fibrosis formation and reversing fibrosis.

PCLS were obtained from 5 human donors who underwent resection of liver cancer. Replicate slices were collected from healthy margins of the resections and cultured for 4 or 6 days depending on the experimental protocol. In the Nonstimulation Protocol slices were cultured for 6 days and treated for the entire period with DMSO vehicle or 5 µM CRV431. In the Stimulation Protocol slices were rested for 1 day and then administered the cytokines, TGFβ and PDGF-BB, for 3 days to stimulate inflammation and fibrosis. DMSO vehicle, CRV431 (1 and 5 µM), Alk5i (10 µM), obeticholic acid (5 µM), elafibranor (5 µM), resmetirom (5 M), and Aramchol (5 µM) were administered individually as drug treatments in the Stimulation Protocol concurrent with TGFβ+PDGF-BB. Culture medium treatments were replaced daily.

Figure 8A:
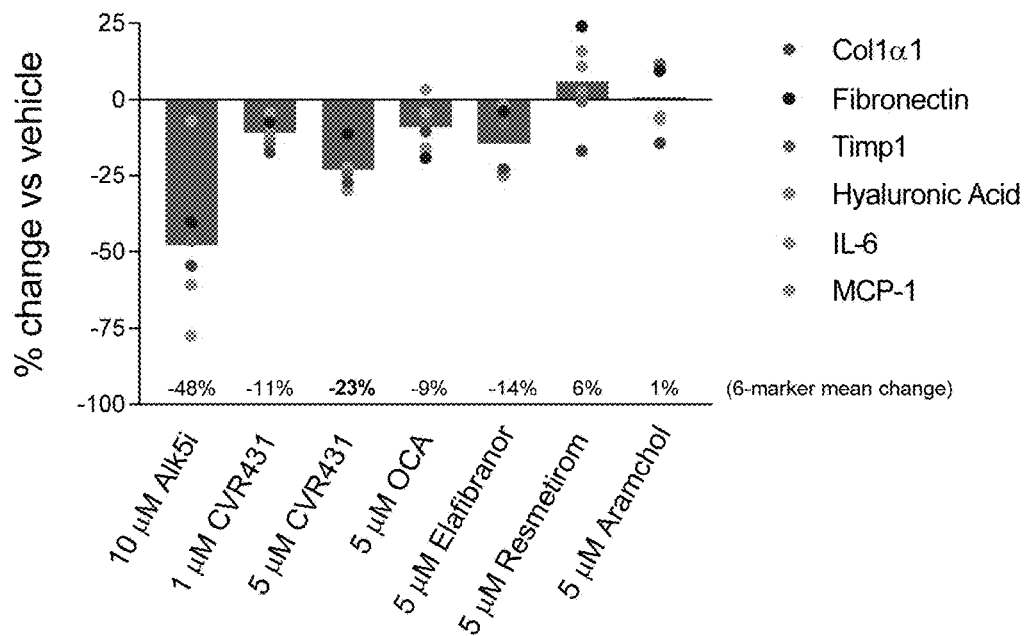
FIGS. 8A-C are plots showing antifibrotic activity of CRV431 in human precision cut liver slices (PCLS).

Four types of evaluations were conducted on the PCLS: (a) secretion of inflammation and fibrosis biomarkers into the culture medium, (b) histological staining and quantitation of Sirius red as a measure of tissue fibrosis, (c) gene expression of inflammation and fibrosis biomarkers by RT-PCR, and (d) RNA sequencing (RNA-Seq) of the complete transcriptome. Each of the four types of evaluation is described below:

(a) Biomarker secretion. Spent culture medium was collected daily from duplicate slices for each treatment. ELISAs were used to quantify secretion of monocyte chemoattractant protein (MCP-1), interleukin-6 (IL-6), tissue inhibitor of metalloproteinase-1 (TIMP1), hyaluronic acid, fibronectin, and collagen 1α1. For each donor the mean level of biomarker secretion in each treatment group was expressed as a percentage change relative to DMSO vehicle, the percentages averaged for all donors, and finally the mean daily percentage change calculated from all days of evaluation. Results are shown in FIG. 8A (secreted markers-% daily average change).

Figure 8B:
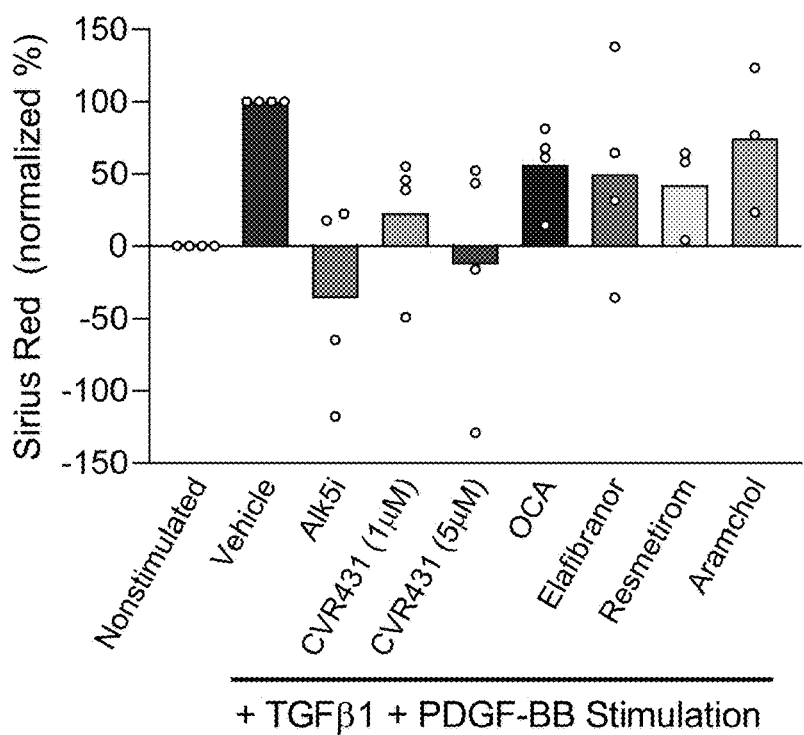

(b) Sirius red histological staining. PCLS were processed histologically at the end of the experiments and stained with Sirius red to demonstrate tissue fibrosis. Sirius red was quantified morphometrically in the histological sections as the percentage area with Sirius red staining in 10 sections from each treatment. In the Nonstimulation Protocol the quantity of Sirius red staining was expressed relative to the vehicle group. In the Stimulation Protocol the quantity of Sirius red staining was expressed relative to nonstimulated PCLS (0%) and TGFβ+PDGF-BB-stimulated+vehicle PCLS (100%). Results are shown in FIG. 8B (Sirius red staining for tissue fibrosis).

Figure 8C:
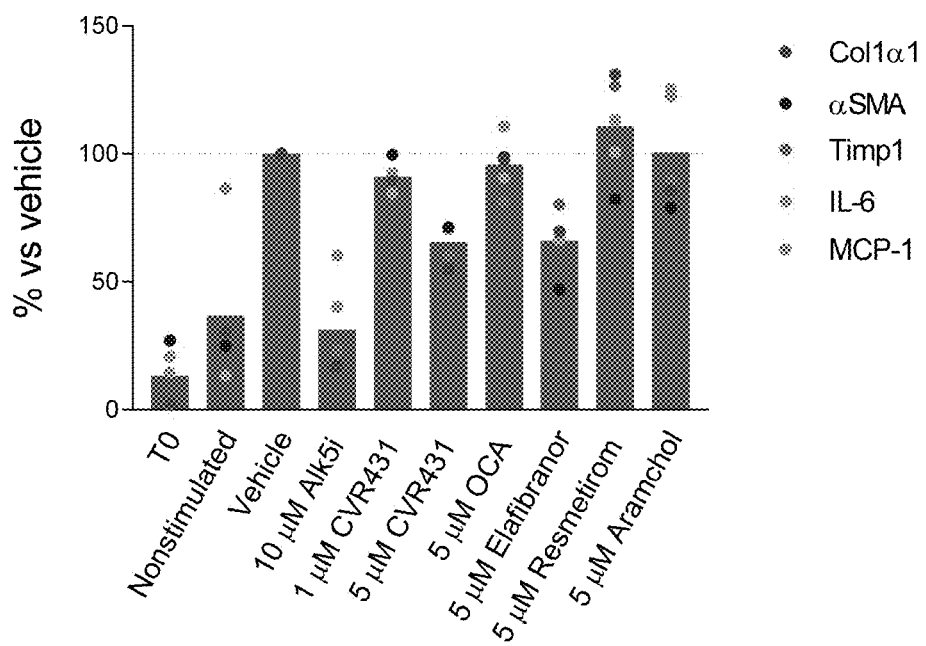

(c) Gene expression by RT-PCR. RNA was isolated from duplicate liver slices per treatment at the end of the experiments and evaluated by RT-PCR for 5 markers of inflammation and fibrosis: MCP-1, IL-6, TIMP1, αSMA, and collagen 1α1. β actin was used as a reference gene to calculate relative levels of each target gene RNA. CRV431 applied at 5 µM concentration decreased the mean daily secretion and gene expression of all markers in similarity to Alk5i (inhibitor of TGFβ receptor kinase), pirfenidone (approved treatment for IPF), and nintedanib (approved treatment for IPF). Results are shown in FIG. 8C (gene expression by RT-PCR).

(d) Gene expression by RNA-Seq. RNA sequencing of the complete transcriptome (30 million reads per sample) was conducted on vehicle and 5 µM CRV431 treatment groups from 3 donors both from the Nonstimulation and Stimulation Protocols. Data were analyzed by bioinformatics software programs to identify genes that were differentially expressed between vehicle and CRV431 treatments.

For the evaluation done for (d), 12 samples corresponding to 3 different donor slides which underwent 4 different treatments were studied. the comparisons carried out in this analysis are: (1) TGFb/PDGF+CRV vs TGFb/PDGF+Vehicle (V), and (2) Non-stimulated+CRV vs Non-stimulated+Vehicle. Table 1 shows sample ID and the corresponding treatment. Table 1. Samples for evaluation (d)

| Sample ID | Treatment |
| --- | --- |
| CVR_2.1_3 | TGFb/PDGF + V |
| CVR_2.1_9 | TGFb/PDGF + CRV |
| CVR_2.1_19 | Control + V |
| CVR_2.1_21 | Control + CRV |
| CVR_2.2_3 | TGFb/PDGF + V |
| CVR_2.2_9 | TGFb/PDGF + CRV |
| CVR_2.2_19 | Control + V |
| CVR_2.2_21 | Control + CRV |
| CVR_2.4_3 | TGFb/PDGF + V |
| CVR_2.4_9 | TGFb/PDGF + CRV |
| CVR_2.4_19 | Control + V |
| CVR_2.4_21 | Control + CRV |

Quality Control check was performed in all samples. All samples had more than 30 million reads and a quality score average >35 for almost all the bases in the sequences. The duplication levels are expected as it is RNA sequencing, and different copies of the same RNA are expected to be present in the samples. All samples had good amount of reads and quality, therefore all samples passed the QC checked and were included in the analysis.

Figure 9A:
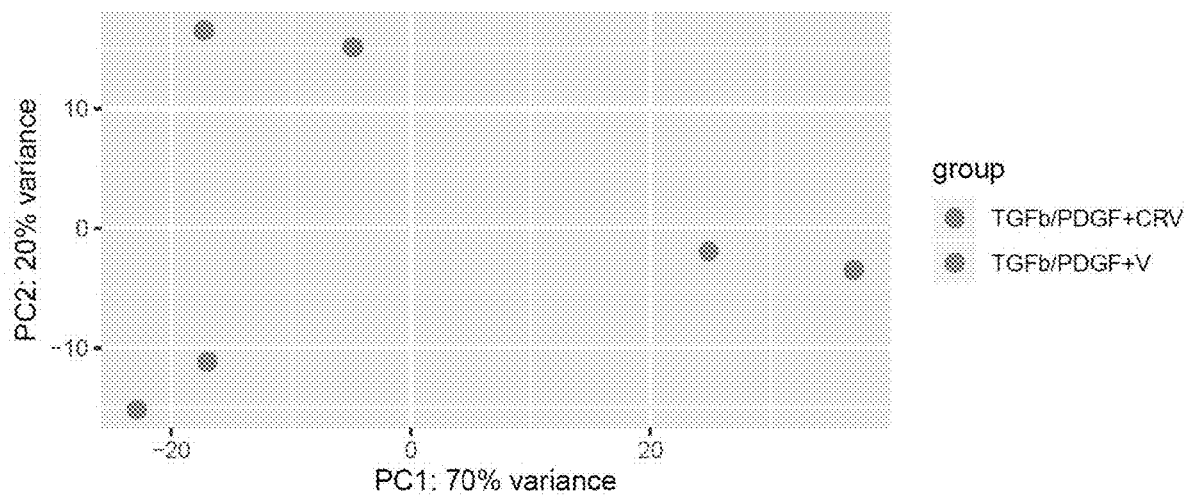
FIGS. 9A-B are PCA plots showing the distribution of the sample and donor for comparison of TGFb/PDGF+CRV431 vs TGFb/PDGF+Vehicle by group.
Figure 9B:
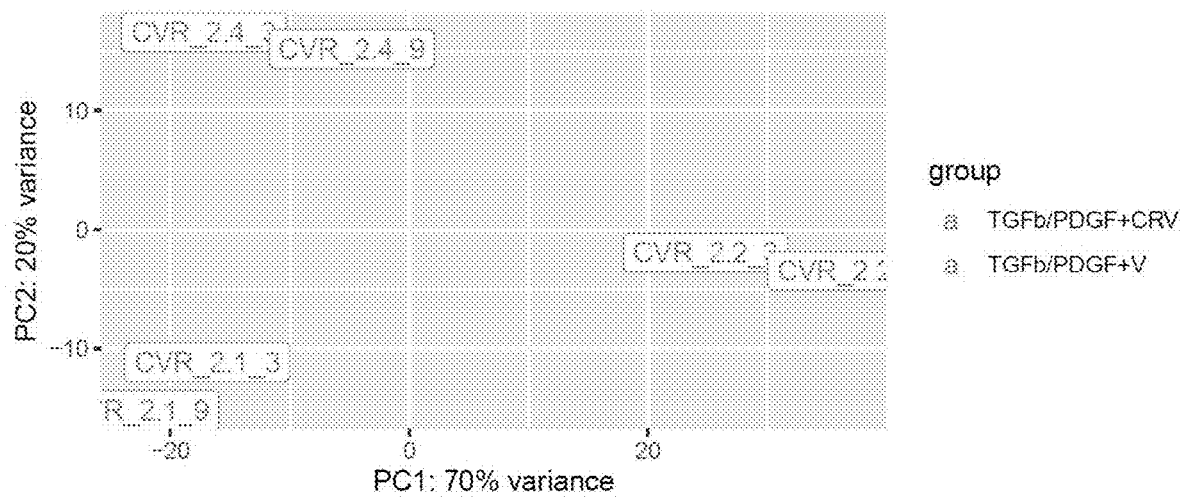

TGFb/PDGF+CRV431 vs TGFb/PDGF+Vehicle were compared by group. A Principal Components Analysis (PCA) plot was generated to analyze the distribution of the sample (FIG. 9A), which shows a strong effect of the donor, as they cluster together based on donor; however, there are also differences between the treatment, as they separate in the PCA plot as shown in FIG. 9B.

Figure 9C:
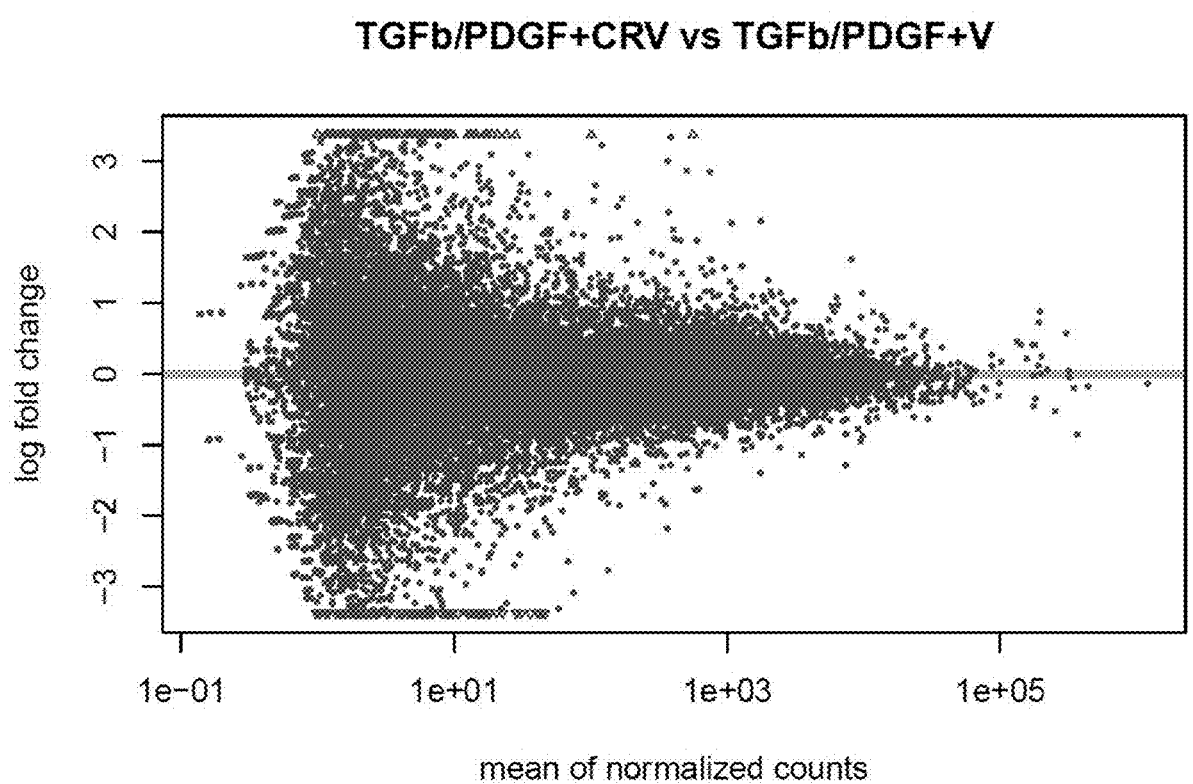
FIG. 9C is a MA plot.

In the MA plot of FIG. 9C, mean counts were plotted against the log fold change. Showing in red the significant genes differently expressed in the comparison TGFb/PDGF+CRV and TGFb/PDGF+Vehicle (p-adjust<0.05).

Figure 10A:
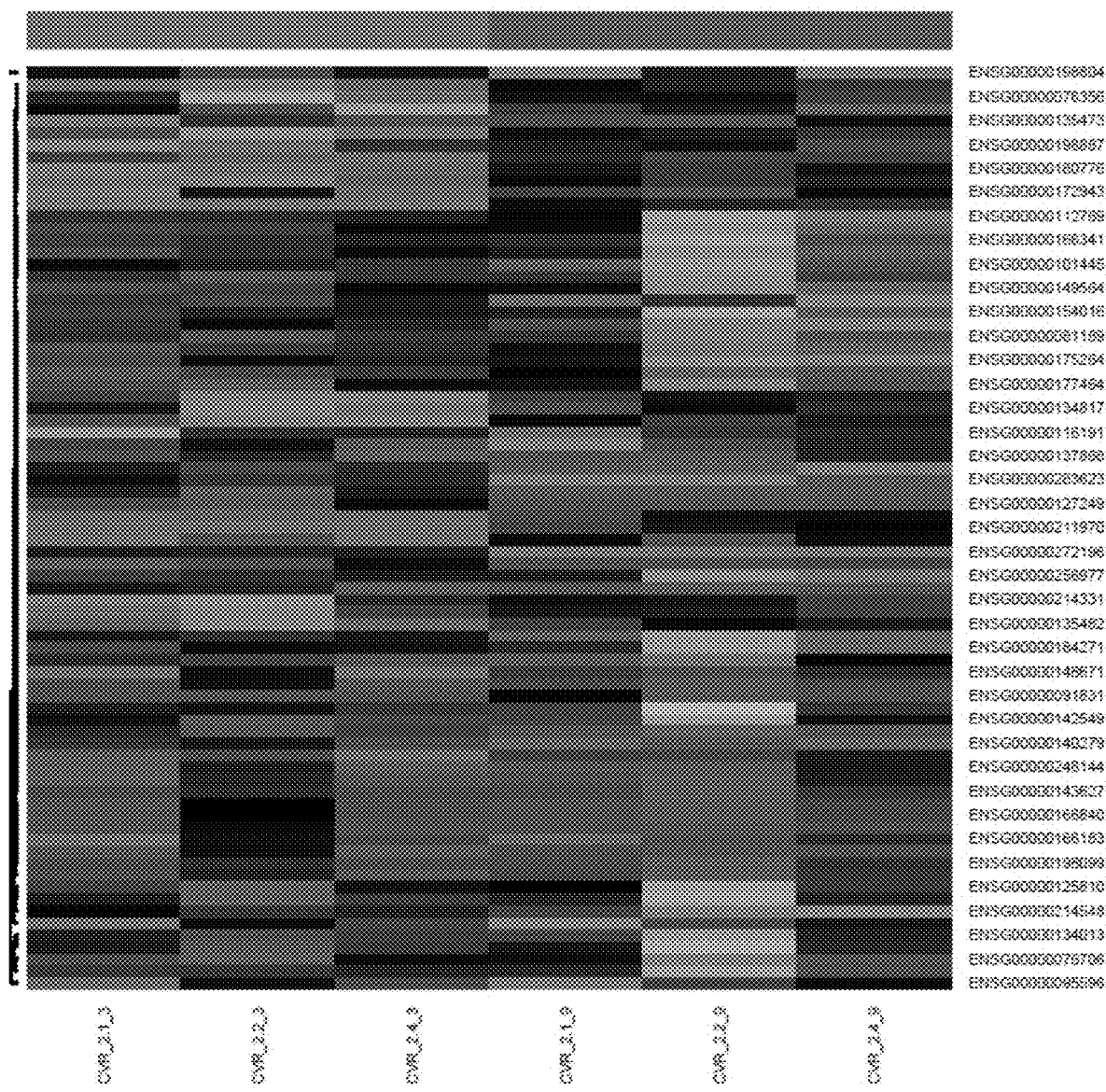
FIGS. 10A-B are heatmap generated for comparison of TGFb/PDGF+CRV431 vs TGFb/PDGF+Vehicle by group.
Figure 10B:
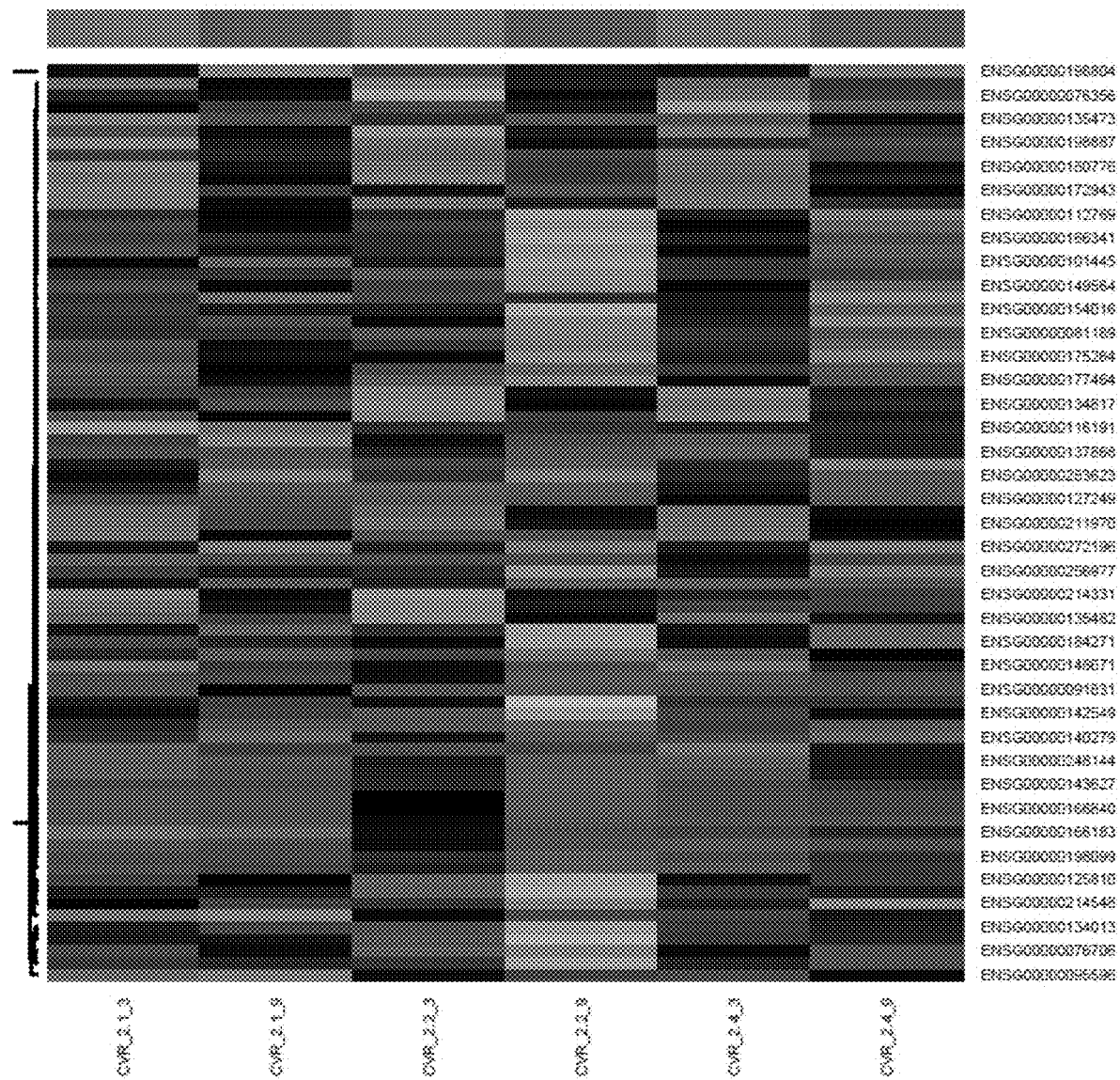

Heatmaps were also generated to plot significant differently expressed genes for the comparison TGFb/PDGF+CRV and TGFb/PDGF+Vehicle (p-adjust<0.05, log fold change >0.5). The heatmap with the samples grouped by group is shown in FIG. 10A to observe the different expression pattern present within the group (blue=vehicle; red=CRV). The same significant genes were also plotted into another heatmap (FIG. 10B) but the samples are now plotted grouped by donor in order to observe the differences between donors (blue=vehicle; red=CRV).

Figure 11:
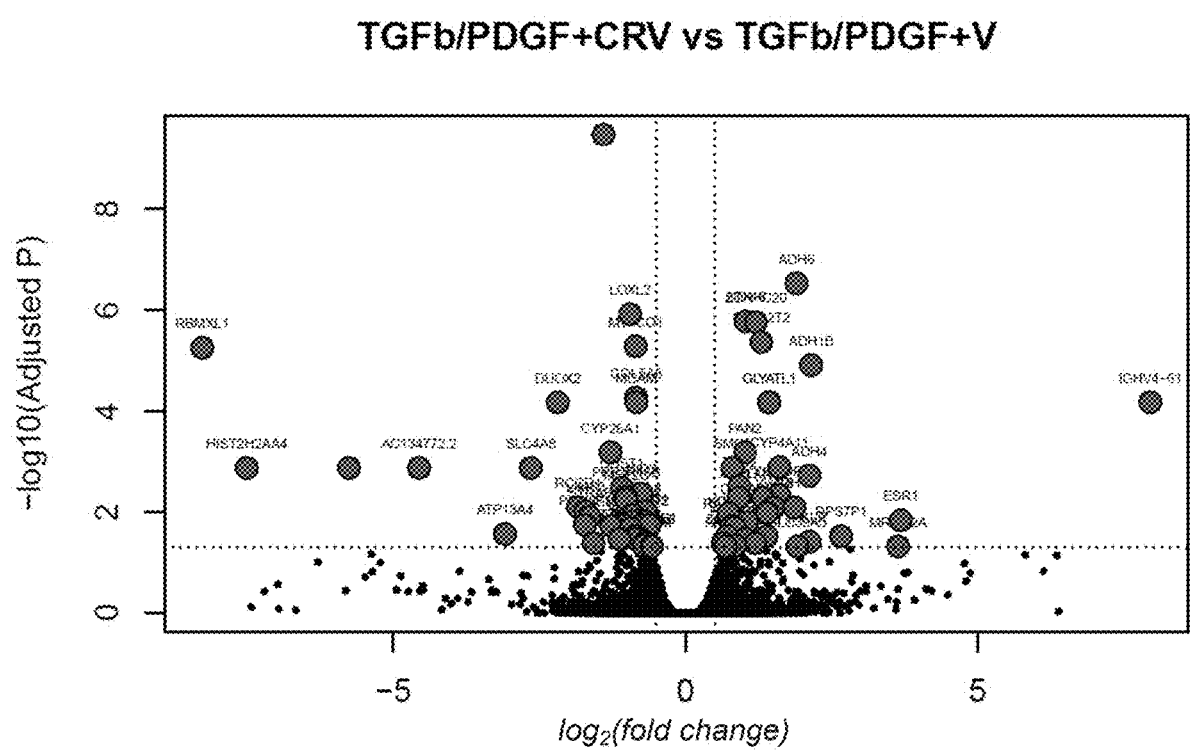
FIG. 11 is a volcano plot showing significant differently expressed genes identified in the comparison of TGFb/PDGF+CRV431 vs TGFb/PDGF+Vehicle by group.

In addition, significant hits are plotted in a volcano plot (FIG. 11), in which the significant genes were plotted in red and labelled with their correspondent symbol ID. Down and up-regulated are relative to CRV treatment.

Significant differently expressed genes that were identified in the comparison TGFb/PDGF+CRV and TGFb/PDGF+Vehicle (p-adjust>0.05, log fold change>0.5) are shown in Table 2. The fold change is relative to the treatment (CRV).

Table 2. Significant differently expressed genes identified in the comparison TGFb/PDGF+CRV and TGFb/PDGF+Vehicle

| ensembl_geneid | symbol | log2Fold-Change | padj |
| --- | --- | --- | --- |
| ENSG00000164283 | ESM1 | −1.401 | 3.29283493401111e−10 |
| ENSG00000172955 | ADH6 | 1.903 | 2.94236428678419e−07 |
| ENSG00000134013 | LOXL2 | −0.948 | 1.19798115569287e−06 |
| ENSG00000124222 | STX16 | 1.025 | 1.67355828789889e−06 |
| ENSG00000180776 | ZDHHC20 | 1.207 | 1.73084943004934e−06 |
| ENSG00000078699 | CBFA2T2 | 1.299 | 4.29111173342668e−06 |
| ENSG00000198804 | MT-CO1 | −0.85 | 5.14890213770242e−06 |
| ENSG00000213516 | RBMXL1 | −8.265 | 5.51686338456531e−06 |
| ENSG00000196616 | ADH1B | 2.156 | 1.22290666093167e−05 |
| ENSG00000080573 | COL5A3 | −0.842 | 5.37672079837298e−05 |
| ENSG00000076706 | MCAM | −0.841 | 6.63581694668706e−05 |
| ENSG00000140279 | DUOX2 | −2.182 | 6.63581694668706e−05 |
| ENSG00000166840 | GLYATL1 | 1.438 | 6.63581694668706e−05 |
| ENSG00000166840 | GLYATL1 | 1.438 | 6.63581694668706e−05 |
| ENSG00000211970 | IGHV4-61 | 7.957 | 6.63581694668706e−05 |
| ENSG00000095596 | CYP26A1 | −1.283 | 0.000663869405904214 |
| ENSG00000135473 | PAN2 | 1.019 | 0.000663869405904214 |
| ENSG00000187048 | CYP4A11 | 1.611 | 0.00131126021103255 |
| ENSG00000050438 | SLC4A8 | −2.641 | 0.00135464161540089 |
| ENSG00000198887 | SMC5 | 0.799 | 0.00135464161540089 |
| ENSG00000272196 | HIST2H2AA4 | −7.504 | 0.00135464161540089 |
| ENSG00000282827 | AC134772.2 | −4.561 | 0.00135464161540089 |
| ENSG00000283623 | NA | −5.759 | 0.00135464161540089 |
| ENSG00000198099 | ADH4 | 2.123 | 0.00191949000960653 |
| ENSG00000151790 | TDO2 | 0.916 | 0.00312047886997339 |
| ENSG00000175264 | CHST1 | −1.087 | 0.0033627319829465 |
| ENSG00000087303 | NID2 | −0.755 | 0.00436564894103764 |
| ENSG00000154639 | CXADR | 1.61 | 0.00465248444892784 |
| ENSG00000101445 | PPP1R16B | −1.016 | 0.00504512080532397 |
| ENSG00000076356 | PLXNA2 | 1.326 | 0.00524948770298015 |
| ENSG00000166183 | ASPG | 0.91 | 0.00524948770298015 |
| ENSG00000081189 | MEF2C | −1.013 | 0.00569870441559758 |
| ENSG00000166965 | RCCD1 | −1.838 | 0.00813696698391237 |
| ENSG00000102763 | VWA8 | 1.514 | 0.00820494655996272 |
| ENSG00000248144 | ADH1C | 1.869 | 0.00820494655996272 |
| ENSG00000128917 | DLL4 | −0.69 | 0.00990020877847807 |
| ENSG00000256977 | LIMS3 | −1.705 | 0.00990020877847807 |
| ENSG00000148671 | ADIRF | 1.402 | 0.0105361838033656 |
| ENSG00000112936 | C7 | 0.739 | 0.0107467217612096 |
| ENSG00000177464 | GPR4 | −0.9 | 0.0116584644837567 |
| ENSG00000137868 | STRA6 | −1.639 | 0.0126077678419959 |
| ENSG00000091831 | ESR1 | 3.688 | 0.0146645434418194 |
| ENSG00000154016 | GRAP | −0.772 | 0.0146645434418194 |
| ENSG00000166341 | DCHS1 | −0.686 | 0.0157049728052682 |
| ENSG00000140519 | RHCG | −0.927 | 0.0157568332080644 |
| ENSG00000175606 | TMEM70 | 1.062 | 0.0157568332080644 |
| ENSG00000113555 | PCDH12 | −0.741 | 0.0183319430393364 |
| ENSG00000125810 | CD93 | −0.613 | 0.0183319430393364 |
| ENSG00000184271 | POU6F1 | −1.716 | 0.0183319430393364 |
| ENSG00000213886 | UBD | −1.035 | 0.0187122936785154 |
| ENSG00000147050 | KDM6A | 0.785 | 0.019070909371344 |
| ENSG00000167178 | ISLR2 | −1.27 | 0.019070909371344 |
| ENSG00000116191 | RALGPS2 | 0.836 | 0.0205154157563514 |
| ENSG00000112769 | LAMA4 | −0.939 | 0.0213416290882877 |
| ENSG00000127249 | ATP13A4 | −3.082 | 0.0274603874188308 |
| ENSG00000142549 | IGLON5 | −0.851 | 0.030298756625196 |
| ENSG00000172943 | PHF8 | 0.709 | 0.0303737817896317 |
| ENSG00000197808 | ZNF461 | 1.391 | 0.0303737817896317 |
| ENSG00000263266 | RPS7P1 | 2.668 | 0.0303737817896317 |
| ENSG00000011028 | MRC2 | −0.773 | 0.0347062844025796 |
| ENSG00000135482 | ZC3H10 | 1.022 | 0.0347062844025796 |
| ENSG00000141540 | TTYH2 | −1.114 | 0.0347062844025796 |
| ENSG00000182379 | NXPH4 | −0.808 | 0.0347062844025796 |
| ENSG00000214548 | MEG3 | −0.853 | 0.0347062844025796 |
| ENSG00000260565 | ERVK13-1 | −1.125 | 0.0347062844025796 |
| ENSG00000143627 | PKLR | 2.127 | 0.0389991819266929 |
| ENSG00000003137 | CYP26B1 | −0.656 | 0.0406743042317417 |
| ENSG00000063180 | CA11 | −1.573 | 0.0417678950796777 |
| ENSG00000214331 | AC009053.1 | 1.194 | 0.0417678950796777 |
| ENSG00000225697 | SLC26A6 | −0.692 | 0.0417678950796777 |
| ENSG00000107404 | DVL1 | 0.635 | 0.0419108509612772 |
| ENSG00000127533 | F2RL3 | −0.711 | 0.0462741524861874 |
| ENSG00000134817 | APLNR | 0.844 | 0.0462741524861874 |
| ENSG00000139540 | SLC39A5 | 1.92 | 0.0484295024414694 |

-continued

| ensembl_geneid | symbol | log2Fold-Change | padj |
|---|---|---|---|
| ENSG00000149564 | ESAM | -0.573 | 0.0484295024414694 |
| ENSG00000185038 | MROH2A | 3.641 | 0.0484295024414694 |
| ENSG00000120137 | PANK3 | 0.687 | 0.0484878857306103 |

Figure 12A:
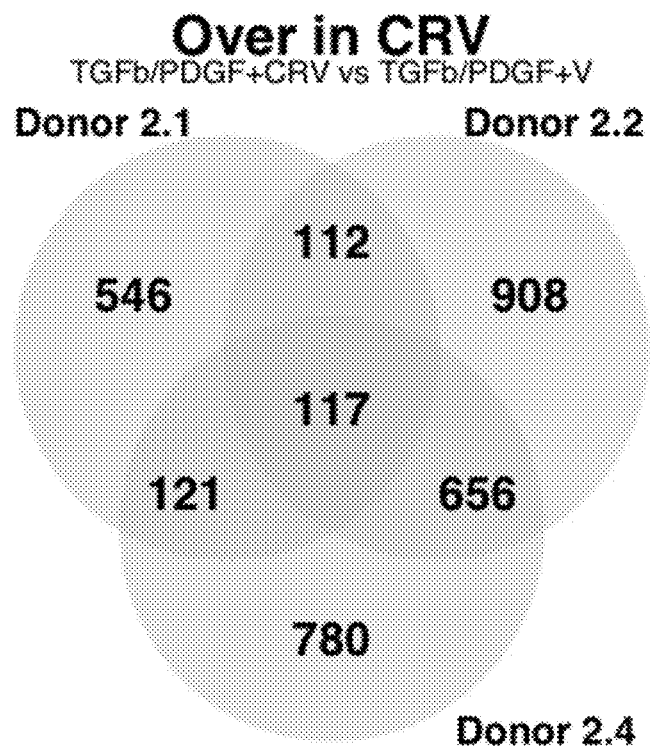
FIG. 12A-B are venn diagrams showing significant gene overlapping between all three donors.

As shown in the PCA analysis, there is a strong effect of the donor. Therefore, each donor was analyzed individually. Counts comparison was performed for TGFb/PDGF+CRV341 vs TGFb/PDGF+Vehicle by donor. First, genes that had a difference in the number of counts (TGFb/PDGF+Vehicle-TGFb/PDGF+CRV)<-300 were selected. Therefore the vehicle group had at least 300 copies less than CRV treatment. In other words, the treatment had at least 300 copies more than the Vehicle. After doing this selection individually for each donor, a venn diagram was plotted showing the overlapping between all three donors. As shown in FIG. 12A, 117 genes had at least 300 copies more in the CRV treated samples than in the vehicle.

Figure 12B:
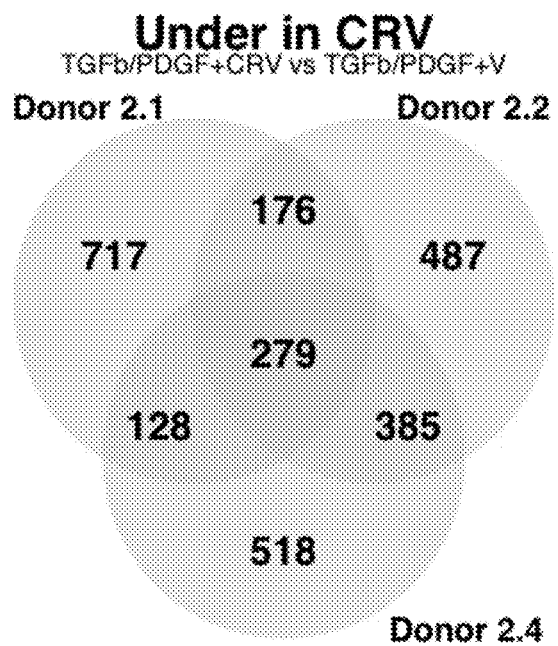

Then, genes that had a difference in the number of counts (TGFb/PDGF+Vehicle-TGFb/PDGF+CRV)>300 were selected, therefore those genes that had at least 300 more copies in the vehicle sample, compared to the CRV treated, were selected. So, they had at least 300 copies less in the CRV treatment compared to the vehicle. After doing the selection individually for each donor, a venn diagram was plotted showing the overlapping between all three donors. As shown in FIG. 12B, 279 genes had at least 300 copies less in the CRV treated than in the vehicle.

Figure 13A:
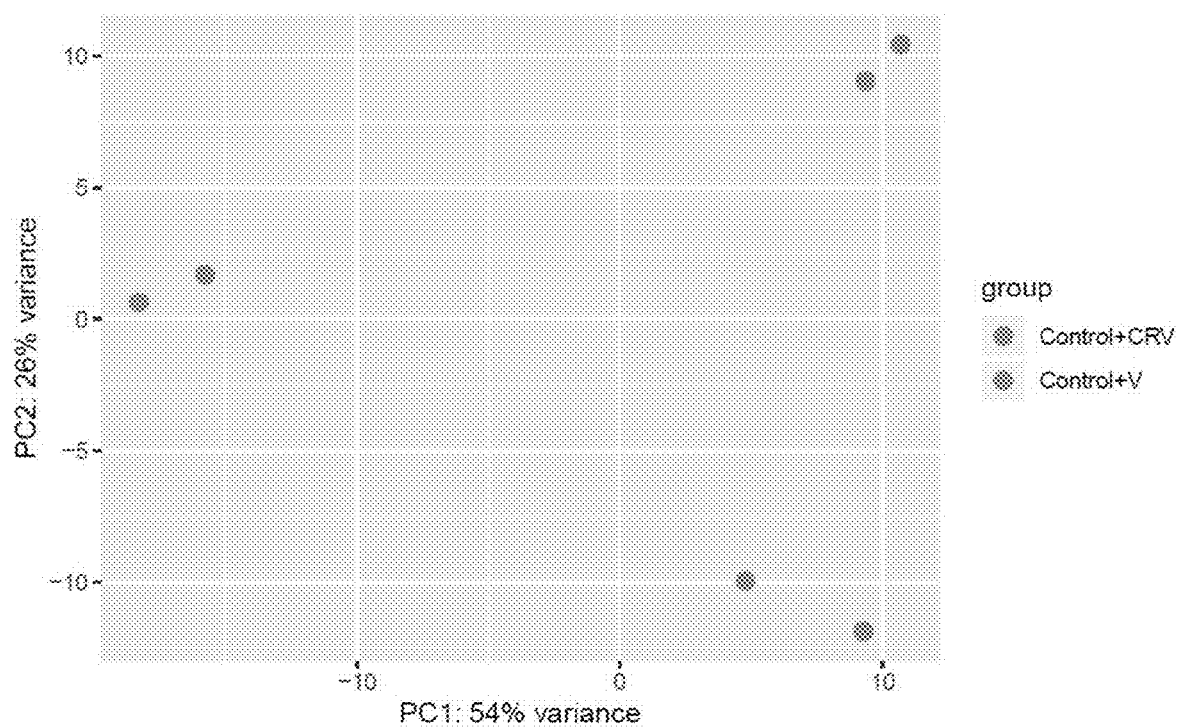
FIGS. 13A-B are PCA plots showing the distribution of the sample and donor for comparison of Nonstimulated+CRV431 vs Nonstimulated+Vehicle by group.
Figure 13B:
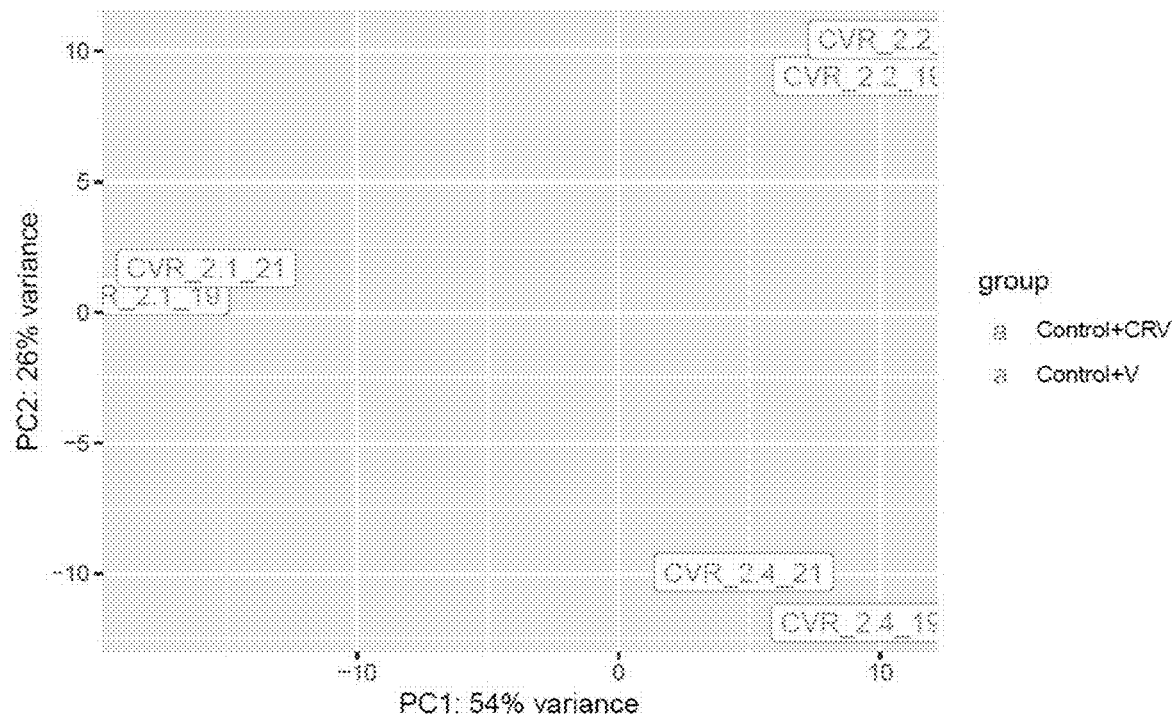

Nonstimulated+CRV431 vs Nonstimulated+Vehicle were then compared by group. A Principal Components Analysis (PCA) plot was generated to analyze the distribution of the sample (FIG. 13A). As expected, a strong effect of the donor was observed, as they cluster together base on donor and not on treatment. But there were differences between the treatment as they separate in the PCA plot (FIG. 13B).

Figure 13C:
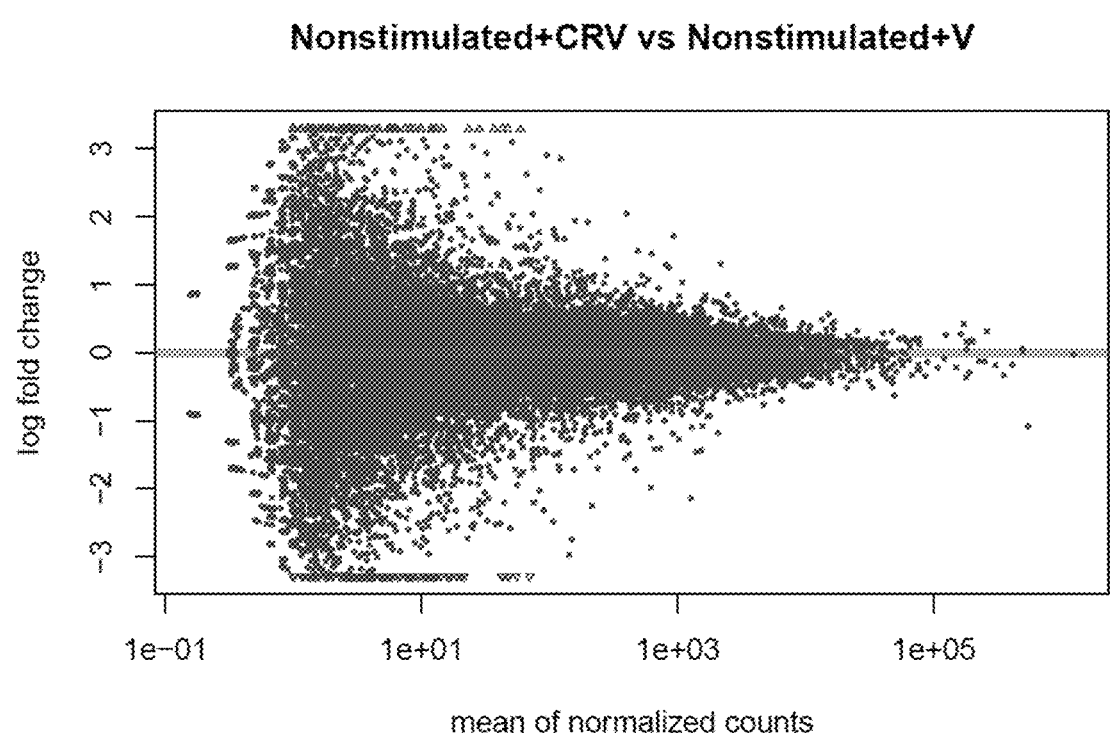
FIG. 13C is a MA plot.

For MA plot shown in FIG. 13C, mean counts were plotted against the log fold change. Showing in red the significant enes differently expressed in the comparison Non-stimulated +CRV and Non-stimulated+Vehicle (p-adjust<0.05).

Figure 14A:
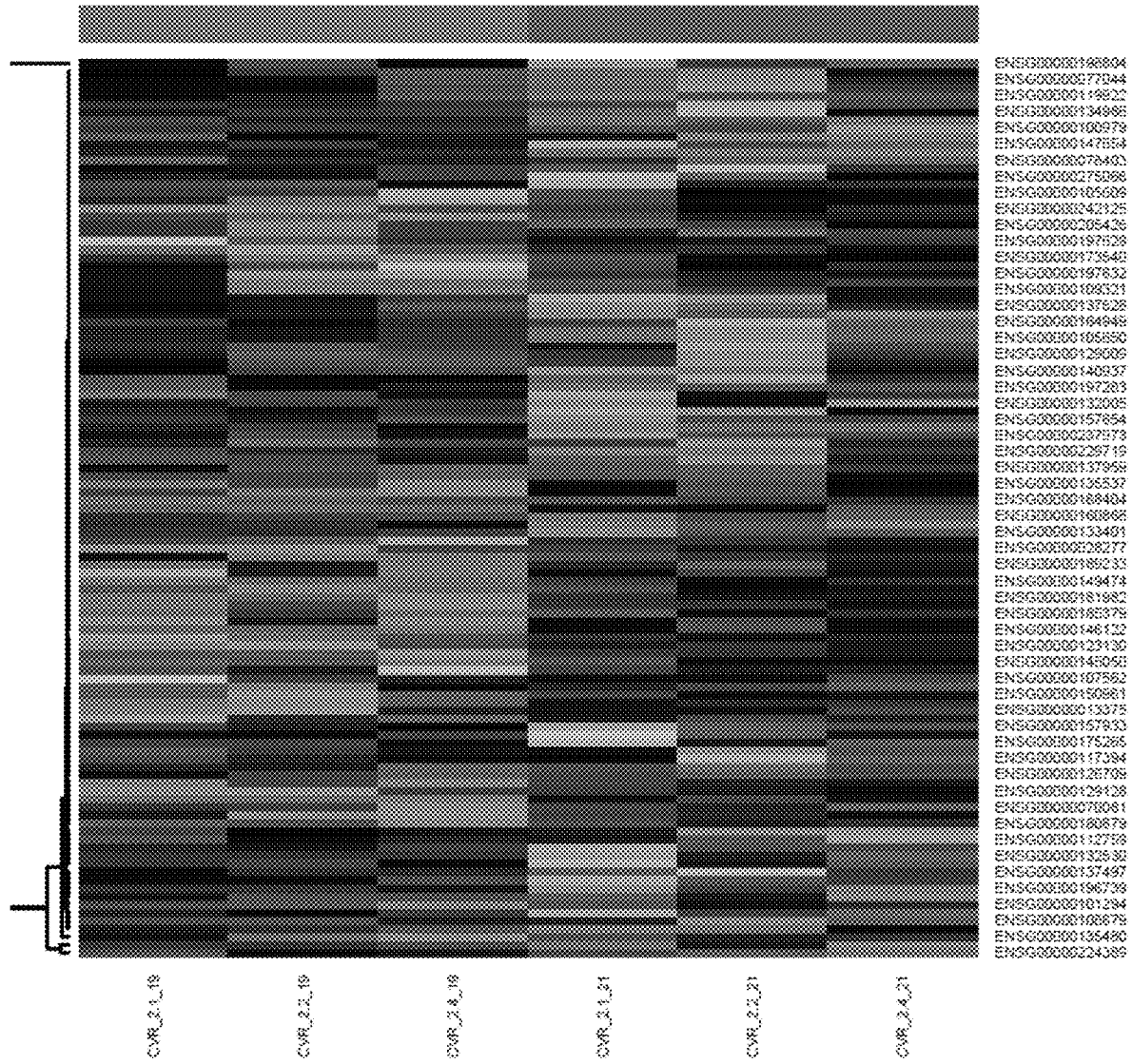
FIGS. 14A-B are heatmap generated for comparison of Nonstimulated+CRV431 vs Nonstimulated+Vehicle by group.
Figure 14B:
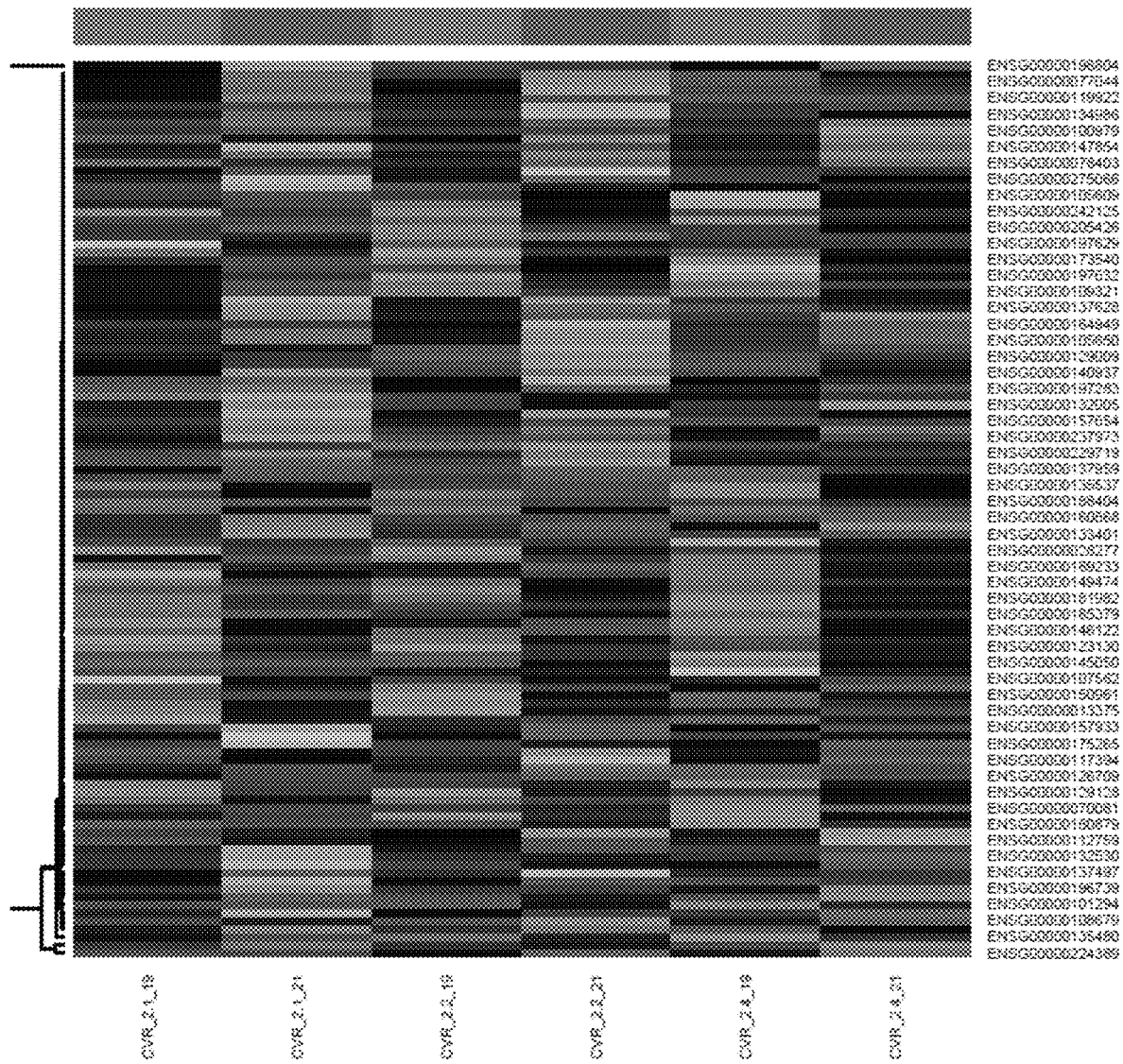

Heatmaps were generated by plotting significant differently expressed genes for the comparison Non-stimulated+CRV and Non-stimulated+Vehicle (p-adjust<0.05, log fold change >0.5). First, the heatmap with the samples grouped by group (FIG. 14A) is shown in order to observe the different expression pattern present within the group (blue=vehicle; red=CRV). Then, the same significant genes arweree plotted into a heatmap (FIG. 14B), but the samples are now plotted grouped by donor in order to observe the differences between donors (blue=vehicle; red=CRV).

Figure 15:
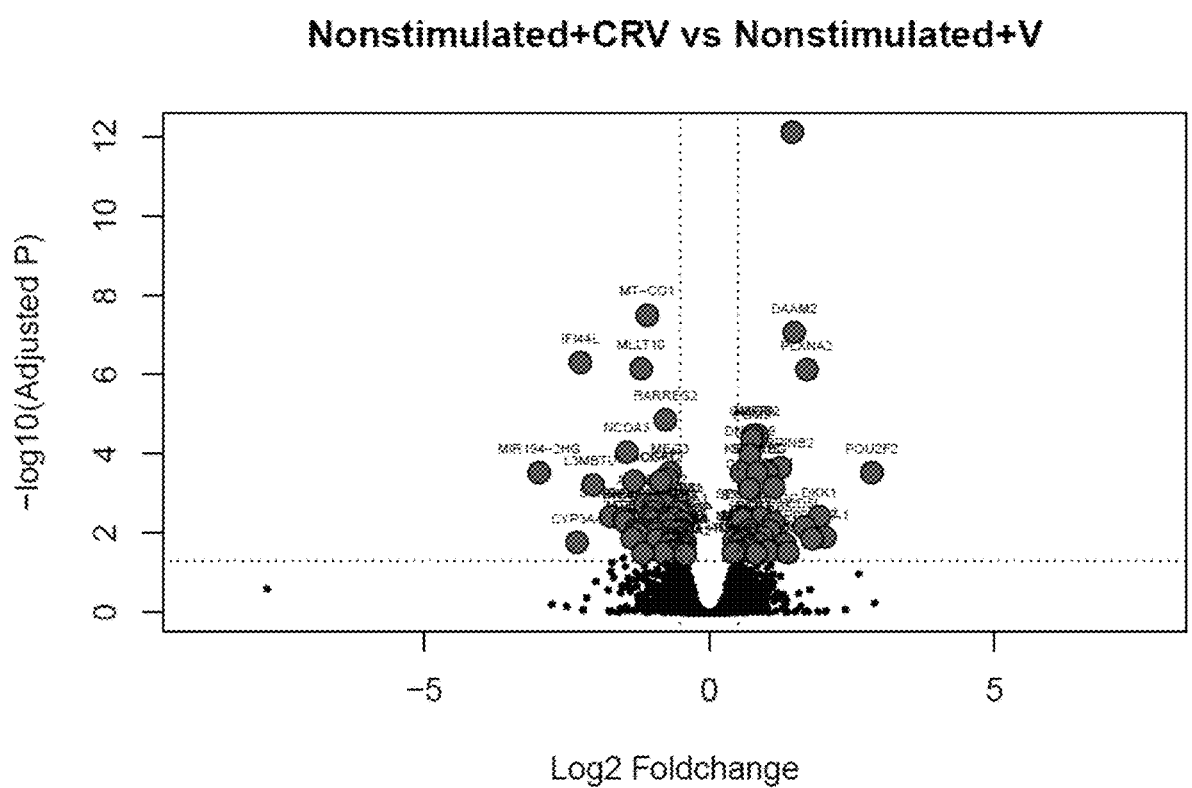
FIG. 15 is a volcano plot showing significant differently expressed genes identified in the comparison of Nonstimulated+CRV431 vs Nonstimulated+Vehicle by group.

Significant hits were plotted in a volcano plot (FIG. 15). The significant genes are plotted in red and labelled with its correspondent symbol ID. Down and up-regulated genes are relative to the treatment CRV.

Significant differently expressed genes that were identified in the comparison Non-stimulated+CRV and Non-stimulated+Vehicle (p-adjust>0.05, log fold change>0.5) are provided in Table 3. The fold changes shown are relative to the treatment CRV. Table 3. Significant differently expressed genes identified in the comparison Non-stimulated+CRV and Non-stimulated+Vehicle

| ensembl_geneid | symbol | log2Fold-Change | padj |
|---|---|---|---|
| ENSG00000242265 | PEG10 | 1.463 | 7.64497256360981e-13 |
| ENSG00000198804 | MT-CO1 | -1.083 | 3.14975868134979e-08 |
| ENSG00000146122 | DAAM2 | 1.498 | 8.53610989000754e-08 |
| ENSG00000137959 | IFI44L | -2.254 | 5.03046934688257e-07 |
| ENSG00000078403 | MLLT10 | -1.19 | 7.17576575470264e-07 |
| ENSG00000076356 | PLXNA2 | 1.719 | 7.55834893080804e-07 |
| ENSG00000106538 | RARRES2 | -0.766 | 1.40363819097048e-05 |
| ENSG00000070081 | NUCB2 | 0.851 | 3.45044971944497e-05 |
| ENSG00000144591 | GMPPA | 0.768 | 3.45044971944497e-05 |
| ENSG00000013375 | PGM3 | 0.751 | 4.29563263720564e-05 |
| ENSG00000124151 | NCOA3 | -1.438 | 9.05565703215956e-05 |
| ENSG00000128590 | DNAJB9 | 0.721 | 0.000105934561817305 |
| ENSG00000197632 | SERPINB2 | 1.255 | 0.0002233315832408411 |
| ENSG00000028277 | POU2F2 | 2.856 | 0.000298692252063288 |
| ENSG00000109321 | AREG | 1.034 | 0.000298692252063288 |
| ENSG00000135480 | KRT7 | 0.563 | 0.000298692252063288 |
| ENSG00000166562 | SEC11C | 0.844 | 0.000298692252063288 |
| ENSG00000214548 | MEG3 | -0.682 | 0.000298692252063288 |
| ENSG00000229719 | MIR194-2HG | -2.973 | 0.000298692252063288 |
| ENSG00000132530 | XAF1 | -0.725 | 0.000442143354650337 |
| ENSG00000140525 | FANCI | -1.319 | 0.000486460299226267 |
| ENSG00000077044 | DGKD | -0.85 | 0.000490134073876104 |
| ENSG00000185513 | L3MBTL1 | -2.03 | 0.000606634757391397 |
| ENSG00000205426 | KRT81 | 1.137 | 0.000694123487010014 |
| ENSG00000173540 | GMPPB | 0.715 | 0.000764920012703645 |
| ENSG00000111452 | ADGRD1 | -1.126 | 0.00186864914063056 |
| ENSG00000147854 | UHRF2 | -0.778 | 0.00186864914063056 |
| ENSG00000164949 | GEM | -0.975 | 0.00200478523553848 |
| ENSG00000135709 | KIAA0513 | -0.98 | 0.00288083461992706 |
| ENSG00000170525 | PFKFB3 | -0.545 | 0.00288083461992706 |
| ENSG00000107984 | DKK1 | 1.939 | 0.0038442433397899 |
| ENSG00000197283 | SYNGAP1 | -1.718 | 0.0038442433397899 |
| ENSG00000150961 | SEC24D | 0.58 | 0.00406643464218239 |
| ENSG00000157654 | PALM2-AKAP2 | -1.035 | 0.00417168314039161 |
| ENSG00000204642 | HLA-F | -0.727 | 0.00417168314039161 |
| ENSG00000186818 | LILRB4 | 0.909 | 0.00417691201899714 |
| ENSG00000117394 | SLC2A1 | -0.635 | 0.00426895599329709 |
| ENSG00000132005 | RFX1 | -1.495 | 0.00426895599329709 |
| ENSG00000163430 | FSTL 1 | -0.595 | 0.00426895599329709 |
| ENSG00000124222 | STX16 | 0.577 | 0.00440249554429453 |
| ENSG00000134709 | HOOK1 | -0.998 | 0.00506965939803037 |
| ENSG00000133401 | PDZD2 | -1.468 | 0.00513572755975289 |
| ENSG00000189233 | NUGGC | 1.136 | 0.00557406393671569 |
| ENSG00000275066 | SYNRG | -0.74 | 0.00557406393671569 |
| ENSG00000073754 | CD5L | 1.675 | 0.00696061006715629 |
| ENSG00000126709 | IFI6 | -1.273 | 0.00812520880633794 |
| ENSG00000151893 | CACUL1 | -0.94 | 0.00812520880633794 |
| ENSG00000237973 | MTCO1P12 | -1.183 | 0.00812520880633794 |
| ENSG00000129128 | SPCS3 | 0.715 | 0.00830997247774313 |
| ENSG00000167861 | HID1 | 0.716 | 0.00836179166380686 |
| ENSG00000060237 | WNK1 | -0.698 | 0.00871291063051336 |
| ENSG00000105609 | LILRB5 | 1.075 | 0.00871291063051336 |
| ENSG00000108679 | LGALS3BP | -0.556 | 0.00931883426718094 |
| ENSG00000164283 | ESM1 | -1.157 | 0.00982663156220979 |
| ENSG00000157933 | SKI | -0.931 | 0.0101551930217387 |
| ENSG00000108599 | AKAP10 | -1.249 | 0.0104187139875557 |
| ENSG00000141994 | DUS3L | 0.745 | 0.0107670886056319 |
| ENSG00000163754 | GYG1 | 0.94 | 0.0124948431676863 |
| ENSG00000188404 | SELL | 2.035 | 0.0124948431676863 |
| ENSG00000170006 | TMEM154 | -1.351 | 0.013539360764021 |
| ENSG00000224389 | C4B | -0.506 | 0.013539360764021 |
| ENSG00000129009 | ISLR | -0.815 | 0.0136013822876729 |
| ENSG00000145050 | MANF | 0.682 | 0.0136013822876729 |
| ENSG00000074181 | NOTCH3 | -0.564 | 0.013877649399757 |
| ENSG00000196739 | COL27A1 | -0.545 | 0.013877649399757 |
| ENSG00000272578 | AP000347.1 | 1.809 | 0.013877649399757 |
| ENSG00000135473 | PAN2 | 0.742 | 0.0142537182784554 |
| ENSG00000059145 | UNKL | -0.916 | 0.0148533925176707 |
| ENSG00000105738 | SIPA1L3 | -0.652 | 0.014997918499619 |
| ENSG00000106803 | SEC61B | 0.602 | 0.015634934319665 |
| ENSG00000180879 | SSR4 | 0.564 | 0.015634934319665 |
| ENSG00000160868 | CYP3A4 | -2.313 | 0.0171844499432494 |
| ENSG00000112759 | SLC29A1 | -0.53 | 0.0171960065344814 |
| ENSG00000135744 | AGT | -0.627 | 0.0173515994784034 |
| ENSG00000099889 | ARVCF | -0.609 | 0.0181970100656262 |
| ENSG00000149474 | KAT14 | 0.874 | 0.0182111511073747 |
| ENSG00000101294 | HM13 | 0.528 | 0.0183391036656796 |

-continued

| ensembl_geneid | symbol | log2Fold-Change | padj |
|---|---|---|---|
| ENSG00000136383 | ALPK3 | −0.621 | 0.0183391036656796 |
| ENSG00000179912 | R3HDM2 | −0.678 | 0.0183391036656796 |
| ENSG00000125735 | TNFSF14 | −0.681 | 0.0186023821876669 |
| ENSG00000135537 | AFG1L | 1.327 | 0.0186023821876669 |
| ENSG00000226950 | DANCR | 0.693 | 0.020979092384978 |
| ENSG00000180900 | SCRIB | 0.661 | 0.0249785512795709 |
| ENSG00000163735 | CXCL5 | 0.663 | 0.0251528991580969 |
| ENSG00000214021 | TTLL3 | −0.579 | 0.0265583936173043 |
| ENSG00000100979 | PLTP | −0.584 | 0.0266061673079832 |
| ENSG00000259970 | AC099668.1 | 1.056 | 0.0273196728101709 |
| ENSG00000105650 | PDE4C | −0.669 | 0.028386879814035 |
| ENSG00000105650 | PDE4C | −0.669 | 0.028386879814035 |
| ENSG00000090061 | CCNK | 0.545 | 0.0285388969844227 |
| ENSG00000134061 | CD180 | 1.051 | 0.0285388969844227 |
| ENSG00000175265 | GOLGA8A | −0.669 | 0.0305240081123133 |
| ENSG00000185379 | RAD51D | 1.387 | 0.0308390955534405 |
| ENSG00000119922 | IFIT2 | −0.812 | 0.0311836408752711 |
| ENSG00000107282 | APBA1 | −1.158 | 0.0320978587782238 |
| ENSG00000165125 | TRPV6 | 0.83 | 0.0329864085040579 |
| ENSG00000107562 | CXCL12 | 0.623 | 0.0347973357286517 |
| ENSG00000134986 | NREP | −0.638 | 0.0347973357286517 |
| ENSG00000158555 | GDPD5 | −0.606 | 0.0347973357286517 |
| ENSG00000181982 | CCDC149 | 0.76 | 0.0347973357286517 |
| ENSG00000197629 | MPEG1 | 0.584 | 0.0347973357286517 |
| ENSG00000242125 | SNHG3 | 0.665 | 0.0347973357286517 |
| ENSG00000123130 | ACOT9 | 0.543 | 0.0375735367132606 |
| ENSG00000261578 | AP003119.3 | −0.67 | 0.0376685663501125 |
| ENSG00000137497 | NUMA1 | −0.537 | 0.0397028864413373 |
| ENSG00000137628 | DDX60 | −0.739 | 0.0409633137500865 |
| ENSG00000019186 | CYP24A1 | −1.499 | 0.0424990125003709 |
| ENSG00000196369 | SRGAP2B | −0.729 | 0.0424990125003709 |
| ENSG00000198142 | SOWAHC | −0.601 | 0.0424990125003709 |
| ENSG00000140937 | CDH11 | −0.915 | 0.0426576776979742 |
| ENSG00000110079 | MS4A4A | 0.735 | 0.0492158532765886 |

Figure 16A:
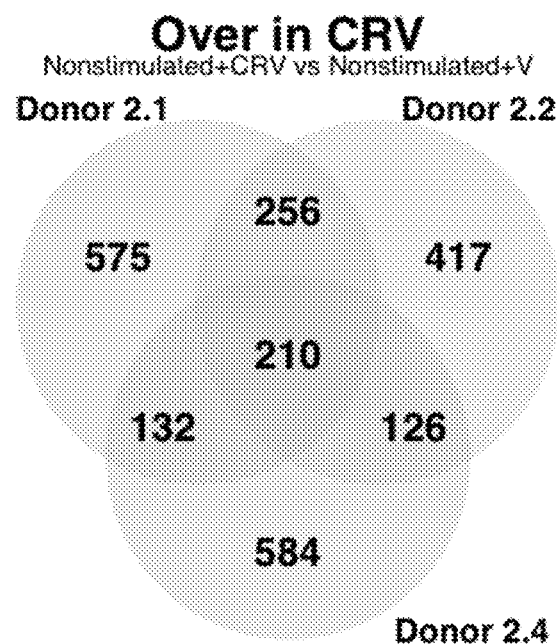
FIG. 16A-B are venn diagrams showing significant gene overlapping between all three donors for the comparison of Nonstimulated+CRV431 vs Nonstimulated+Vehicle by donor.
Figure 16B:
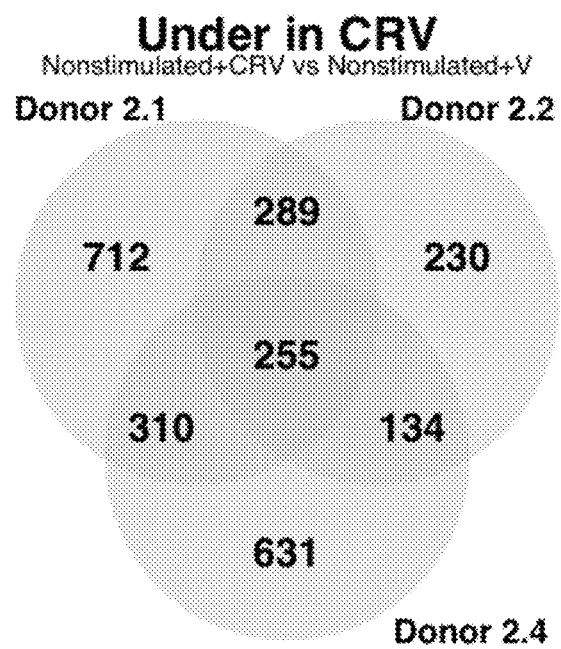

Nonstimulated+CRV431 vs Nonstimulated+Vehicle were then compared by donor. As shown in the PCA, there was a strong effect of the donor. Therefore, the analysis was repeated as in the previous comparison. Firstly, genes that had a difference in the number of counts (Non-stimulated+Vehicle−Non-stimulated+CRV)<−300 were selected, therefore the vehicle group had at least 300 copies less than CRV treatment. In other words, there were at least 300 copies more in the treatment CRV than in the vehicle. After doing this selection individually for each donor, a venn diagram was plotted showing the overlapping between all three donors. As shown in FIG. 16A, 210 genes had at least 300 copies more in the CRV treatment than in the Vehicle. Then, genes that had a difference in the number of counts (Non-stimulated+Vehicle−Non-stimulated+CRV)>300 were selected, therefore those genes that had at least 300 more copies in the vehicle sample, compared to the CRV treated, were selected. So, there are at least 300 copies less in the treated group compared to the vehicle. After doing the selection individually for each donor, a venn diagram was plotted showing the overlapping between all three donors. As shown in FIG. 16B, 255 genes had 300 or less copies in the CRV treated than in the vehicle.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for reducing production of extracellular matrix (ECM) molecules in a subject having fibrosis or at risk of developing fibrosis, the method comprising: selecting a composition to reduce the production of the ECM molecules in the subject, the composition comprising:

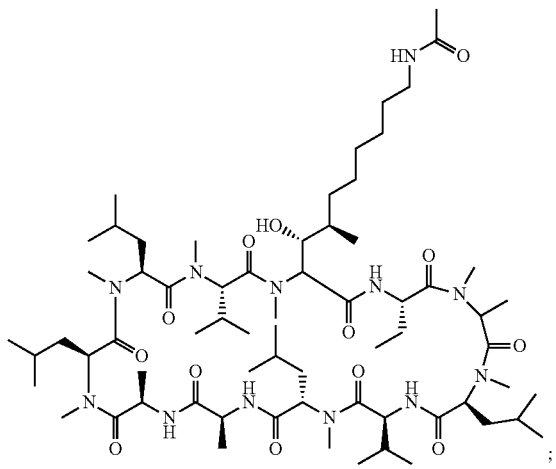

(CRV431)

and contacting at least one fibroblastic cell of the subject with an effective dose of the composition.

2. The method of claim 1, wherein the subject is suffering from fibrosis.

3. The method of claim 1, comprising inhibiting fibrosis formation in the subject.

4. The method of claim 1, wherein the fibrosis is non-liver fibrosis.

5. The method of claim 1, wherein the fibrosis is liver fibrosis.

6. The method of claim 5, wherein the liver fibrosis is cirrhosis or non-alcoholic steatohepatitis (NASH).

7. The method of claim 6, wherein the cirrhosis is associated with viral hepatitis, schistosomiasis and chronic alcoholism.

8. The method of claim 1, wherein the fibrosis is induced by a therapeutic agent, an injury, or a combination thereof.

9. The method of claim 1, comprising reducing fibrosis formation in the subject by at least 5%, 10%, 20%, 50%, 70%, 90%, or more as compared to untreated subjects.

10. The method of claim 1, comprising delaying fibrosis formation in the subject as compared to untreated subjects.

11. The method of claim 1, further comprising contacting the fibroblastic cell with one or more additional therapeutic agents.

12. The method of claim 11, wherein the one or more additional therapeutic agents comprise an additional antifibrotic agent or an anti-inflammatory agent.

13. The method of claim 1, further comprising after the contacting, measuring the expression of one or more biomarker genes selected from the group consisting of: Endothelial Cell Specific Molecule 1 (ESM1), Nuclear Receptor Coactivator 3 (NCOA3), Interferon Induced Protein 44 Like (IFI44L), MicroRNA 194-2 (mIR-194-2), Dickkopf WNT Signaling Pathway Inhibitor 1 (DKK1), Lysyl Oxidase Like 2 (LOXL2), Ubiquitin D/Human leukocyte antigen (HLA)-F adjacent transcript 10 (UBD/FAT10), STRA6 Signaling Receptor And Transporter Of Retinol (STRA6), RCC1 Domain Containing 1 (RCCD1), and Dual Oxidase 2 (DUOX2).

14. The method of claim 1, further comprising after the contacting, measuring secretion of one or more markers selected from monocyte chemoattractant protein (MCP-1), interleukin-6 (IL-6), matrix metalloproteinase-7 (MMP-7), tissue inhibitor of metalloproteinase-1 (TIMP1), hyaluronic acid, and collagen 1α1.

15. The method of claim 1, wherein the effective dose has a dose concentration ranging from 0.2 μM to 5 μM.

16. The method of claim 1, wherein the effective dose comprises an effective daily dose of CRV431 at from 10 mg to 250 mg.

17. The method of claim 1, wherein the fibroblast cell is selected from the group consisting of lung fibroblasts, cardiac fibroblasts, dermal fibroblasts, renal mesangial cells, and hepatic stellate cells.

18. A method for reducing non-liver fibrosis or reversing non-liver fibrosis in a subject having non-liver fibrosis, the method comprising:

administering to the subject having non-liver fibrosis a pharmaceutically effective amount of a composition comprising:

(CRV431)
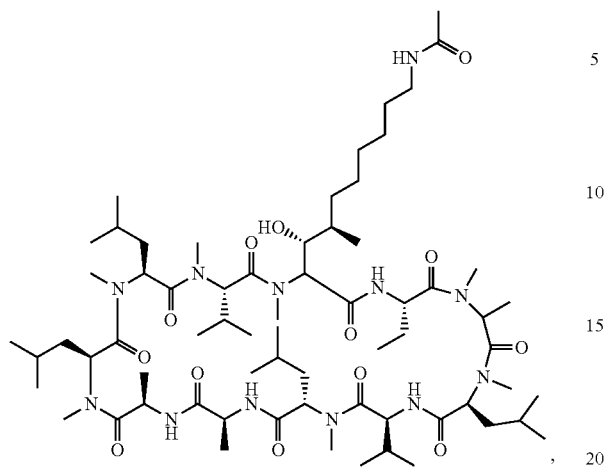
,
thereby reducing the non-liver fibrosis or reversing the non-liver fibrosis by reducing the production of extracellular matrix molecules.
19. The method of claim 18, wherein the non-liver fibrosis is pulmonary fibrosis or scleroderma.
* * * * *